United States Patent
Fang et al.

(10) Patent No.: US 12,317,874 B2
(45) Date of Patent: *Jun. 3, 2025

(54) METHOD OF USING A GENETICALLY MODIFIED MOUSE THAT EXPRESSES HUMAN ALBUMIN

(71) Applicant: Regeneron Pharmaceuticals, Inc., Tarrytown, NY (US)

(72) Inventors: Qing Fang, Chappaqua, NY (US); Chia-Jen Siao, New York, NY (US); Dan Chalothorn, New York, NY (US); KehDih Lai, Yardley, PA (US); Leah Sabin, Goldens Bridge, NY (US); Rachel Sattler, New York, NY (US); Brian Zambrowicz, Sleepy Hollow, NY (US); Lori Morton, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/175,010

(22) Filed: Feb. 27, 2023

(65) Prior Publication Data

US 2023/0232797 A1  Jul. 27, 2023

Related U.S. Application Data

(62) Division of application No. 16/894,302, filed on Jun. 5, 2020, now Pat. No. 11,622,547.

(60) Provisional application No. 62/916,666, filed on Oct. 17, 2019, provisional application No. 62/858,589, filed on Jun. 7, 2019.

(51) Int. Cl.
| | | |
|---|---|---|
| A01K 67/027 | (2024.01) | |
| A01K 67/0278 | (2024.01) | |
| A61K 49/00 | (2006.01) | |
| C07K 14/76 | (2006.01) | |
| C12N 15/85 | (2006.01) | |

(52) U.S. Cl.
CPC ...... *A01K 67/0278* (2013.01); *A61K 49/0008* (2013.01); *C07K 14/76* (2013.01); *C12N 15/8509* (2013.01); *A01K 2207/15* (2013.01); *A01K 2227/105* (2013.01); *A01K 2267/03* (2013.01); *C12N 2015/8527* (2013.01)

(58) Field of Classification Search
USPC .......................................................... 800/18
See application file for complete search history.

(56) References Cited

U.S. PATENT DOCUMENTS

| | | |
|---|---|---|
| 5,942,435 A | 8/1999 | Wheeler |
| 6,586,251 B2 | 7/2003 | Economides et al. |
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 9,150,847 B2 | 10/2015 | Rebar |
| 9,255,250 B2 | 2/2016 | Gregory et al. |
| 9,394,545 B2 | 7/2016 | Rebar |
| 9,497,944 B2 | 11/2016 | Daly |
| 9,732,356 B2 | 8/2017 | Alam et al. |
| 9,771,403 B2 | 9/2017 | Miller et al. |
| 9,777,281 B2 | 10/2017 | Rebar |
| 9,873,894 B2 | 1/2018 | Conway et al. |
| 9,877,988 B2 | 1/2018 | Rebar |
| 9,902,974 B2 | 2/2018 | Conway et al. |
| 9,956,247 B2 | 5/2018 | Rebar |
| 10,081,661 B2 | 9/2018 | Miller et al. |
| 10,329,582 B2 | 6/2019 | Lee et al. |
| 10,385,359 B2 | 8/2019 | Lee et al. |
| 10,612,041 B2 | 4/2020 | Barzel et al. |
| 10,767,175 B2 | 9/2020 | Dellinger et al. |
| 11,622,547 B2 * | 4/2023 | Fang ..................... C07K 14/76 800/3 |
| 2008/0078000 A1 | 3/2008 | Poueymirou et al. |
| 2011/0200982 A1 | 8/2011 | Stevens et al. |
| 2013/0042330 A1 | 2/2013 | Murphy et al. |
| 2013/0111617 A1 | 5/2013 | MacDonald et al. |
| 2013/0117873 A1 | 5/2013 | Wang et al. |
| 2013/0177960 A1 | 7/2013 | Rebar |

(Continued)

FOREIGN PATENT DOCUMENTS

| | | |
|---|---|---|
| CN | 1518596 A | 8/2004 |
| CN | 108513582 A | 9/2018 |

(Continued)

OTHER PUBLICATIONS

Viuff (J. Controlled Release, 2016, vol. 233, p. 22-30).*
Urano (J. Biol. Chem., 1986, vol. 261, No. 7, p. 3244-3251).*
Wang (PNAS, 1997, vol. 94, p. 11563-11566).*
Li (Blood, 2018, vol. 132, Supplement 1, 2458).*

(Continued)

*Primary Examiner* — Michael C Wilson
(74) *Attorney, Agent, or Firm* — Alston & Bird LLP

(57) ABSTRACT

Non-human animal genomes, non-human animal cells, and non-human animals comprising a humanized albumin (ALB) locus and methods of making and using such non-human animal genomes, non-human animal cells, and non-human animals are provided. Non-human animal cells or non-human animals comprising a humanized albumin locus express a human albumin protein or a chimeric albumin protein, fragments of which are from human albumin. Methods are provided for using such non-human animals comprising a humanized albumin locus to assess in vivo efficacy of human-albumin-targeting reagents such as nuclease agents designed to target human albumin.

30 Claims, 12 Drawing Sheets

Specification includes a Sequence Listing.

(56) References Cited

U.S. PATENT DOCUMENTS

| | | |
|---|---|---|
| 2013/0177983 A1 | 7/2013 | Rebar |
| 2013/0280222 A1 | 10/2013 | Kay et al. |
| 2013/0340104 A1 | 12/2013 | Murphy |
| 2014/0017212 A1 | 1/2014 | Rebar |
| 2014/0112896 A1 | 4/2014 | Rebar |
| 2014/0134662 A1 | 5/2014 | Flavell et al. |
| 2014/0155468 A1 | 6/2014 | Gregory et al. |
| 2014/0178879 A1 | 6/2014 | Economides et al. |
| 2014/0235933 A1 | 8/2014 | Lee et al. |
| 2014/0245467 A1 | 8/2014 | MacDonald et al. |
| 2014/0310828 A1 | 10/2014 | Lee et al. |
| 2014/0335063 A1 | 11/2014 | Cannon et al. |
| 2015/0056705 A1 | 2/2015 | Conway et al. |
| 2015/0106961 A1 | 4/2015 | Rojas et al. |
| 2015/0159172 A1 | 6/2015 | Miller et al. |
| 2015/0166618 A1 | 6/2015 | Miller et al. |
| 2015/0240263 A1 | 8/2015 | Holmes et al. |
| 2015/0313194 A1 | 11/2015 | Hu et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0344893 A1 | 12/2015 | Rebar |
| 2015/0376628 A1 | 12/2015 | Schoenherr et al. |
| 2015/0376651 A1 | 12/2015 | Frendewey et al. |
| 2016/0060656 A1 | 3/2016 | Rebar |
| 2016/0090607 A1 | 3/2016 | Conway et al. |
| 2016/0143953 A1 | 5/2016 | Gregory et al. |
| 2016/0145646 A1 | 5/2016 | Frendewey et al. |
| 2016/0298134 A1 | 10/2016 | Chen et al. |
| 2017/0016027 A1 | 1/2017 | Lee et al. |
| 2017/0119906 A1 | 5/2017 | Riley |
| 2017/0196992 A1 | 7/2017 | Holmes et al. |
| 2017/0245481 A1 | 8/2017 | Gusarova et al. |
| 2017/0342118 A1 | 11/2017 | Miller et al. |
| 2017/0355999 A1 | 12/2017 | Rebar |
| 2018/0110808 A1 | 4/2018 | Rebar |
| 2018/0117181 A1 | 5/2018 | Huston |
| 2018/0139940 A1 | 5/2018 | Macdonald et al. |
| 2018/0185516 A1 | 7/2018 | Ansell et al. |
| 2018/0214490 A1 | 8/2018 | Rebar |
| 2018/0243450 A1 | 8/2018 | Devalaraja-Narashimha et al. |
| 2018/0362601 A1 | 12/2018 | Miller et al. |
| 2019/0002869 A1 | 1/2019 | Yin et al. |
| 2019/0010490 A1 | 1/2019 | Cowan et al. |
| 2019/0076551 A1 | 3/2019 | Bogorad et al. |
| 2019/0098879 A1 | 4/2019 | Drummond-Samuelson et al. |
| 2019/0112353 A1 | 4/2019 | Yang et al. |
| 2019/0153440 A1 | 5/2019 | Kantardzhieva et al. |
| 2019/0211362 A1 | 7/2019 | Lundberg et al. |
| 2019/0225991 A1 | 7/2019 | Izpisua Belmonte et al. |
| 2019/0247517 A1 | 8/2019 | Brooks |
| 2019/0290783 A1 | 9/2019 | Voronina et al. |
| 2019/0365924 A1 | 12/2019 | Conway et al. |
| 2019/0382798 A1 | 12/2019 | Cowan et al. |
| 2019/0390195 A1 | 12/2019 | Tondera et al. |
| 2020/0015462 A1 | 1/2020 | Murphy et al. |
| 2020/0080082 A1 | 3/2020 | Lundberg et al. |
| 2020/0268906 A1 | 8/2020 | Finn et al. |
| 2020/0270617 A1 | 8/2020 | Finn et al. |
| 2020/0270618 A1 | 8/2020 | Finn et al. |
| 2020/0282079 A1 | 9/2020 | Holmes et al. |
| 2020/0289628 A1 | 9/2020 | Finn et al. |
| 2020/0315149 A1 | 10/2020 | Tang et al. |
| 2020/0318136 A1 | 10/2020 | Wang et al. |
| 2020/0340015 A1 | 10/2020 | Dahlman et al. |
| 2020/0383304 A1 | 12/2020 | Fang et al. |
| 2020/0384125 A1 | 12/2020 | Brooks |
| 2020/0385721 A1 | 12/2020 | Lee et al. |
| 2020/0385760 A1 | 12/2020 | Haines et al. |
| 2020/0392541 A1 | 12/2020 | Zhang et al. |
| 2021/0079427 A1 | 3/2021 | Chen et al. |
| 2021/0095316 A1 | 4/2021 | Kim et al. |
| 2021/0187125 A1 | 6/2021 | Brooks |
| 2021/0198696 A1 | 7/2021 | Kong et al. |
| 2021/0348159 A1 | 11/2021 | Brooks et al. |
| 2023/0232797 A1 | 7/2023 | Fang et al. |

FOREIGN PATENT DOCUMENTS

| | | |
|---|---|---|
| EP | 2872625 B1 | 11/2016 |
| EP | 3138910 B1 | 9/2017 |
| EP | 3196301 B1 | 10/2018 |
| EP | 3138911 B1 | 12/2018 |
| EP | 2839013 B1 | 8/2020 |
| EP | 3011031 B1 | 9/2020 |
| JP | 2024-533826 A | 11/2004 |
| WO | WO 2013/044008 A2 | 3/2013 |
| WO | WO 2014/011237 A1 | 1/2014 |
| WO | WO 2014/089212 A1 | 6/2014 |
| WO | WO 2014/130706 A1 | 8/2014 |
| WO | WO 2014/172489 A2 | 10/2014 |
| WO | WO 2014/186585 A2 | 11/2014 |
| WO | WO 2015/042557 A1 | 3/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/127439 A1 | 8/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/081923 A2 | 5/2016 |
| WO | WO 2017/011519 A1 | 1/2017 |
| WO | WO 2017/074526 A1 | 5/2017 |
| WO | WO 2017/077386 A1 | 5/2017 |
| WO | WO 2017/087780 A1 | 5/2017 |
| WO | WO 2017/091512 A1 | 6/2017 |
| WO | WO 2017/093804 A2 | 6/2017 |
| WO | WO 2017/109757 A1 | 6/2017 |
| WO | WO 2017/134529 A1 | 8/2017 |
| WO | WO 2017/141109 A1 | 8/2017 |
| WO | WO 2017/158422 A1 | 9/2017 |
| WO | WO 2018/007871 A1 | 1/2018 |
| WO | WO 2018/013932 A1 | 1/2018 |
| WO | WO 2018/075736 A1 | 4/2018 |
| WO | WO 2018/107026 A1 | 6/2018 |
| WO | WO 2018/126087 A1 | 7/2018 |
| WO | WO 2018/232382 A1 | 12/2018 |
| WO | WO 2019/079527 A1 | 4/2019 |
| WO | WO 2019/113310 A1 | 6/2019 |
| WO | WO 2019/118875 A1 | 6/2019 |
| WO | WO 2019/134561 A1 | 7/2019 |
| WO | WO 2019/140330 A1 | 7/2019 |
| WO | WO 2019/161310 A1 | 8/2019 |
| WO | WO 2019/237069 A1 | 12/2019 |
| WO | WO 2019/246203 A1 | 12/2019 |
| WO | WO 2020/006126 A1 | 1/2020 |
| WO | WO 2020/006131 A2 | 1/2020 |
| WO | WO 2020/006132 A1 | 1/2020 |
| WO | WO 2020/032986 A1 | 2/2020 |
| WO | WO 2020/079033 A1 | 4/2020 |
| WO | WO 2020/081843 A1 | 4/2020 |
| WO | WO 2020/082046 A2 | 4/2020 |
| WO | WO 2020/112908 A2 | 6/2020 |
| WO | WO 2020/168362 A1 | 8/2020 |
| WO | WO 2020/206162 A1 | 10/2020 |
| WO | WO 2020/210552 A1 | 10/2020 |
| WO | WO 2020/241679 A1 | 12/2020 |
| WO | WO 2020/247812 A1 | 12/2020 |
| WO | WO 2021-072115 A1 | 4/2021 |
| WO | WO 2021/083073 A1 | 5/2021 |
| WO | WO 2021/224416 A1 | 11/2021 |

OTHER PUBLICATIONS

Barthold, "Genetically altered mice: phenotypes, no phenotypes, and Faux phenotypes," Genetica, 122(1):75-88, (2004).

Barzel et al., "Promoterless gene targeting without nucleases ameliorates haemophilia B in mice," Nature, 517:360-364 and Extended Data, (2014).

Birling, et al., "Modeling human disease in rodents by CRISPR/Cas9 genome editing," Mamm. Genome, 28(7-8):291-301, (2017).

(56) References Cited

OTHER PUBLICATIONS

Brevini, et al., "No shortcuts to pig embryonic stem cells," Theriogenology, 74(4):544-550, (2010).
Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Clark, et al., "A future for transgenic livestock," Nat. Rev. Genet., 4(10):825-833, (2003).
Dechiara, T.M., et al., "VelociMouse: Fully ES Cell-Derived F0-Generation Mice Obtained from the Injection of ES Cells into Eight-Cell-Stage Embryos," Methods in Molecular Biology, 530(16): 311-324, (2009).
Dennis, "Welfare Issues of Genetically Modified Animals," ILAR J., 43(2):100-109, (2002).
Feng, Bo, "High-efficiency CRISPR-based technology for hemophilia B gene therapy," A-Biotech (Hong Kong) Co. Ltd. (2018).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Glik et al., "Dzh. Moleculyarnaya biotehnologiya. Printsipy i primeneniye, (Molecular Biotechnology, Principles and Applications)," Moscow: Mir, 2002, English translation.
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Harari et al., "Bridging the species divide: transgenic mice humanized for type-I interferon response," PLoS One 9(1):e84259, (2014).
He et al., "Knock-in of large reporter genes in human cells via CRISPR/Cas9-induced homology-dependent and independent DNA repair," Nucleic Acids Research, 44(9):e85, pp. 1-14, (2016).
Herndler-Brandstetter, et al., "Humanized mouse model supports development, function, and tissue residency of human natural killer cells," Proc. Natl. Acad. Sci. U.S.A., 114(45):E9626-E9634, (2017).
Hofker et al., "Transgenic mouse methods and protocols," Methods in molecular biology, 2002-2003, 209, p. 51-58.
Houdebine, "Methods to Generate Transgenic Animals," pp. 31-48 in "Genetic Engineering in Livestock: New Applications and Interdisciplinary Perspectives," Ed. Engelhard et al., (2009).
Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Kumar, et al., "Transgenic Mouse Technology: Principles and Methods," Methods Mol. Biol., 590:335-362, (2009).
Laoharawee et al., "Dose-Dependent Prevention of Metabolic and Neurologic Disease in Murine MPS II by ZFN-Mediated In Vivo Genome Editing," Molecular Therapy, 26(4):1127-1136, (2018).
Li et al., "A Novel Humanized Hemophilia—a Mouse Model to Facilitate Preclinical In Vivo Studies of Human Specific Fviiia-Mimetic Bispecific Antibodies," Blood, 132(Suppl. 1): 2458, (2018).
Lloyd, "A knockout mouse resource for the biomedical research community," Ann. N.Y. Acad. Sci., 1245:24-26, (2011).
Lute, et al., "Human CTLA4 knock-in mice unravel the quantitative link between tumor immunity and autoimmunity induced by anti-CTLA-4 antibodies," Blood, 106(9):3127-3133, (2005).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Papapetrou et al., "Gene Insertion Into Genomic Safe Harbors for Human Gene Therapy," Molecular Therapy, 24(4):678-684, (2016).
Paris, et al., "Equine embryos and embryonic stem cells: defining reliable markers of pluripotency," Theriogenology, 74(4): 516-524, (2010).
Peng et al., "Production of Human Albumin in Pig Through CRISPR/Cas9-Mediated Knockin of Human cDNA into Swine Albumin Locus in the Zygote," Sci. Rep., 5:16705, (2015).
Porro et al., "Promoterless gene targeting without nucleases rescues lethality of a Crigler-Najjar syndrome mouse model," EMBO Molecular Medicine, 9(10):1346-1355, (2017).
Poueymirou, et al., "F0 generation mice fully derived from gene-targeted embryonic stem cells allowing immediate phenotypic analyses," Nat. Biotechnol., 25(1):91-99, (2007).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Rybchin V.N., Osnovy geneticheskoy inzhenerii, Saint Petersburg, SHbGTU Publishing House, 2002, p. 411-413.
Sharma et al., "In vivo genome editing of the albumin locus as a platform for protein replacement therapy," Blood, 126(15):1777-1784 (2015).
Sigmund, "Viewpoint: Are Studies in Genetically Altered Mice Out of Control?," Arterioscler. Thromb. Vasc. Biol., 20(6):1425-1429, (2000).
Urano et al., "The human albumin gene. Characterization of the 5' and 3' flanking regions and the polymorphic gene transcripts," J. Biol. Chem., 261(7):3244-3251, (1986).
Valenzuela, et al., "High-throughput engineering of the mouse genome coupled with high-resolution expression analysis," Nat. Biotechnol., 21(6):652-659, (2003).
Viuff et al., "Generation of a double transgenic humanized neonatal Fc receptor (FcRn)/albumin mouse to study the pharmacokinetics of albumin-lined drugs," J. Control. Release, 223:22-30, (2015).
Wakchaure, et al., "Transgenic Animals: A Review on its Various Dimensions and Applications in Animal Biotechnology," International Journal of Emerging Technology and Advanced Engineering, 5(11):210-213, (2015).
Wang et al., "A factor IX-deficient mouse model for hemophilia B gene therapy," Proc. Natl. Acad. Sci. U.S.A., 94(21):11563-11566, (1997).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Zhu et al., "Humanising the mouse genome piece by piece," Nat. Commun. 10(1):1845, (Apr. 23, 2019).
U.S. Appl. No. 16/894,302, Non-Final Office Action mailed Jun. 16, 2022.
U.S. Appl. No. 16/894,302, Notice of Allowance mailed Nov. 29, 2022.
U.S. Appl. No. 16/894,302, Requirement for Restriction/Election mailed Apr. 1, 2022.
WIPO Application No. PCT/US2020/036412, PCT International Search Report and Written Opinion of the International Searching Authority mailed Sep. 18, 2020.
Anguela et al., "In Vivo Genome Editing of Liver Albumin for Therapeutic Gene Expression: Rescue of Hemophilic Mice Via Integration of Factor 9," Blood, 120(21):751, (2012).
Devoy, et al., "Genomically humanized mice: technologies and promises," Nat. Rev. Genet., author manuscript, 13(1):14-20, (2011).
Lee, et al., "Complete humanization of the mouse immunoglobulin loci enables efficient therapeutic antibody discovery," Nat. Biotechnol., 32(4):356-363, (2014).

(56) References Cited

OTHER PUBLICATIONS

MacDonald, et al., "Precise and in situ genetic humanization of 6 Mb of mouse immunoglobulin genes," Proc. Natl. Acad. Sci. U.S.A., 111(14):5147-5152, (2014).
Wechsler et al., "ZFN-Mediated Gene Targeting at the Albumin Locus in Liver Results in Therapeutic Levels of Human FIX in Mice and Non-Human Primates," Blood, 126(23):200, (Dec. 3, 2015).

* cited by examiner

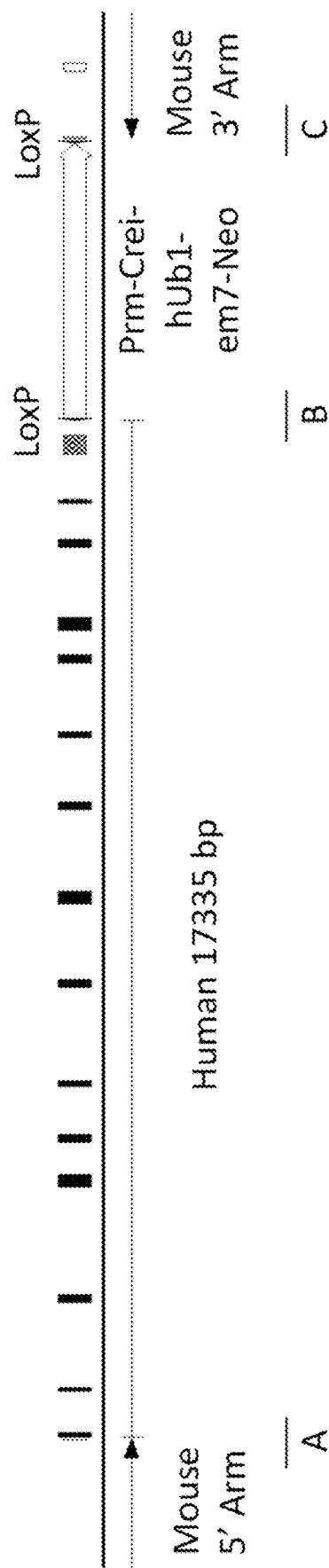
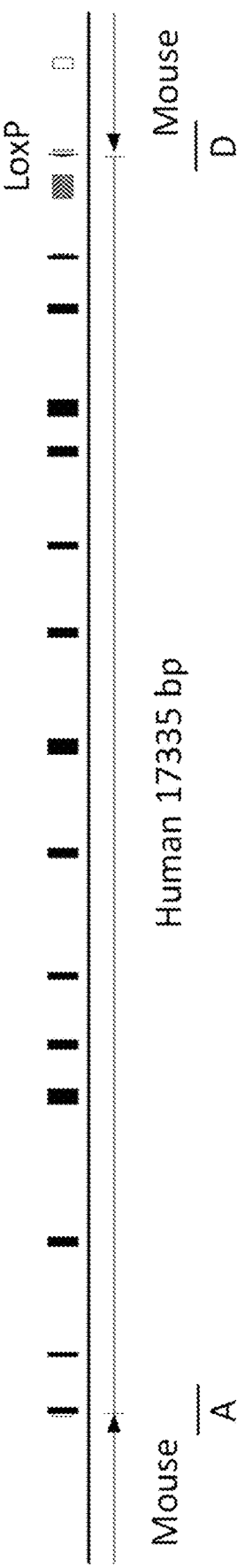
FIG. 1A
FIG. 1B

```
                    Signal peptide    Propeptide                           Serum peptide
mouse Alb         1 MKWVTFLLLLFVSGGSAFSRGVFRREAHKSEIAHRYNDLGEQHFKGLVLIAFSQYLQKCSY  60
human ALB         1 MKWVTFISLLFLFSSAYSRGVFRRDAHKSEVAHRFKDLGEENFKALVLIAFAQYLQQCPF  60
7626 HumIn Prot   1 MKWVTFISLLFLFSSAYSRGVFRRDAHKSEVAHRFKDLGEENFKALVLIAFAQYLQQCPF  60
                    **** * *  **** * *** ** * ****   * mouse Alb        61 DEHAKLVQEVTDFAKTCVADESAANCDKSLHTLFGDKLCAIPNLRENYGELADCCTKQEP 120
human ALB        61 EDHVKLVNEVTEFAKTCVADESAENCDKSLHTLFGDKLCTVATLRETYGEMADCCAKQEP 120
7626 HumIn Prot  61 EDHVKLVNEVTEFAKTCVADESAENCDKSLHTLFGDKLCTVATLRETYGEMADCCAKQEP 120
                      * * ******** ************ *   *  ** * mouse Alb       121 ERNECFLQHKDDNPSLPPFERPEAEAMCTSFKENPTTFMGHYLHEVARRHPYFYAPELLY 180
human ALB       121 ERNECFLQHKDDNPNLPRLVRPEVDVMCTAFHDNEETFLKKYLYEIARRHPYFYAPELLF 180
7626 HumIn Prot 121 ERNECFLQHKDDNPNLPRLVRPEVDVMCTAFHDNEETFLKKYLYEIARRHPYFYAPELLF 180
                   ************   *   * *  * *** ********** * mouse Alb       181 YAEQYNEILTQCCAEADKESCLTPKLDGVKEKALVSSVRQRMKCSSMQKFGERAFKAWAV 240
human ALB       181 FAKRYKAAFTECCQAADKAACLLPKLDELRDEGKASSAKQRLKCASLQKFGERAFKAWAV 240
7626 HumIn Prot 181 FAKRYKAAFTECCQAADKAACLLPKLDELRDEGKASSAKQRLKCASLQKFGERAFKAWAV 240
                    *   *     *   *** *    * ** * ************ mouse Alb       241 ARLSQTFPNADFAEITKLATDLTKVNKECCHGDLLECADDRAELAKYMCENQATISSKLQ 300
human ALB       241 ARLSQRFPKAEFAEVSKLVTDLTKVHTECCHGDLLECADDRADLAKYICENQDSISSKLK 300
7626 HumIn Prot 241 ARLSQRFPKAEFAEVSKLVTDLTKVHTECCHGDLLECADDRADLAKYICENQDSISSKLK 300
                   ***  * *    *** ************    *** mouse Alb       301 TCCDKPLLKKAHCLSEVEHDTMPADLPAIAADFVEDQEVCKNYAEAKDVFLGTFLYEYSR 360
human ALB       301 ECCEKPLLEKSHCIAEVENDEMPADLPSLAADFVESKDVCKNYAEAKDVFLGMFLYEYAR 360
7626 HumIn Prot 301 ECCEKPLLEKSHCIAEVENDEMPADLPSLAADFVESKDVCKNYAEAKDVFLGMFLYEYAR 360
                    ** **** * **  **** ****** ******   *********** ****** *
```

FIG. 3A

```
                              Serum peptide
                     ┌─────────────────────────────────────────────────────────────┐
mouse Alb      361   │RHPDYSVSLLLRLAKYEATLEKCCAEANPPACYGTVLAEFQPLVEEPKNLVKTNCDLYE│  420
human ALB      361   │RHPDYSVVLLRLAKTYETTLEKCCAAADPHECYAKVFDEFKPLVEEPQNLIKQNCELFE│  420
7626 HumIn Prot 361  │RHPDYSVVLLRLAKTYETTLEKCCAAADPHECYAKVFDEFKPLVEEPQNLIKQNCELFE│  420
                     │***** *** * ***********  * **** *  ***│  * mouse Alb      421   │KLGEYGFQNAILVRYTQKAPQVSTPTLVEAARNLGRVGTKCCTLPEDQRLPCVEDYLSAI│  480
human ALB      421   │QLGEYKFQNALLVRYTKKVPQVSTPTLVEVSRNLGKVGSKCCKHPEAKRMPCAEDYLSVV│  480
7626 HumIn Prot 421  │QLGEYKFQNALLVRYTKKVPQVSTPTLVEVSRNLGKVGSKCCKHPEAKRMPCAEDYLSVV│  480
                     │ **  *** * ********    * *   * ****   │  * mouse Alb      481   │LNRVCLLHEKTPVSEHVTKCCSGSLVERRPCFSALTVDETYVPKEFKAETFTFHSDICTL│  540
human ALB      481   │LNQLCVLHEKTPVSDRVTKCCTESLVNRPCFSALEVDETYVPKEFNAETFTFHADICTL│  540
7626 HumIn Prot 481  │LNQLCVLHEKTPVSDRVTKCCTESLVNRPCFSALEVDETYVPKEFNAETFTFHADICTL│  540
                     │** * ******* *** * * ** ****** *** ***│  * mouse Alb      541   │PEKEKQIKKQTALAELVKHKPKATAEQLKTVMDDFAQFLDTCCKAADKDTCFSTEGPNLV│  600
human ALB      541   │SEKERQIKKQTALVELVKHKPKATKEQLKAVMDDFAAFVEKCCKADDKETCFAEEGKKLV│  600
7626 HumIn Prot 541  │SEKERQIKKQTALVELVKHKPKATKEQLKAVMDDFAAFVEKCCKADDKETCFAEEGKKLV│  600
                     │ * **** ******   *** *  *** * * ***  *  **│  * mouse Alb      601   │TRCKDALA│  608    (SEQ ID NO: 1)
human ALB      601   │AASQAALGL│ 609    (SEQ ID NO: 5)
7626 HumIn Prot 601  │AASQAALGL│ 609    (SEQ ID NO: 5)
                     │  *      │  *
```

FIG. 3B

SEQUENCE LISTING

```
Sequence total quantity: 64
SEQ ID NO: 1            moltype = AA  length = 608
FEATURE                 Location/Qualifiers
REGION                  1..18
                        note = MISC_FEATURE - Signal Peptide
REGION                  19..24
                        note = MISC_FEATURE - Propeptide
REGION                  25..608
                        note = MISC_FEATURE - Serum Albumin
source                  1..608
                        mol_type = protein
                        organism = Mus musculus
SEQUENCE: 1
MKWVTFLLLL FVSGSAFSRG VFRREAHKSE IAHRYNDLGE QHFKGLVLIA FSQYLQKCSY  60
DEHAKLVQEV TDFAKTCVAD ESAANCDKSL HTLFGDKLCA IPNLRENYGE LADCCTKQEP  120
ERNECFLQHK DDNPSLPPFE RPEAEAMCTS FKENPTTFMG HYLHEVARRH PYFYAPELLY  180
YAEQYNEILT QCCAEADKES CLTPKLDGVK EKALVSSVRQ RMKCSSMQKF GERAFKAWAV  240
ARLSQTFPNA DFAEITKLAT DLTKVNKECC HGDLLECADD RAELAKYMCE NQATISSKLQ  300
TCCDKPLLKK AHCLSEVEHD TMPADLPAIA ADFVEDQEVC KNYAEAKDVF LGTFLYEYSR  360
RHPDYSVSLL LRLAKKYEAT LEKCCAEANP PACYGTVLAE FQPLVEEPKN LVKTNCDLYE  420
KLGEYGFQNA ILVRYTQKAP QVSTPTLVEA ARNLGRVGTK CCTLPEDQRL PCVEDYLSAI  480
LNRVCLLHEK TPVSEHVTKC CSGSLVERRP CFSALTVDET YVPKEFKAET FTFHSDICTL  540
PEKEKQIKKQ TALAELVKHK PKATAEQLKT VMDDFAQFLD TCCKAADKDT CFSTEGPNLV  600
TRCKDALA                                                         608

SEQ ID NO: 2            moltype = AA  length = 18
FEATURE                 Location/Qualifiers
source                  1..18
                        mol_type = protein
                        organism = Mus musculus
SEQUENCE: 2
MKWVTFLLLL FVSGSAFS                                               18

SEQ ID NO: 3            moltype = AA  length = 6
FEATURE                 Location/Qualifiers
source                  1..6
                        mol_type = protein
                        organism = Mus musculus
SEQUENCE: 3
RGVFRR                                                            6

SEQ ID NO: 4            moltype = AA  length = 584
FEATURE                 Location/Qualifiers
source                  1..584
                        mol_type = protein
                        organism = Mus musculus
SEQUENCE: 4
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALA                  584
```

```
SEQ ID NO: 5              moltype = AA  length = 609
FEATURE                   Location/Qualifiers
REGION                    1..18
                          note = MISC_FEATURE - Signal Peptide
REGION                    19..24
                          note = MISC_FEATURE - Propeptide
REGION                    25..609
                          note = MISC_FEATURE - Serum Albumin
source                    1..609
                          mol_type = protein
                          organism = Homo sapiens
SEQUENCE: 5
MKWVTFISLL FLFSSAYSRG VFRRDAHKSE VAHRFKDLGE ENFKALVLIA FAQYLQQCPF   60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ RLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVESKDVC KNYAEAKDVF LGMFLYEYAR  360
RHPDYSVVLL LRLAKTYETT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDYLSVV  480
LNQLCVLHEK TPVSDRVTKC CTESLVNRRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASQAALGL                                                         609

SEQ ID NO: 6              moltype = AA  length = 18
FEATURE                   Location/Qualifiers
source                    1..18
                          mol_type = protein
                          organism = Homo sapiens
SEQUENCE: 6
MKWVTFISLL FLFSSAYS                                                18

SEQ ID NO: 7              moltype = AA  length = 6
FEATURE                   Location/Qualifiers
source                    1..6
                          mol_type = protein
                          organism = Homo sapiens
SEQUENCE: 7
RGVFRR                                                             6

SEQ ID NO: 8              moltype = AA  length = 585
FEATURE                   Location/Qualifiers
source                    1..585
                          mol_type = protein
                          organism = Homo sapiens
SEQUENCE: 8
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                 585

SEQ ID NO: 9              moltype = DNA  length = 1827
FEATURE                   Location/Qualifiers
misc_feature              1..72
                          note = Signal Peptide
misc_feature              73..90
                          note = Propeptide
misc_feature              91..1824
                          note = Serum Albumin
source                    1..1827
                          mol_type = other DNA
                          organism = Mus musculus
SEQUENCE: 9
atgaagtggg taaccttct cctcctcctc ttcgtctccg gctctgcttt tccaggggt    60
gtgtttcgcc gagaagcaca caagagtgag atcgcccatc ggtataatga tttgggagaa  120
caacatttca aaggcctagt cctgattgcc ttttcccagt atctccagaa atgctcatac  180
gatgagcatg ccaaattagt gcaggaagta acagactttg caaagacgtg tgttgccgat  240
gagtctgccg ccaactgtga caaatcccct cacactcttt ttggagataa gttgtgtgcc  300
attccaaacc tccgtgaaaa ctatggtgaa ctggctgact gctgtacaaa acaagagccc  360
gaaagaaacg aatgttttcct gcaacacaaa gatgacaacc ccagcctgcc accatttgaa  420
aggccagagg ctgaggccat gtgcacctcc tttaaggaaa acccaaccac ctttatggga  480
cactatttgc atgaagttgc cagaagacat ccttatttct atgccccaga acttctttac  540
```

```
tatgctgagc agtacaatga gattctgacc cagtgttgtg cagaggctga caaggaaagc    600
tgcctgaccc cgaagcttga tggtgtgaag gagaaagcat tggtctcatc tgtccgtcag    660
agaatgaagt gctccagtat gcagaagttt ggagagagag cttttaaagc atgggcagta    720
gctcgtctga gccagacatt ccccaatgct gactttgcag aaatcaccaa attggcaaca    780
gacctgacca aagtcaacaa ggagtgctgc catggtgacc tgctgaaatg cgcagatgac    840
agggcggaac ttgccaagta catgtgtgaa aaccaggcga ctatctccag caaactgcag    900
acttgctgcg ataaaccact gttgaagaaa gcccactgtc ttagtgaggt ggagcatgac    960
accatgcctg ctgatctgcc tgccattgct gctgattttg ttgaggacca ggaagtgtgc   1020
aagaactatg ctgaggccaa ggatgtcttc ctgggcacgt tcttgtatga atattcaaga   1080
agacaccctg attactctgt atccctgttg ctgagacttg ctaagaaata tgaagccact   1140
ctggaaaagt gctgcgctga agccaatcct cccgcatgct acggcacagt gcttgctgaa   1200
tttcagcctc ttgtagaaga gcctaagaac ttggtcaaaa ccaactgtga tctttacgag   1260
aagcttggag aatatggatt ccaaaatgcc attctagttc gctacaccca gaaagcacct   1320
caggtgtcaa ccccaactct cgtggaggct gcaagaaacc taggaagagt gggcaccaag   1380
tgttgtacac ttcctgaaga tcagagactg ccttgtgtgg aagactatct gtctgcaatc   1440
ctgaaccgtg tgtgtctgct gcatgagaag accccagtga gtgagcatgt taccaagtgc   1500
tgtagtggat ccctggtgga aaggcggcca tgcttctctg ctctgacagt tgatgaaaca   1560
tatgtcccca aagagtttaa agctgagacc ttcacctttc actctgatat ctgcacactt   1620
ccagagaagg agaagcagat taagaaacaa acggctcttg ctgagctggt gaagcacaag   1680
cccaaggcta cagcggagca actgaagact gtcatggatg actttgcaca gttcctggat   1740
acatgttgca aggctgctga caaggacacc tgcttctcga ctgagggtcc aaaccttgtc   1800
actagatgca aagacgcctt agcctaa                                       1827

SEQ ID NO: 10           moltype = DNA   length = 72
FEATURE                 Location/Qualifiers
source                  1..72
                        mol_type = other DNA
                        organism = Mus musculus
SEQUENCE: 10
atgaagtggg taacctttct cctcctcctc ttcgtctccg gctctgcttt ttccaggggt    60
gtgtttcgcc ga                                                       72

SEQ ID NO: 11           moltype = DNA   length = 18
FEATURE                 Location/Qualifiers
source                  1..18
                        mol_type = other DNA
                        organism = Mus musculus
SEQUENCE: 11
gaagcacaca agagtgag                                                  18

SEQ ID NO: 12           moltype = DNA   length = 1734
FEATURE                 Location/Qualifiers
source                  1..1734
                        mol_type = other DNA
                        organism = Mus musculus
SEQUENCE: 12
atcgcccatc ggtataatga tttgggagaa caacatttca aaggcctagt cctgattgcc    60
tttttccagt atctccagaa atgctcatac gatgagcatg ccaaattagt gcaggaagta   120
acagactttg caaagacgtg tgttgccgat gagtctgccg ccaactgtga caaatccctt   180
cacactcttt ttgagataaa gttgtgtgcc attccaaacc tccgtgaaaa ctatggtgaa   240
ctggctgact gctgtacaaa acaagagccc gaaagaaacg aatgtttcct gcaacacaaa   300
gatgacaacc ccagcctgcc accatttgaa aggccagagg ctgaggccat gtgcacctcc   360
tttaaggaaa acccaaccac ctttatggga cactatttgc atgaagttgc cagaagacat   420
ccttatttct atgccccaga acttctttac tatgctgagc agtacaatga gattctgacc   480
cagtgttgtg cagaggctga caaggaaagc tgcctgaccc cgaagcttga tggtgtgaag   540
gagaaagcat tggtctcatc tgtccgtcag agaatgaagt gctccagtat gcagaagttt   600
ggagagagag cttttaaagc atgggcagta gctcgtctga gccagacatt ccccaatgct   660
gactttgcag aaatcaccaa attggcaaca gacctgacca aagtcaacaa ggagtgctgc   720
catggtgacc tgctgaaatg cgcagatgac agggcggaac ttgccaagta catgtgtgaa   780
aaccaggcga ctatctccag caaactgcag acttgctgcg ataaaccact gttgaagaaa   840
gcccactgtc ttagtgaggt ggagcatgac accatgcctg ctgatctgcc tgccattgct   900
gctgattttg ttgaggacca ggaagtgtgc aagaactatg ctgaggccaa ggatgtcttc   960
ctgggcacgt tcttgtatga atattcaaga agacaccctg attactctgt atccctgttg  1020
ctgagacttg ctaagaaata tgaagccact ctggaaaagt gctgcgctga agccaatcct  1080
cccgcatgct acggcacagt gcttgctgaa tttcagcctc ttgtagaaga gcctaagaac  1140
ttggtcaaaa ccaactgtga tctttacgag aagcttggag aatatggatt ccaaaatgcc  1200
attctagttc gctacaccca gaaagcacct caggtgtcaa ccccaactct cgtggaggct  1260
gcaagaaacc taggaagagt gggcaccaag tgttgtacac ttcctgaaga tcagagactg  1320
ccttgtgtgg aagactatct gtctgcaatc ctgaaccgtg tgtgtctgct gcatgagaag  1380
accccagtga gtgagcatgt taccaagtgc tgtagtggat ccctggtgga aaggcggcca  1440
tgcttctctg ctctgacagt tgatgaaaca tatgtcccca aagagtttaa agctgagacc  1500
ttcacctttc actctgatat ctgcacactt ccagagaagg agaagcagat taagaaacaa  1560
acggctcttg ctgagctggt gaagcacaag cccaaggcta cagcggagca actgaagact  1620
gtcatggatg actttgcaca gttcctggat acatgttgca aggctgctga caaggacacc  1680
tgcttctcga ctgagggtcc aaaccttgtc actagatgca aagacgcctt agcc        1734

SEQ ID NO: 13           moltype = DNA   length = 1830
FEATURE                 Location/Qualifiers
misc_feature            1..72
```

|  | note = Signal Peptide |  |
| --- | --- | --- |
| misc_feature | 73..90 |  |
|  | note = Propeptide |  |
| misc_feature | 91..1827 |  |
|  | note = Serum albumin |  |
| source | 1..1830 |  |
|  | mol_type = other DNA |  |
|  | organism = Homo sapiens |  |

SEQUENCE: 13

```
atgaagtggg taacctttat ttcccttctt tttctcttta gctcggctta ttccaggggt   60
gtgtttcgtc gagatgcaca caagagtgag gttgctcatc ggtttaaaga tttgggagaa  120
gaaaatttca aagccttggt gttgattgcc tttgctcagt atcttcagca gtgtccattt  180
gaagatcatg taaaattagt gaatgaagta actgaatttg caaaaacatg tgttgctgat  240
gagtcagctg aaaattgtga caaatcactt cataccctt ttggagacaa attatgcaca  300
gttgcaactc ttcgtgaaac ctatggtgaa atggctgact gctgtgcaaa acaagaacct  360
gagagaaatg aatgcttctt gcaacacaaa gatgacaacc caaacctccc ccgattggtg  420
agaccagagg ttgatgtgat gtgcactgct tttcatgaca atgaagagac attttttgaaa  480
aaatacttat atgaaattgc cagaagacat ccttactttt atgccccgga actccttttc  540
tttgctaaaa ggtataaagc tgcttttaca gaatgttgcc aagctgctga taaagctgcc  600
tgcctgttgc caaagctcga tgaacttcgg gatgaaggga aggcttcgtc tgccaaacag  660
agactcaagt gtgccagtct ccaaaaattt ggagaaagag ctttcaaagc atgggcagta  720
gctcgcctga gccagagatt tcccaaagct gagtttgcaa agtttccaa gttagtgaca  780
gatcttacca aagtccacac ggaatgctgc catggagatc tgcttgaatg tgctgatgac  840
agggcggacc ttgccaagta tatctgtgaa aatcaagatt cgatctccag taaactgaag  900
gaatgctgtg aaaaacctct gttggaaaaa tcccactgca ttgccgaagt ggaaaatgat  960
gagatgcctg ctgacttgcc ttcattagct gctgattttg ttgaaagtaa ggatgtttgc 1020
aaaaactatg ctgaggcaaa ggatgtcttc ctgggcatgt ttttgtatga atatgcaaga 1080
aggcatcctg attactctgt cgtgctgctg ctgagacttg ccaagacata tgaaaccact 1140
ctagagaagt gctgtgccgc tgcagatcct catgaatgct atgccaaagt gttcgatgaa 1200
tttaaaccte ttgtggaaga gcctcagaat ttaatcaaac aaaattgtga gcttttttgag 1260
cagcttggag agtacaaatt ccagaatgcg ctattagttc gttacaccaa gaaagtaccc 1320
caagtgtcaa ctccaactct gtagaggtc tcaagaaacc taggaaaagt gggcagcaaa 1380
tgttgtaaac atcctgaagc aaaaagaatg ccctgtgcag aagactatct atccgtggtc 1440
ctgaaccagt tatgtgtgtt gcatgaaaaa acgccagtaa gtgacagagt caccaaatgc 1500
tgcacagaat ccttggtgaa caggcgacca tgcttttcag ctctggaagt cgatgaaaca 1560
tacgttccca aagagtttaa tgctgaaaca ttcaccttcc atgcagatat atgcacactt 1620
tctgagaagg agagacaaat caagaaacaa actgcacttg ttgagctcgt gaaacacaag 1680
cccaaggcaa caaaagagca actgaaagct gttatggatg atttcgcagc ttttgtagag 1740
aagtgctgca aggctgacga taaggagacc tgctttgccg aggagggtaa aaaacttgtt 1800
gctgcaagtc aagctgcctt aggcttataa                                   1830
```

| SEQ ID NO: 14 | moltype = DNA length = 72 |
| --- | --- |
| FEATURE | Location/Qualifiers |
| source | 1..72 |
|  | mol_type = other DNA |
|  | organism = Homo sapiens |

SEQUENCE: 14

```
atgaagtggg taacctttat ttcccttctt tttctcttta gctcggctta ttccaggggt   60
gtgtttcgtc ga                                                       72
```

| SEQ ID NO: 15 | moltype = DNA length = 18 |
| --- | --- |
| FEATURE | Location/Qualifiers |
| source | 1..18 |
|  | mol_type = other DNA |
|  | organism = Homo sapiens |

SEQUENCE: 15

```
gatgcacaca agagtgag                                                 18
```

| SEQ ID NO: 16 | moltype = DNA length = 1737 |
| --- | --- |
| FEATURE | Location/Qualifiers |
| source | 1..1737 |
|  | mol_type = other DNA |
|  | organism = Homo sapiens |

SEQUENCE: 16

```
gttgctcatc ggtttaaaga tttgggagaa gaaaatttca aagccttggt gttgattgcc   60
tttgctcagt atcttcagca gtgtccattt gaagatcatg taaaattagt gaatgaagta  120
actgaatttg caaaaacatg tgttgctgat gagtcagctg aaaattgtga caaatcactt  180
catacccttt ttggagacaa attatgcaca gttgcaactc ttcgtgaaac ctatggtgaa  240
atggctgact gctgtgcaaa acaagaacct gagagaaatg aatgcttctt gcaacacaaa  300
gatgacaacc caaacctccc ccgattggtg agaccagagg ttgatgtgat gtgcactgct  360
tttcatgaca atgaagagac attttttgaaa aaatacttat atgaaattgc cagaagacat  420
ccttactttt atgccccgga actccttttc tttgctaaaa ggtataaagc tgcttttaca  480
gaatgttgcc aagctgctga taaagctgcc tgcctgttgc caaagctcga tgaacttcgg  540
gatgaaggga aggcttcgtc tgccaaacag agactcaagt gtgccagtct ccaaaaattt  600
ggagaaagag ctttcaaagc atgggcagta gctcgcctga gccagagatt tcccaaagct  660
gagtttgcaa agtttccaa gttagtgaca gatcttacca aagtccacac ggaatgctgc  720
catggagatc tgcttgaatg tgctgatgac agggcggacc ttgccaagta tatctgtgaa  780
aatcaagatt cgatctccag taaactgaag gaatgctgtg aaaaacctct gttggaaaaa  840
tcccactgca ttgccgaagt ggaaaatgat gagatgcctg ctgacttgcc ttcattagct  900
```

```
gctgattttg ttgaaagtaa ggatgtttgc aaaaactatg ctgaggcaaa ggatgtcttc    960
ctgggcatgt ttttgtatga atatgcaaga aggcatcctg attactctgt cgtgctgctg   1020
ctgagacttg ccaagacata tgaaaccact ctagagaagt gctgtgccgc tgcagatcct   1080
catgaatgct atgccaaagt gttcgatgaa tttaaacctc ttgtggaaga gcctcagaat   1140
ttaatcaaac aaaattgtga gcttttttgag cagcttggag agtacaaaatt ccagaatgcg   1200
ctattagttc gttacaccaa gaaagtaccc caagtgtcaa ctccaactct tgtagaggtc   1260
tcaagaaacc taggaaaagt gggcagcaaa tgttgtaaac atcctgaagc aaaaagaatg   1320
ccctgtgcag aagactatct atccgtggtc ctgaaccagt tatgtgtgtt gcatgagaaa   1380
acgccagtaa gtgacagagt caccaaatgc tgcacagaat ccttggtgaa caggcgacca   1440
tgcttttcag ctctggaagt cgatgaaaca tacgttccca aagagtttaa tgctgaaaca   1500
ttcaccttcc atgcagatat atgcacactt tctgagaagg agagacaaat caagaaacaa   1560
actgcacttg ttgagctcgt gaaacacaag cccaaggcaa caaaagagca actgaaagct   1620
gttatggatg atttcgcagc ttttgtagag aagtgctgca aggctgacga taaggagacc   1680
tgctttgccg aggagggtaa aaaacttgtt gctgcaagtc aagctgcctt aggctta      1737

SEQ ID NO: 17          moltype = DNA   length = 23484
FEATURE                Location/Qualifiers
misc_feature           1..23484
                       note = Synthetic
misc_feature           1..46
                       note = Mouse Sequence
misc_feature           47..17381
                       note = Human Sequence
misc_feature           17382..17387
                       note = XhoI
misc_feature           17388..17421
                       note = LoxP
misc_feature           17422..18108
                       note = Prm1
misc_feature           18109..19249
                       note = Crei
misc_feature           19250..19545
                       note = SV40 PolyA
misc_feature           19546..20758
                       note = hUbi
misc_feature           20759..20825
                       note = em7
misc_feature           20826..21629
                       note = Neo
misc_feature           21630..22119
                       note = PGK PolyA
misc_feature           22120..22153
                       note = LoxP
misc_feature           22160..22185
                       note = I-CeuI
misc_feature           22186..22191
                       note = NheI
misc_feature           22192..23484
                       note = Mouse Sequence
source                 1..23484
                       mol_type = other DNA
                       organism = synthetic construct
SEQUENCE: 17
tgcacacaga tcacctttcc tatcaacccc actagcctct ggcaaaatga agtgggtaac     60
cttttattcc cttcttttc tcttttagctc ggcttattca aggggtgtgt ttcgtcgaga    120
tgcacgtaag aaatccattt ttctattgtt caacttttat tctattttcc cagtaaaata    180
aagttttagt aaaactctgca tctttaaaga attattttgg catttattc taaaatggca    240
tagtattttg tatttgtgaa gtcttacaag gttatcttat taataaaatt caaacatcct    300
aggtaaaaaa aaaaaaaggt cagaattgtt tagtgactgt aatttctctt tgcgcactaa    360
ggaaagtgca aagtaactta gagtgactga aacttcacag aatagggttg aagattgaat    420
tcataactat cccaaagacc tatccattgc actatgcttt atttaaaaac cacaaaacct    480
gtgctgttga tctcataaat agaacttgta tttatattta ttttcatttt agtctgtctt    540
cttggttgct gttgatagac actaaaagag tattagatat tatctaagtt tgaatataag    600
gctataaata tttaataatt tttaaaatag tattcttggt aattgaatta ttcttctgtt    660
taaaggcaga agaaataatt gaacatcatc ctgagttttt ctgtaggaat cagagcccaa    720
tatttgaaaa caaatgcata atctaagtca atggaaaga aatataaaaa gtaacattat    780
tacttcttgt tttcttcagt atttaacaat ccttttttt cttcccttgc ccagacaaga    840
gtgaggttgc tcatcggttt aaagatttgg gagaagaaaa tttcaaagcc ttgtaagtta    900
aaatattgat gaatcaaatt taatgtttct aatagttgtg tttaaagatc taaagtgctt    960
atatttcctt gtcatcaggg ttcagattct aaaacagtgc tgcctcgtag agttttctgc   1020
gttgaggaag atattctgta tctgggctat ccaataaggt agtcactggt cacatggcta   1080
ttgagtactt caaatatgac aagtgcaact gagaaacaaa aacttaaatt gtatttaatt   1140
gtagttaatt tgaatgtata tagtcacatg tggctaatgg ctactgtatt ggacagtaca   1200
gctctggaac ttgcttggtg gaaaggactt taatataagt ttccttggt ggcttaccca   1260
ctaaatcttc tttacatagc aagcattcct gtgcttagtt gggaatattt aattttttt   1320
ttttttttaag acagggtctc gctctgtcgc ccaggctgga gtgcagtggc gcaatctcgg   1380
ctcactgcaa actccgcctc ccgggttcac gccattctcc tgcctcagcc tcccgagtag   1440
ctgggactac aggcgcccgc catcacgccc ggctaatctt ttgtatttttt agtagagatg   1500
ggtttcacc gtgtgccagg atggtctcaa tctcctgaca tcgtgatctg cccacctcgg   1560
```

```
cctcccaaag tgctgggatt acaggagtga gccaccgcgc ccggcctatt taaatgtttt   1620
ttaatctagt aaaaaatgag aaaattgttt ttttaaaagt ctacctaatc ctacaggcta   1680
attaaagacg tgtgtgggga tcaggtgcgg tggttcacac ctgtaatccc agcactttgg   1740
aaggctgatg caggaggatt gcttgagccc aggagttcaa gaccagcctg ggcaagtctc   1800
tttaaaaaaa acaaaacaaa caaacaaaaa aattaggcat ggtggcacat gcctgtagtc   1860
ctagctactt aggaggctga cgtaggagga tcgtttggac ctgagaggtc aaggctacag   1920
tgagccatga ttgtgccact gcactccagc ctgggtgaca gagtgagact ctgtctcaaa   1980
aaagaaaaag gaaatctgtg gggtttgttt tagttttaag taattctaag gactttaaaa   2040
atgcctagtc ttgacaatta gatctatttg gcatacaatt tgcttgctta atctatgtgt   2100
gtgcatagat ctactgacac acgcatacat ataaacatta gggaactacc attctctttg   2160
cgtaggaagc cacatatgcc tatctaggcc tcagatcata cctgatatga ataggctttc   2220
tggataatgg tgaagaagat gtataaaaga tagaacctat acccatacat gatttgttct   2280
ctagcgtagc aacctgttac atattaaagt tttattatac tacattttc tacatccttt    2340
gtttcagggt gttgattgcc tttgctcagt atcttcagca gtgtccattt gaagatcatg   2400
taaaattagt gaatgaagta actgaatttg caaaaacatg tgttgctgat gagtcagctg   2460
aaaattgtga caaatcactt gtaagtacat tctaattgtg gagattcttt cttctgtttg   2520
aagtaatccc aagcatttca aaggaatttt ttttaagttt tctcaattat tattaagtgt   2580
cctgatttgt aagaaacact aaaaagttgc tcatagactg ataagccatt gtttctttg    2640
tgatagagat gctttagcta tgtccacagt tttaaaatca tttctttatt gagaccaaac   2700
acaacagtca tggtgtattt aaatggcaat tgtcattta taaacacctc tttttaaaat    2760
ttgaggtttg gtttcttttt gtagaggcta ataggatat gatagcatgt atttatttat    2820
ttatttatct tattttatta tagtaagaac ccttaacatg adatctaccc tgttatattt    2880
ttaagtgtac aatccattat tgttaactac gggtacactg ttgtatagct tactcatctt   2940
gctgtattaa aactttgtgc ccattgatta gtaaccctc gtttcgtcct cccccagcca    3000
ctggcaacca gcattatact ctttgattct atgagtttga ctactttagc taccttatat   3060
aagtggtatt atgtactgtt tatctttta tgactgacct attcccta gcatagtgca     3120
ttcaaagtcc aaccatgttg ttgcctattg cagaatttcc ttctttcaa ggctgaataa   3180
tattccagtg catgtgtgta ccacattttc tttatccatt aatttgttga ttgatagaca   3240
tttaggttgg ttttctacat cttgactatc atgaatagtt ttgcaatgaa cacaggagag   3300
ctactatctc ttagagatga tatcatggtt tttatcatca gaaaacaccc actgatttct   3360
atgctaattt tgttacctgg gtggaataat agtacagcta tatattcctc atttagata    3420
tctttgtatt tctacataca ataaaaaagc agagtactta gtcatgttga agaactttaa   3480
acttttagta tttccagatc aatcttcaaa acaaggacag gtttatcttt ctctcaccac   3540
tcaatctata tatacctctt gtgggcaagg ccagtttta tcactggagc cttccccttt    3600
tttattatgt acctctccct cacagcagag tcaggacttt aacttacac aatactatgg    3660
ctctacatat gaaatcttaa aaatacataa aaattaataa attctgtcta gagtagtata   3720
ttttccctgg ggtacagtt actttcataa taaaaattag agataaggaa aggactcatt    3780
tattggaaag tgattttagg taacatttct ggaagaaaaa tgtcatatatc ttaatagtca   3840
cttaatatat gatggattgt gttactcctc agttttcaat ggcatatact aaaacatggc   3900
cctctaaaaa gggggcaaat gaaatgagaa actctctgaa tgtttttctc ccctaggtga   3960
attcacctgc tgcttagaag cttattttct cttgatttct gttataatga ttgctcttac   4020
cctttagttt taagtttcaa aataggagtc atataacttt ccttaaagct attgactgtc   4080
tttttgtcct gtttttattca ccatgagtta tagtgtgaca gttaattctt atgaaaatta   4140
tatagagatg gttaaatcat cagaaactgt aaacctcgat tgggagggga agcggatttt   4200
taaatgattt cctgaccaag cttaaccagt atattaaatc ctttgtactg ttcttttggct   4260
ataaagaaaa aaggtactgt ccagcaactg aaacctgctt tcttccattt agcatacccet  4320
ttttggagac aaattatgca cagttgcaac tcttcgtgaa acctatggtg aaatggctga   4380
ctgctgtgca aaacaagaac ctgagagaaa tgaatgcttc ttgcaacaca aagatgacaa   4440
cccaaacctc ccccgattgg tgagaccaga ggttgatgtg atgtgcactg cttttcatga   4500
caatgaagag acatttttga aaaagtaagt aatcagatgt ttatagttca aaattaaaaa   4560
gcatggagta actccatagg ccaacactct ataaaaatta ccataacaaa aatattttca   4620
acattaagac ttggaagttt tgttatgatg atttttaaa gaagtagtat ttgataccac    4680
aaaattctac acagcaaaaa atatgatcaa agatattttg aagtttattg aaacaggata   4740
caatcttct gaaaattta agatagacaa attatttaat gtattacgaa gatatgtata    4800
tatggtttgtt ataattgatt tcgttttagt cagcaacatt atattgccaa aatttaacca   4860
tttatgcaca cacacacaca cacacacaca cttaaccctt ttttccacat acttaaagaa   4920
tgacagagac aagaccatca tgtgcaaatt gagcttaatt ggttaattag atatctttgg   4980
aatttggagg ttctggggag aatgtcgatt acaattattt ctgtaatatt gtctgctata   5040
gaaaagtgac tgtttttctt tttcaaaatt tagatactta tatgaaattg ccagaagaca   5100
tccttacttt tatgcccggg aactcctttt ctttgctaaa aggtataaag ctgcttttac   5160
agaatgttgc caagctgctg ataaagctgc ctgcctgttg ccaaaggtat tatgcaaaag   5220
aatagaaaaa aagagttcat tatccaacct gattttgtcc attttgtggc tagatttagg   5280
gaacctgagt gtctgataca aactttccga catggtcaaa aaagccttcc tttatctgt    5340
cttgaaaatc tttcatcttt gaaggcctac atctctcgtt cttcttttaa gatttgccaa   5400
tgatgatctg tcagaggtaa tcactgtgca tgtgtttaaa gatttcacca cttttttatgt   5460
tggtgatcac tatagtgaaa tactgaaact tgtttgtcaa attgcacagc aaggggccac   5520
agttcttgtt tatcttttca tgataatttt tagtagggag ggaattcaaa gtagagaatt   5580
ttactgcatc tagatgcctg agttcatgca ttcattccat aaatatatat tatggaatgc   5640
tttattttct tttctgagga gtttactgat gttggtggag gagagactga aatgaattat   5700
acacaaaatt taaaaattag caaaattgca gcccctggga tattagcgta ctctttctct   5760
gacttttctc ccactttaa ggctctttt cctggcaatg tttccagttg gtttctaact     5820
acataggaa ttccgctgtg accagaatga tcgaatgatc tttcctttc ttagagca       5880
aaatcattat tcgctaaagg gagtacttgg gaatttaggc ataaattatg ccttcaaaat   5940
ttaatttggc acagtctcat ctgagcttat ggaggggtgt ttcatgtaga attttcttc    6000
taattttcat caaattattc cttttttgtag ctcgatgaac ttcgggatga agggaaggct   6060
tcgtctgcca aacagagact caagtgtgcc agtctccaaa aatttggaga aagagctttc   6120
aaagcatggt aaatactttt aaacatagtt ggcatctttta taacgatgta aatgataatg   6180
cttcagtgac aaattgtaca ttttttatgta ttttgcaaag tgctgtcaaa tacatttctt   6240
tggttgtcta acaggtagaa ctctaataga ggtaaaaatc agaatatcaa tgacaatttg   6300
```

```
acattatttt taatctttc ttttctaaat agttgaataa tttagaggac gctgtccttt   6360
ttgtcctaaa aaaagggaca gatatttaag ttctatttat ttataaaatc ttggactctt   6420
attctaatgg ttcattattt ttatagagct gtaggcatgg ttctttattt aattttttaa   6480
agttattttt aattttgtg gatacagagt aggtatacat atttacgggg tatatgagat   6540
attttgatat aagtatacaa catatataat ccctttattt aatttatct tccccccaat    6600
gatctaaaac tatttgcttg tccttttatg tcttatagtt aaattcagtc accaactaag   6660
ttgaagttac ttcttatttt tgcatagctc cagctctgat cttcatctca tgttttgcc    6720
tgagcctctg ttttcatatt acttagttgg ttctgggagc atactttaat agccgagtca   6780
agaaaaatac tagctgcccc gtcacccaca ctcctcacct gctagtcaac agcaaatcaa   6840
cacaacagga aataaaatga aaataatgaa cattatgcat gctctctaga aactgtcaat   6900
tgaactgtat ttgctcatca ttcctaccat ctacaccacc aaaatcaacc aaatttatga   6960
aaaaaaacag ccccaacata aaattataca cagataaaca ggctatgatt ggttttggga   7020
aagaagtcac ctttacctga tttaggcaac tgtgaaatga ctagagaatg aagaaaatta   7080
gacgtttaca tcttgtcata gagtttgaag atagtgctgg atctttcttt ttataagtaa   7140
gatcaataaa aactccctca ttctgtagaa gttatgattt cttttctaag agacctttag   7200
aagtcagaaa aaatgtgttt caattgagaa aaaagataac tggagtttgt gtagtacttc   7260
ccagattata aaatgctttt gtatgtatta tctaatttaa tcctcaaaac ttcttcaatt   7320
tagcatgttg tcatgacact gcagaggctg aagctcagag aggctgagcc ctctgctaac   7380
aagtcctact gctaacaagt gataaagcca gagctggaag tcacatctgg actccaaacc   7440
tgatgcttct cagcctgttg cccctttag agttccttt taatttctgc ttttatgact     7500
tgctagattt ctacctacca cacacactct taaatggata attctgccct aaggataagt   7560
gattacatt tggttcagaa ctagaactaa tgaatttaa aaattatttc tgtatgtcca     7620
ttttgaattt tcttatgaga aatagtattt gcctagtgtt ttcatataaa atatcgcatg   7680
ataataccat tttgattggc gattttcttt ttagggcagt agctcgcctg agccagagat   7740
ttcccaaagc tgagtttgca gaagtttcca agttagtgac agatcttacc aaagtccaca   7800
cggaatgctg ccatggagat ctgcttgaat gtgctgatga cagggtaaag agtcgtcgat   7860
atgctttttg gtagcttgca tgctcaagtt ggtagaatgg atgcgtttgg tatcattggt   7920
gatagctgac agtgggttga gattgtcttc tgtgctttcg tctgtcctat cttcaatctt   7980
tccctgccta tggtggtggt acctttctgt ttttaacctg gctataaatt accagataaa   8040
cccattcact gatttgtaac tccttcagt catgctctaa ctgtaaatga aggcttaaac    8100
tgaagtagaa cagttacaag gttttacttg gcaaacatc ttgcaaggta gatgtctaag    8160
aagattttt tttctttttt taagacagag tttcgctctt gtttcccagg ctggggtgca    8220
atggtgtgat cttggctcag cgcaacctct gcctcctggg ttcaagtgat tctcatgcct   8280
cagcctccca agtagctggg attacaggca tgcgccacca cacctggcta atttttgtatt  8340
tttagtagag gcgggggtttc accatattgt ccagactggt ctcgaactcc tgacctcagg  8400
tgatccaccc gccttggcct cccaaagtgc tgggattaca ggcatgagcc accttgccca   8460
gcctaagaag attttttgag ggaggtaggt ggacttggag aaggtcacta cttgaagaga   8520
tttttggaaa tgatgtattt ttcttctcta tattccttcc cttaattaac tctgtttgtt   8580
agatgtgcaa atatttggaa tgatatctct tttctcaaaa cttataaaat tttctttctc   8640
cctttcttca agattaaact tatgggcaaa tactagaatc ctaatctctc atggcacttt   8700
ctggaaaatt taaggcggtt atttatata tgtaagcagg gcctatgact atgatcttga    8760
ctcattttc aaaaatcttc tatatttat ttagttattt ggtttcaaaa ggcctgcact     8820
taattttggg ggattatttg gaaaaacagc attgagtttt aatgaaaaaa acttaaatgc   8880
cctaacagta gaaacataaa attaataaat aactgagctg agcacctgct actgattagt   8940
ctattttaat taagtgggaa tgttttttgta gtcctatcta catctccagg tttaggagca  9000
aacagagtat gttcatagaa ggaatatgtg tatggtctta gaatacaatg aatatgttct   9060
gccaacttaa taaaggtctg aggagaaagt gtagcaatgt caattcgtgt tgaacaattt   9120
ccaccaactt acttataggc ggaccttgcc aagtatatct gtgaaaatca agattcgatc   9180
tccagtaaac tgaaggaatg ctgtgaaaaa cctctgttgg aaaaatccca ctgcattgcc   9240
gaagtggaaa atgatgagat gcctgctgac ttgccttcat tagctgctga ttttgttgaa   9300
agtaaggata tttttgcaaaaa ctatgctgag gcaaaggatg tcttcctggg catgtaagta  9360
gataagaaat tattcttta tagctttggc atgacctcac aacttaggag gatagcctag    9420
gcttttctgt ggagttgcta caattccct gctgcccaga atgtttcttc atccttccct    9480
ttcccaggct ttaacaattt ttgaaatagt taattagttg aatacattgt cataaaataa   9540
tacatgttca tggcaaagct caacattcct tactccttag gggtatttct gaaaatacgt   9600
ctagaaacat tttgtgtata tataaattat gtatacttca gtcattcatt ccaagtgtat   9660
ttcttgaaca tctataatat atgtgtgtga ctatgtattg cctgtctatc taactaatct   9720
aatctaatct agtctatcta tctaatctat gcaatgatag caaagaagta taaaagaaa    9780
tatagagtct gacaccaggt gcttttatt tggtgaaaag accagaagtt cagtataatg    9840
gcaatatggt aggcaactca attacaaat aaatgtttac atattgtcag aagttgtggt    9900
gataaactgc attttgttg ttggattatg ataatgcact aaataatatt tcctaaaatt    9960
atgtaccta caagatttca ctcatacaga gaagaaagag aatattttaa gaacatatct    10020
ctgcccatct atttatcaga atcctttga gatgtagttt aaatcaaaca aaatgttaat    10080
aaaaataaca agtatcattc atcaaagact tcatatgtgc caagcagtgt gtgctttgca   10140
tagattatgt catatagttc tcataatcca ccttccgaga cagatactat ttatttttg    10200
agacagagtt ttactcttgt tgcccaggct ggagtgcaat ggtgccatct cggctcacca   10260
caacctccgc ctcccaggtt caagcgattc tcctgcctca gcctcctggg attacaggca   10320
tgcaccacca tgcctggcta attttgtatt tttagtagag atgggggtttc accatgttgg  10380
tcagactggt ctcaaactcc tgacctctgt tgatatgcct gcctcagcct cctaaagtgc   10440
tgggattaca ggcatgagcc actgtgccca gccgacagat actattatta tttccattct   10500
accgagaagg agactaaggc tctgatcatt taaataagtt gcctaaggtg atgcagtgat   10560
ataagtagca gagctaggaa ttgagccttg gtaacttaa ctctgacccc caagtcctta    10620
gctactaagc tttactgcat ggggtttagt caaattaaga cttttggaat atgagttact   10680
ttgagatta gcttttgtgat attttttgtg ctcatttgtc caacaaagtc tattttattt   10740
tcatcttaat taggttttg tatgaatatg caagaaggca tcctgattac tctgtcgtgc   10800
tgctgctgag acttgccaag acatatgaaa ccactctaga gaagtgctgt gccgctgcag   10860
atcctcatga atgctatgcc aaagtggtag gtttattgtt ggaaaaaaat gtagttcttt   10920
gactgatgat tccaataatg agaaagaaaa ataatgcaag aatgtaaaat gatatacagt   10980
gcaatttaga tcttttcttg agatggtttc aattctggaa tcttaaacat gaagaaaaa    11040
```

```
gtagccttag aatgattaac aaaatttaga ctagttagaa tagaaagatc tgaatagagc  11100
aatctctaaa aaattttgat cttttttct cttttcaca atcctgagaa caaaaaaaa    11160
ttaaatttaa atgttaatta gaagatattt aactagatg taaagtgagt taacctgatt  11220
ccaggattaa tcaagtacta gaattagtat cttatggcaa attatagaac ctatccctt   11280
agaatatttt caaatctttt tgaggatgtt taggaatagt tttacaagaa attaagttag  11340
gagaggaaat ctgttctgga ggatttttag ggttcccact agcatatgta atggtttctg  11400
aactattcag aatcagagaa aactcatttt tcctgctttc aagaagctac tgtatgccag  11460
gcaccatgca caaacaatga ccaacgtaaa atctctcatt ttggagagcc tggaatctaa  11520
ctggaaaggt gaactaataa taataatatg tacaatcata gccatcattt attaaacttt  11580
tattatatgc aaggcactgt ttaatttcat tagcttacct ggtttacaga gcagctctat  11640
gagatgagtg ccatctttgc ccctatttta gggataagga ttctgaaatg tggagatggt  11700
aagtaaaatt gcacaactga agaatgagtt acatgacttg gctcaaatac tggtcattga  11760
actccagagc ctgaatattc ttaaccactt acatgatgca agctcaccaa ataaatagtt  11820
cgaatgtatt gtgacagagc ggcattgata ttcatctatt catgtggctt tgagtaggaa  11880
gaagaaagga tatcattctg accagagggg tgaaaaacaa cctgcatctg atcctgaggc  11940
ataatactat taacacaatt cttttatgtt tcagttcgat gaatttaaac ctcttgtgga  12000
agagcctcag aatttaatca aacaaaattg tgagcttttt gagcagcttg gagagtacaa  12060
attccagaat gcgtaagtaa tttttattga ctgattttt ttatcaattt gtaattattt  12120
aagacttaat atatgagcca cctagcatag aacttttaag aatgaaaata cattgcatat  12180
ttctaatcac tctttgtcaa gaaagatagg agaggagaga taaaatagtt gatggggtgg  12240
agaggtctat atttgaatgt agtctaaaaa ttgttctctt aagattggaa gtatgtaggc  12300
tgggaaggta aataccaaat cttggtatat cagaactgag catgtccctt gaaggttaag  12360
aaatagttaa tgggcaaata gagcatggca atatttgta gagcagcaag tagtaggcct    12420
tgaatagatg tcgctcaaaa agtaaatatgt aagctgaaca caaaaatgta acaaatgaat  12480
ttagatacat atttgaatat taaattcagg ttgtttggga gatgcaccta gtctttgatg  12540
gttaaacctt tccctccata gaagagacag agacagaatg gcttgctgga ctaatgtccc  12600
aattcaatag agtcttatct atgaaggtta aaaacaagaa gagacatatt atacagtaga  12660
tatttattgt gtggctcata cacatggtgc tcttctgatt atggatttta gagataataa  12720
cagtgaacaa gacatagttt cttttcctcga gtagattaaa gtcatacatt gactttaat   12780
ggtgactggc attcttaata catgattatt atatattagg taccatgtca gattaattat  12840
aatactttac tactttaat ttaaccctg aactatccct attgagtcag atatatttcc    12900
ttccatttc tacttgatc tttcaagttt agcatatgct gatacatatg aagctctctc    12960
caggttttat tgaaagaaga aattaataaa tttattaatg tcactgaatt aggcaactca  13020
cttccccaag attatgcaag tggtacaggt ggaactcaaa gccaagttta actagttgtt  13080
caggagaatg ttttctaccc tccactaacc cactactctg cagatggaga taatatgatg  13140
aatggaacat agcaacatct tagttgattc cggccaagtg ttctctgttt tatctactat  13200
gttagacagt ttcttgcctt gctgaaaaca catgacttct tttttcagg ctattagttc   13260
gttacaccaa gaaagtaccc caagtgtcaa ctccaactct tgtagaggtc tcaagaaacc  13320
taggaaaagt gggcagcaaa tgttgtaaac atcctgaagc aaaaagaatg ccctgtgcag  13380
aagactatgt gagtctttaa aaaaaatataa taaattaata atgaaaaaat tttacctta   13440
gatattgata atgctagctt tcataagcag aaggaagtaa tgtgtgtgtg tgcatgtttg  13500
tgtgcatgtg tgtgtcatg cacgtgtgtg tatgtgtgat attggcagtc aaggcccga    13560
ggatgataat ttttttttt tttttgagac ggagtctcgc tttgttgtcc aggctggagt  13620
gcagtggtgc catctcggct cactgcaacc tccgcctccc aggttcaagc cattctcctg  13680
cctcagcctc ccaagtagct gggactacag gtgcatgcca ccatgcctgg ctaatttttt  13740
gtatttttag tagaaaattt tcagcttcac ctctttgaa tttctgctct cctgcctgtt   13800
ctttagctat ccgtggtcct gaaccagtta tgtgtgttgc atgagaaaac gccagtaagt  13860
gacagagtca ccaaatgctg cacagaatcc ttggtgaaca ggcgaccatg cttttcagct  13920
ctggaagtcg atgaaacata cgttcccaaa gagtttaatg ctgaaacatt caccttccat  13980
gcagatatat gcacactttc tgagaaggag agacaaatca agaaacaaac gtgaggagta  14040
tttcattact gcatgtgttt gtagtcttga tgtcaagaac tgtcaattca agctagcaac  14100
tttttcctga agtagtgatt atatttctta gaggaaagta ttggagtgtt gcccttatta  14160
tgctgataag agtacccaga ataaaatgaa taacttttta aagacaaaat cctctgttat  14220
aatattgcta aaattattca gagtaatatt gtggattaaa gccacaatag aataacatgt  14280
taggccatat tcagtagaaa aagatgaaca attaactgat aaatttgtgc acatggcaaa  14340
ttagttaatg ggaaccatag gagaatttat ttctagatgt aaataattat tttaagtttg  14400
ccctatggtg gccccacaca tgagacaaac ccccaagatg tgacttttga gaatgagact  14460
tggataaaaa acatgtagaa atgcaagccc tgaagctcaa ctcccttattg ctatcacagg  14520
ggttataatt gcataaaatt tagctataga aagttgctgt catctcttgt gggctgtaat  14580
catcgtctag gcttaagagt aatattgcaa aacctgtcat gcccacacaa atctctccct  14640
ggcattgttg tctttgcaga tgtcagtgaa agagaaccag cagctcccat gagtttggat  14700
agccttattt tctatagcct ccccactatt agctttgaag ggagcaaagt ttaagaacca  14760
aatataaagt ttctcatctt tatagatgag aaaaattta aataaagtcc aagtaaatta   14820
aatttttaag gatcatttt agctcttaa tagcaataaa actcaatatg acataatatg    14880
gcacttccaa aatctgaata atatatatt gcaatgacat acttcttttc agagatttac   14940
tgaaagaaa tttgttgaca ctacataacg tgatgagtgg tttatactga ttgttttcagt  15000
tggtcttccc accaactcca tgaaagtgga ttttattatc ctcatcatgc agatgagaat  15060
attgagactt atagcggtat gcctgagccc caaagtactc agagttgcct ggctccaaga  15120
tttataatct taaatgatgg gactaccatc cttactctct tcattttct atacgtaagt   15180
aatgtttttt ctgttttttt ttttctttt tccattcaaa ctcagtgcac ttgttgagct  15240
cgtgaaacac aagcccaagg caacaaaaga gcaactgaaa gctgttatgg atgatttcgc  15300
agcttttgta gagaagtgct gcaaggctga cgataaggag acctgctttg ccgaggaggt  15360
actacagttc tcttcatttt aatatgtcca gtattcattt ttgcatgttt ggttaggcta  15420
gggcttaggg atttatatat caaaggaggc tttgacatg tgggacaggg atctttattt   15480
acaaacaatt gtcttacaaa atgaataaaa cagcactttg tttttatctc ctgctctatt  15540
gtgccatact gttaaatgtt tataatgcct gttctgtttc caaatttgtg atgctttatga 15600
atattaatag gaatatttgt aaggcctgaa atatttgat catgaaatca aaacattaat   15660
ttatttaaac atttacttga aatgtggtgg tttgtgattt agttgatttt ataggctagt  15720
gggagaattt acattcaaat gtctaaatca cttaaaattg ccctttatgg cctgacagta  15780
```

```
actttttttt attcatttgg ggacaactat gtccgtgagc ttccgtccag agattatagt   15840
agtaaattgt aattaaagga tatgatgcac gtgaaatcac tttgcaatca tcaatagctt   15900
cataaatgtt aattttgtat cctaatagta atgctaatat tttcctaaca tctgtcatgt   15960
ctttgtgttc agggtaaaaa acttgttgct gcaagtcaag ctgccttagg cttataacat   16020
cacatttaaa agcatctcag gtaactatat tttgaatttt ttaaaaaagt aactataata   16080
gttattatta aaatagcaaa gattgaccat ttccaagagc catatagacc agcaccgacc   16140
actattctaa actatttatg tatgtaaata ttagcttta aaattctcaa aatagttgct   16200
gagttgggaa ccactattat ttctattttg tagatgagaa aatgaagata aacatcaaag   16260
catagattaa gtaattttcc aaagggtcaa aattcaaaat tgaaaccaaa gtttcagtgt   16320
tgcccattgt cctgttctga cttatatgat gcggtacaca gagccatcca agtaagtgat   16380
ggctcagcag tggaatactc tgggaattag gctgaaccac atgaaagagt gctttatagg   16440
gcaaaaacag ttgaatatca gtgatttcac atggttcaac ctaatagttc aactcatcct   16500
ttccattgga gaatatgatg gatctacctt ctgtgaactt tatagtgaag aatctgctat   16560
tacatttcca atttgtcaac atgctgagct ttaatagcac ttatcttctt atgacaacat   16620
ttattggtgt gtccccttgc ctagcccaac agaagaattc agcagccgta agtctaggac   16680
aggcttaaat tgtttcact ggtgtaaatt gcagaaagat gatctaagta atttggcatt   16740
tatttaata ggttttgaaaa acacatgcca ttttacaaat aagacttata tttgtccttt   16800
tgtttttcag cctaccatga gaataagaga aagaaatga agatcaaaag cttattcatc   16860
tgttttttctt tttcgttggt gtaaagccaa caccctgtct aaaaaacata aatttcttta   16920
atcattttgc ctctttttctc tgtgcttcaa ttaataaaaa atggaaagaa tctaatagag   16980
tggtacagca ctgttatttt tcaaagatgt gttgctatcc tgaaaattct gtaggttctg   17040
tggaagttcc agtgttctct cttattccac ttcggtaagg gatttctagt ttcttgtggg   17100
ctaattaaat aaatcattaa tactcttcta agttatggat tataaacatt caaaataata   17160
ttttgacatt atgataattc tgaataaaag aacaaaaacc atggtatagg taaggaatat   17220
aaaacatggc ttttacctta gaaaaacaa ttctaaaatt catatggaat caaaaaagag   17280
cctgcagaac caaagtaaga ctaagcaaaa agaacaaatt acctgatttc aaactacact   17340
ataaggccat agtcaccgaa acagcaaggt actggtataa actcgagata acttcgtata   17400
atgtatgcta tacgaagtta tatgcatgcc agtagcagca cccacgtcca ccttctgtct   17460
agtaatgtcc aacacctccc tcagtccaaa cactgctctg catccatgtg gctcccattt   17520
ataacctgaag cacttgatgg ggcctcaatg ttttactaga gcccacccccc ctgcaactct   17580
gagaccctct ggatttgtct gtcagtgcct cactggggcg ttggataatt tcttaaaagg   17640
tcaagttccc tcagcagcat tctctgagca gtctgaagat gtgtgcttttt cacagttcaa   17700
atccatgtgg ctgtttcacc cacctgcctg gccttgggtt atctatcagg acctagccta   17760
gaagcaggtg tgtggcactt aacacctaag gtcagtgact aactgaacac tcaagtgagt   17820
gccatctttg tcacttcttg actgtgacac aagcaactcc tgatgccaaa gccctgccca   17880
cccctctcat gcccatattt ggacatggta caggtcctca ctggccatgg tctgtgaggt   17940
cctggtcctc tttgacttca taattcctag gggccactag tatctataag aggaagaggg   18000
tgctggctcc caggccacag cccacaaaat tccacctgct cacaggttgg ctggctcgac   18060
ccaggtggtg tccctgctc tgagccagct ccgggccaag ccagcaccat gggaaccccc   18120
aagaagaaga ggaaggtgcg taccgattta aattccaatt tactgaccgt acaccaaaat   18180
ttgcctgcat taccggtcga tgcaacgagt gatgaggttc gcaagaacct gatggacatg   18240
ttcagggatc gccaggcgtt ttctgagcat acctggaaaa tgcttctgtc cgtttgccgg   18300
tcgtggggca catggtgcaa gttgaataac cggaaatggt ttcccgcaga acctgaagat   18360
gttcgcgatt atcttctata tcttcaggcg cgcggtctgg cagtaaaaac tatccagcaa   18420
catttgggcc agctaaacat gcttcatcgt cggtccgggc tgccacgacc aagtgacagc   18480
aatgctgttt cactggttat gcggcggatc cgaaaagaaa acgttgatgc cggtgaacgt   18540
gcaaaacagg taaatataaa attttttaagt gtataatgat gttaaactac tgattctaat   18600
tgtttgtgta ttttaggctc tagcgttcga acgcactgat ttcgaccagg ttcgttcact   18660
catggaaaat agcgatcgct gccaggatat acgtaatctg gcatttctgg ggattgctta   18720
taacaccctg ttacgtatag ccgaaattgc caggatcagg gttaaagata tctcacgtac   18780
tgacggtggg agaatgttaa tccatattgg cagaacgaaa acgtcggtta gcaccgcaag   18840
tgtagagaag gcacttagcc tggggggtaac taaactggtc gagcgatgga tttccgtctc   18900
tggtgtagct gatgatccga ataactaccct gttttgccgg gtcagaaaaa atggtgttgc   18960
cgcgccatct gccaccagcc agctatcaac tcgcgccctg gaagggattt ttgaagcaac   19020
tcatcgattg atttacgcg ctaaggatga tctggtcag agatacctgg cctggtctgg   19080
acacagtgcc cgtgtcgag ccgcgcgaga tatgccccgc gctggagttt caataccgga   19140
gatcatgcaa gctggtggct ggaccaatgt aaatattgtc atgaactata tccgtaacct   19200
ggatagtgaa acaggggcaa tggtgcgcct gctggaagat ggcgattagg cggcggccg   19260
ctaatcgaac ataccacatt tgtagaggtt ttacttgctt taaaaaacct cccacaccctc   19320
cccctgaacc tgaaacataa aatgaatgca attgttgttg ttaacttgtt tattgcagct   19380
tataatggtt acaaataaag caatagcatc acaaatttca caaatataaagc atttttttttca   19440
ctgcattcta gttgtggttt gtccaaactc atcaatgtat cttatcatgt ctggatccccc   19500
cggctagagt ttaaacacta gaactagtgg atcccccggg atcatggcct ccgcgccggg   19560
ttttggcgcc tcccgcggc gccccctcc tcacgcgga cgctgccaaaa tcagacagaa   19620
ggcgcagcga gcgtcctgat ccttccgcccc ggacgtcaga cacagcggcc cgctgctcat   19680
aagactcggc cttagaaccc cagtatcagc agaaggacat tttaggacgg gacttgggtg   19740
actctaggc actggttttc tttccagaga gcggaacagg cgaggaaaag tagtcccttc   19800
tcggcgattc tgcggaggga tctccgtggg gcgggtaaacc ccgatgatta tataaggacg   19860
cgccgggtgt ggcacagcta gttccgctcgc agccgattt tgggtcgggg ttcttgtttg   19920
tggatcgctg tgatcgtcac ttggtgagta gcggggctgct gggctggccg gggctttcgt   19980
ggcgccggg ccgctcggtg gaacggaagc gtgtggagag accgcaaagg gctgtagtct   20040
gggtccgcga gcaaggttgc cctgaactgg gggtttgggg gagcgcagca aaatggcggc   20100
tgttcccgag tcttgaatgg aagacgcttg tgaggcgggc tgtgaggtcg ttgaaacaag   20160
tgggggagca tggtgggcgg caagaaccca aggtcttagg gccttcgcta atgcgggaaa   20220
gctcttattc gggtgagatg ggctgggca ccatctgggg accctgacgt gaagtttgtc   20280
actgactgga gaactcggtt tgtcgtctgt tgcggggggcg gcagtatgg cggtgccgtt   20340
gggcagtgca cccgtacctt tgggagcgcg cgccctcgtc gtgtcgtgac gtcacccgtt   20400
ctgttggctt ataatgcagg gtgggcccac ctgccgtag gtgtgcggta ggcttttctc   20460
cgtcgcagga cgcagggttc gggcctaggg taggctctcc tgaatcgaca ggcgccggac   20520
```

```
ctctggtgag gggagggata agtgaggcgt cagtttcttt ggtcggtttt atgtacctat   20580
cttcttaagt agctgaagct ccggttttga actatgcgct cggggttggc gagtgtgttt   20640
tgtgaagttt tttaggcacc ttttgaaatg taatcatttg ggtcaatatg taattttcag   20700
tgttagacta gtaaattgtc cgctaaattc tggccgtttt tggctttttt gttagacgtg   20760
ttgacaatta atcatcggca tagtatatcg gcatagtata atacgacaag gtgaggaact   20820
aaaccatggg atcggccatt gaacaagatg gattgcacgc aggttctccg gccgcttggg   20880
tggagaggct attcggctat gactgggcac aacagacaat cggctgctct gatgccgccg   20940
tgttccggct gtcagcgcag gggcgcccgg ttcttttgt caagaccgac ctgtccggtg   21000
ccctgaatga actgcaggac gaggcagcgc ggctatcgtg gctggccacg acgggcgttc   21060
cttgcgcagc tgtgctcgac gttgtcactg aagcgggaag ggactggctg ctattgggcg   21120
aagtgccggg gcaggatctc ctgtcatctc accttgctcc tgccgagaaa gtatccatca   21180
tggctgatgc aatgcggcgg ctgcatacgc ttgatccggc tacctgccca ttcgaccacc   21240
aagcgaaaca tcgcatcgag cgagcacgta ctcggatgga agccggtctt gtcgatcagg   21300
atgatctgga cgaagagcat caggggctcg cgccagccga actgttcgcc aggctcaagg   21360
cgcgcatgcc cgacgcgat gatctcgtcg tgacccatgg cgatgcctgc ttgccgaata   21420
tcatggtgga aaatggccgc ttttctggat tcatcgactg tggccggctg ggtgtggcgg   21480
accgctatca ggacatagcg ttggctaccc gtgatattgc tgaagagctt ggcggcgaat   21540
gggctgaccg cttcctcgtg ctttacggta tcgccgctcc cgattcgcag cgcatcgcct   21600
tctatcgcct tcttgacgag ttcttctgag gggatccgct gtaagtctgc agaaattgat   21660
gatctattaa acaataaaga tgtccactaa aatggaagtt tttcctgtca tactttgtta   21720
agaagggtga gaacagagta cctacatttt gaatggaagg attggagcta cggggtggg   21780
ggtggggtgg gattagataa atgcctgctc tttactgaag gctctttat attgctttat   21840
gataatgttt catagttgga tatcataatt taaacaagca aaaccaaatt aagggccagc   21900
tcattcctcc cactcatgat ctatagatct atagatctct cgtgggatca ttgttttct   21960
cttgattccc actttgtggt tctaagtact gtggttccaa aatgtgtcag tttcatagcc   22020
tgaagaacga gatcagcagc ctctgttcca catcacttc attctcagta ttgttttgcc   22080
aagttctaat tccatcagac ctcgacctgc agccctaga taacttcgta taatgtatgc   22140
tatacgaagt tatgctaggt aactatacg gtcctaaggt agcgagctag cacacatcac   22200
aaccacaacc ttctcaggta actatacttg ggacttaaaa aacataatca taatcatttt   22260
tcctaaaacg atcaagactg ataaccattt gacaagacg ataacgacaa gcaccagctg   22320
gcactcttag gtcttcacgt atggtcatca gtttgggttc catttgtaga taagaaactg   22380
aacatataaa ggtctaggtt aatgcaattt acacaaaagg agaccaaacc agggagagaa   22440
ggaaccaaaa ttaaaaattc aaaccagagc aaaggagtta gccctggttt tgctctgact   22500
tacatgaacc actatgtgga gtcctccatg ttagcctagt caagcttatc ctctggatga   22560
agttgaaacc atatgaagga atatttgggg ggtgggtcaa aacagttgtg tatcaatgat   22620
tccatgtggt ttgacccaat cattctgtga atccatttca acagaagata caacgggttc   22680
tgtttcataa taagtgatcc acttccaaat ttctgatgtg ccccatgcta agctttaaca   22740
gaatttatct tcttatgaca aagcagcctc ctttgaaaat atagccaact gcacacagct   22800
atgttgatca attttgttta taatcttgca gaagagaatt tttaaaata gggcaataat   22860
ggaaggcttt ggcaaaaaaa ttgtttctcc atatgaaaac aaaaaaactta ttttttatt   22920
caagcaaaga acctatagac ataaggctat ttcaaaatta tttcagtttt agaaagaatt   22980
gaaagttttg tagcattctg agaagacagc tttcatttgt aatcataggt aatatgtagg   23040
tcctcagaaa tggtgagacc cctgactttg acacttgggg actctgaggg accagtgatg   23100
aagagggcac aacttatatc acacatgcac gagttgggg gagagggtgt cacaacatct   23160
atcagtgtgt catctgccca ccaagtaaca gatgtcagct aagactaggt catgtgtagg   23220
ctgtctacac cagtgaaaat cgcaaaaaga atctaagaaa ttccacattt ctagaaaata   23280
ggtttggaaa ccgtattcca ttttacaaag gacacttaca tttctcttt tgtttttccag   23340
gctaccctga gaaaaaaaga catgaagact caggactcat cttttctgtt ggtgtaaaat   23400
caacacccta aggaacacaa atttctttaa acatttgact tcttgtctct gtgctgcaat   23460
taataaaaaa tggaaagaat ctac                                         23484

SEQ ID NO: 18           moltype = DNA   length = 17768
FEATURE                 Location/Qualifiers
misc_feature            1..17768
                        note = Synthetic
misc_feature            1..46
                        note = Mouse Sequence
misc_feature            47..17381
                        note = Human Sequence
misc_feature            17382..17387
                        note = XhoI
misc_feature            17388..17421
                        note = LoxP
misc_feature            17428..17453
                        note = I-CeuI
misc_feature            17454..17459
                        note = NheI
misc_feature            17460..17768
                        note = Mouse Sequence
source                  1..17768
                        mol_type = other DNA
                        organism = synthetic construct
SEQUENCE: 18
tgcacacaga tcacctttcc tatcaacccc actagcctct ggcaaaatga agtgggtaac   60
ctttatttcc cttctttttc tcttagctc ggcttattcc aggggtgtgt ttcgtcgaga   120
tgcacgtaag aaatccattt ttctattgtt caacttttat tctattttcc cagtaaaata   180
aagttttagt aaactctgca tctttaaaga attattttgg catttatttc taaaatggca   240
tagtattttg tatttgtgaa gtcttacaag gttatcttat taataaaatt caaacatcct   300
aggtaaaaaa aaaaaaaggt cagaattgtt tagtgactgt aattttcttt tgcgcactaa   360
```

```
ggaaagtgca aagtaactta gagtgactga aacttcacag aatagggttg aagattgaat    420
tcataactat cccaaagacc tatccattgc actatgcttt atttaaaaac cacaaaacct    480
gtgctgttga tctcataaat agaacttgta tttatattta ttttcatttt agtctgtctt    540
cttggttgct gttgatagac actaaaagag tattagatat tatctaagtt tgaatataag    600
gctataaata tttaataatt tttaaaatag tattcttagt aattgaatta ttcttctgtt    660
taaaggcaga agaaataatt gaacatcatc ctgagttttt ctgtaggaat cagagcccaa    720
tattttgaaa caaatgcata atctaagtca aatggaaaga aatataaaaa gtaacattat    780
tacttcttgt tttcttcagt atttaacaat ccttttttt cttcccttgc ccagacaaga     840
gtgaggttgc tcatcggttt aaagatttgg gagaagaaaa tttcaaagcc ttgtaagtta    900
aaatattgat gaatcaaatt taatgtttct aatagtgttg tttattattc taaagtgctt    960
atatttcctt gtcatcaggg ttcagattcc aaaacagtgc tgcctcgtag agttttctgc   1020
gttgaggaag atattctgta tctgggctat ccaataaggt agtcactggt cacatggcta   1080
ttgagtactt caaatatgac aagtgcaact gagaaacaaa aacttaaatt gtatttaatt   1140
gtagttaatt tgaatgtata tagtcacatg tggctaatgg ctactgtatt ggacagtaca   1200
gctctggaac ttgcttggtg gaaaggactt taatataggg ttcctttggt ggcttaccca   1260
ctaaatcttc tttacatagc aagcattcct gtgcttagtt gggaatattt aattttttt    1320
ttttttaag acagggtctc gctctgtcgc ccaggctgga gtgcagtggc gcaatctcgg    1380
ctcactgcaa actccgcctc ccgggttcac gccattctcc tgcctcagcc tcccgagtag   1440
ctgggactac aggcgcccgc catcacgccc ggctaatctt ttgtattttt agtagagatg   1500
gggtttcacc gtgtgccagg atggtctcaa tctcctgaca tcgtgatctg cccacctcgg   1560
cctcccaaag tgctgggatt acaggagtga gccaccgcgc ccggcctatt taaatgtttt   1620
ttaatctagt aaaaaatgag aaaattgttt ttttaaaagt ctacctaatc ctacaggcta   1680
attaagacg tgtgtgggga tcaggtgcgg tggttcacac ctgtaatccc agcactttgg    1740
aaggctgatg caggaggatt gcttgagccc aggagttcaa gaccagcctg ggcaagtctc   1800
tttaaaaaaa acaaaacaaa caaacaaaaa aattaggcat ggtggcacat gcctgtagtc   1860
ctagctactt aggaggctga cgtaggagga tcgtttggac ctgagaggtc aaggctacag   1920
tgagccatga ttgtgccact gcactccagc ctggggtgaca gagtgagact ctgtctcaaa  1980
aaagaaaaag gaaatctgtg gggtttgttt tagttttaag taattctaag gactttaaaa   2040
atgcctagtc ttgacaatta gatctatttg gcatacaatt tgcttgctta atctatgtgt   2100
gtgcatagat ctactgacac acgcatacat ataaacatta gggaactacc attctctttg   2160
cgtaggaagc cacatatgcc tatctaggcc tcagatcata cctgatatga ataggctttc   2220
tggataatgg tgaagaagat gtataaaaga tagaacctat acccatacat gatttgttct   2280
ctagcgtagc aacctgttac atattaaagt tttattatac tacatttttc tacatccttt   2340
gtttcagggt gttgattgcc tttgctcagt atcttcagca gtgtccattt gaagatcatg   2400
taaaattagt gaatgaagta actgaatttg caaaaacatg tgttgctgat gagtcagctg   2460
aaaattgtga caaatcactt gtaagtacat tctaattgtg gagattcttt cttctgtttg   2520
aagtaatccc aagcatttca aaggaattt ttttaagttt tctcaattat tattaagtgt    2580
cctgatttgt aagaaacact aaaaagttgc tcatagactg ataagccatt gtttcttttg   2640
tgatagagat gctttagcta tgtccacagt tttaaaatca tttctttatt gagaccaaac   2700
acaacagtca tggtgtattt aaatggcaat ttgtcattta taaacacctc tttttaaaat   2760
ttgaggtttg gtttctttt gtagaggcta atagggatat gatagcatgt atttatttat    2820
ttatttatct tattttatta tagtaagaac ccttaacatg agatctaccc tgttatattt   2880
ttaagtgtac aatccattat tgttaactac gggtacactg ttgtatagct tactcatctt   2940
gctgtattaa aactttgtgc ccattgatta gtaaccctc gtttcgtcct cccccagcca    3000
ctggcaacca gcattatact ctttgattct atgagtttga ctactttagc taccttatat   3060
aagtggtatt atgtactgtt tatcttttta tgactgactt atttccctta gcatagtgca   3120
ttcaaagtcc aaccatgttg ttgcctattg cagaatttcc ttcttttcaa ggctgaataa   3180
tattccagtg catgtgtgta ccacattttc tttatccatt aatttgttga ttgatagaca   3240
tttaggttgg ttttctacat cttgactatc atgaatagtg ttgcaatgaa cacaggagag   3300
ctactatctc ttagagatga tatcatggtt tttatcatca gaaaacaccc actgatttct   3360
atgctaattt tgttacctgg gtggaataat agtacagcta tatattcctc attttagata   3420
tctttgtatt tctacataca ataaaaaagc agagtactta gtcatgttga agaactttaa   3480
acttttagta tttccagatc aatcttcaaa acaaggacag gtttatcttt ctctcaccac   3540
tcaatctata tatacctctt gtgggcaagg ccagttttta tcactggagc cttccccctt   3600
tttattatgt acctctccct cacagcagag tcaggactt aacttaccac aatactatgg    3660
ctctacatat gaaatcttaa aaatacataa aaattaataa attctgtcta gagtagtata   3720
ttttccctgg ggttacagtt actttcataa taaaaattag agataaggaa aggactcatt   3780
tattggaaag tgattttagg taacattct ggaagaaaaa tgtctatatc ttaatagtca    3840
cttaatatat gatggattgt gttactcctc agttttcaat ggcatatact aaaacatggc   3900
cctctaaaaa gggggcaaat gaaatgagaa actctctgaa tgttttctc ccctaggtga    3960
attcacctgc tgcttagaag cttatttct cttgatttct gttataatga ttgctcttac    4020
cctttagttt taagtttcaa aataggagtc atataacttt ccttaaagct attgactgtc   4080
ttttttgtcct gttttattca ccatgagtta tagtgtgaca gttaattctt atgaaaatta  4140
tatagaagtg gttaaatcat cagaaactgt aaacctcgat tgggaggggga agcggatttt  4200
taaatgattt cctgaccaag cttaaccagt atattaaatc ctttgtactg ttctttggct   4260
ataaagaaaa aaggtactgt ccagcaactg aaacctgctt tcttccattt agcatacccct  4320
ttttggagac aaattatgca cagttgcaac tcttcgtgaa acctatggtg aaatggctga   4380
ctgctgtgca aaacaagaac ctgagagaaa tgaatgcttc ttgcaacaca aagatgacaa   4440
cccaaacctc ccccgattgg tgagaccaga ggttgatgg atgtgcactg cttttcatga    4500
caatgaagag acattttga aaaagtaagt aatcagatgt ttatagttca aaattaaaaa    4560
gcatggagta actccatagg ccaacactct ataaaaatta ccataacaaa aatattttca   4620
acattaagac ttggaagttt tgttatgatg atttttttaaa gaagtagtat ttgataccac  4680
aaaattctac acagcaaaaa atatgatcaa agatattttg aagtttattg aaacaggata   4740
caatctttct gaaaaattta agatagacaa atttatttaat gtattacgaa gatatgtatt  4800
tatggttgtt ataattgatt tcgtttagt cagcaacatt atattgccaa aatttaacca    4860
tttatgcaca cacacacaca cacacacaca cttaaccctt ttttccacat acttaaagaa   4920
tgacagagac aagaccatca tgtgcaaatt gagcttaatt ggttaattag atatctttgg   4980
aatttggagg ttctggggag aatgtcgatt acaattattt ctgtaatatt gtctgctata   5040
gaaaagtgac tgttttctt tttcaaaatt tagatactta tatgaaattg ccagaagaca    5100
```

```
tccttactttt tatgcccegg aactecttit ctttgctaaa aggtataaag ctgcttttac    5160
agaatgttgc caagctgctg ataaagctgc ctgcctgttg ccaaaggtat tatgcaaaag    5220
aatagaaaaa aagagttcat tatccaacct gattttgtcc attttgtggc tagatttagg    5280
gaacctgagt gtctgataca aacttteega catggtcaaa aaagccttcc ttttatctgt    5340
cttgaaaatc tttcatcttt gaaggcctac actctcgttt cttcttttaa gatttgccaa    5400
tgatgatctg tcagaggtaa tcactgtgca tgtgtttaaa gatttcacca ctttttatgg    5460
tggtgatcac tatagtgaaa tactgaaact tgtttgtcaa attgcacagc aaggggccac    5520
agttcttgtt tatcttttca tgataatttt tagtagggag ggaattcaaa gtagagaatt    5580
ttactgcatc tagatgcctg agttcatgca ttcattccat aaatatatat tatggaatgc    5640
tttatttcct tttctgagga gtttactgat gttggtggag gagagactga aatgaattat    5700
acacaaaatt taaaaattag caaaattgca gccctggga tattagcgta ctcttctct    5760
gacttttctc ccactttaa ggctctttt cctggcaatg tttccagttg gtttctaact    5820
acataggaa ttccgctgtg accagaatga tcgaatgatc tttcctttte ttagagagca    5880
aaatcattat tcgctaaagg gagtacttgg gaatttaggc ataaattatg ccttcaaaat    5940
ttaatttggc acagtctcat ctgagcttat ggagggtgt ttcatgtaga attttttcttc    6000
taattttcat caaattattc cttttgtag ctcgatgaac ttcggatga agggaaggct    6060
tcgtctgcca aacagagact caagtgtgcc agtctcaaa aatttggaga aagagctttc    6120
aaagcatggt aaatacttt aaacatagtt ggcatccttta taacgatgta aatgataatg    6180
cttcagtgac aaattgtaca ttttatgta ttttgcaaag tgctgtcaaa tacatttctt    6240
tggttgtcta acaggtagaa ctcaatagaa ggtaaaaatc agaatatcaa tgacaatttg    6300
acattatttt taatcttttc ttttctaaat agttgaataa tttagaggac gctgtccttt    6360
tgtcctaaa aaagggaca gatatttaag ttctatttat ttataaaatc ttggactctt    6420
attctaatgg ttcattattt ttatagagct gtaggcatgg ttctttattt aattttttaa    6480
agttatttt aattttttgtg gatacagagt aggtatacat atttacgggg tatatgagat    6540
attttgatat aagtatacaa catatataat ccctttattt aatttatct tcccccaat    6600
gatctaaaac tatttgcttg tccttttatg tcttatagtt aaattcagtc accaactaag    6660
ttgaagttac ttcttattt tgcatagctc cagctctgat cttcatctca tgttttgcc    6720
tgagcctctg ttttcatatt acttagttgg ttctgggagc atactttaat agccgagtca    6780
agaaaaatac tagctgcccc gtcacccaca ctcctcacct gctagtcaac agcaaatcaa    6840
cacaacagga aataaaatga aaataataga cattatgcat gctctctaga aactgtcaat    6900
tgaactgtat ttgctcatca ttcctaccat ctacaccacc aaaatcaacc aaatttatga    6960
aaaaaacag ccccaacata aaattataca cagataaaca ggctatgatt ggttttggga    7020
aagaagtcac ctttacctga tttaggcaac tgtgaaatga ctagaatga aagaaaatta    7080
gacgtttaca tcttgtcata gagtttgaag atagtgctgg atcttctttt ttataagtaa    7140
gatcaataaa aactccctca ttctgtagaa gttatgattt cttttctaag agaccttag    7200
aagtcagaaa aaatgtgttt caattgagaa aaaagataac tggagtttgt gtagtacttc    7260
ccagattata aaatgctttt gtatgtatta tctaattta tcctcaaaac ttcttcaatt    7320
tagcatgttg tcatgacact gcagaggctg aagctcagag aggctgagcc ctctgctaac    7380
aagtcctact gctaacaagt gataaagcca gagctggaag tcacctctgg actccaaacc    7440
tgatgcttct cagcctgttg ccccttttag agttcctttt taatttctgc ttttatgact    7500
tgctagattt ctacctacca cacacactct taaatggata attctgccct aaggataagt    7560
gattaccatt tggttcagaa ctagaactaa tgaatttaa aaattatttc tgtatgtcca    7620
ttttgaattt tcttatgaga aatagtattt gcctagtgtt ttcatataaa atatcgcatg    7680
ataataccat tttgattggc gatttttctt ttagggcagt agctcgcctg agccagagat    7740
ttcccaaagc tgagtttgca gaagtttcca agttagtgac agatcttacc aaagtccaca    7800
cggaatgctg ccatggagat ctgcttgaat gtgctgatga cagggtaaag agtcgtcgat    7860
atgcttttg gtagcttgca tgctcaagtt ggtagaagtg atgcgtttgg tatcattggt    7920
gatagctgac agtgggttga gattgtcttc tgtgctttcg tctgtcctat cttcaatctt    7980
tccctgccta tggtggtggt acctttctgt ttaacctg gctataaatt accagataaa    8040
cccattcact gatttgtaac tccttcagt catgctctaa ctgtaaatga aggcttaaac    8100
tgaagtagaa cagttacaag gttttactg gcagaacatc ttgcaaggta gatgtctaaa    8160
aagatttttt tttctttttt taagacagag tttcgctctt gtttcccagg ctggggtgca    8220
atggtgtgat cttggctcag cgcaacctct gcctcctggg ttcaagtgat tctcatgcct    8280
cagcctccca agtagctggg attacaggca tgcgccacca cacctggcta attttgtatt    8340
tttagtagag gcgggttc accatattgt ccagactggt ctcgaactcc tgacctcagg    8400
tgatccaccc gccttggcct cccaaagtgc tgggattaca ggcatgagcc accttgccca    8460
gcctaagaag attttttgag ggaggtaggg ggacttggag aaggtcacta cttgaagaga    8520
tttttggaaa tgatgtattt ttcttctcta tattccttcc cttaattaac tctgtttgtt    8580
agatgtgaaa atatttggaa tgatatctct tttctcaaaa cttataaatat tttctttctc    8640
cctttcttca agattaaaact tatgggcaaa tactagaatc ctaatctctc atggcacttt    8700
ctggaaaatt taaggcggtt attttatata tgtaagcagg gcctatgact atgatcttga    8760
ctcattttc aaaaatcttc tatattttat ttagttattt ggtttcaaaa ggcctgcact    8820
taattttggg ggattatttg gaaaacagc attgagtttt aatgaaaaaa acttaaatgc    8880
cctaacagta gaaacataaa attaataaat aactgagctg agcacctgct actgattagt    8940
ctattttaat taagtgggaa tgttttttgta gtcctatcta catctccagg tttaggagca    9000
aacagagtat gttcatagaa ggaatatgtg tatggtctta gaatacaatg aatatgttct    9060
gccaacttaa taaggtctg aggagaaagt gtagcaatgt caattcgtgt tgaacaattt    9120
ccaccaactt acttataggc ggaccttgcc aagtatatct gtgaaaatca agattcgatc    9180
tccagtaaac tgaaggaatg ctgtgaaaaa cctctgttgg aaaaatccca ctgcattgcn    9240
gaagtggaaa atgatgagat gcctgctgac ttgccttcat tagctgctga ttttgttgaa    9300
agtaaggatg tttgcaaaaa ctatgctgag gcaaggatg tcttcctggg catgtaagta    9360
gataagaaat tattcttta tagctttggc atgacctcac aacttaggag atagcctag    9420
gcttttctgt ggagttgcta caatttccct gctgcccaga atgtttcttc atccttccct    9480
tcccaggct ttaacaattt ttgaaatagt taattagttg aatacattgt cataaaataa    9540
tacatgttca tggcaaagct caacattcct tactccttag gggtatttct gaaaatacgt    9600
ctagaaacat tttgtgtata tataaattat gtatacttca gtcattcatt ccaagtgtat    9660
ttcttgaaca tctataatat atgtgtgtga ctatgtattg cctgtctatc taactaatct    9720
aatctaatct agtctatcta tctaatctat gcaatgatag caaagaagta taaaagaaa    9780
tatagagtct gacaccaggt gctttatatt tggtgaaaag accagaagtt cagtataatg    9840
```

```
gcaatatggt aggcaactca attacaaaat aaatgtttac atattgtcag aagttgtggt   9900
gataaactgc atttttgttg ttggattatg ataatgcact aaataatatt tcctaaaatt   9960
atgtacccta caagatttca ctcatacaga gaagaaagag aatattttaa gaacatatct  10020
ctgcccatct atttatcaga atcctttga gatgtagttt aaatcaaaca aaatgttaat  10080
aaaaataaca agtatcattc atcaaagact tcatatgtgc caagcagtgt gtgctttgtg  10140
tagattatgt catatagttc tcataatcca ccttccgaga cagatactat ttattttttg  10200
agacagagtt ttactcttgt tgcccaggct ggagtgcaat ggtgccatct cggctcacca  10260
caacctccgc ctcccaggtt caagcgattc tcctgcctca gcctcctggg attacaggca  10320
tgcaccacca tgcctggcta attttgtatt tttagtagag atggggtttc accatgttgg  10380
tcagactggt ctcaaactcc tgacctctgg tgatatgcct gcctcagcct cctaaagtgc  10440
tgggattaca ggcatgagcc actgtgccca gccgacagat actattatta tttccattct  10500
accgagaagg agactaaggc tctgatcatt taaataagtt gcctaaggtg atgcagtgat  10560
ataagtagca gagctaggaa ttgagccttg gtaactttaa ctctggaccc caagtcctta  10620
gctactaagc tttactgcat ggggtttagt caaattaaga cttttggaat atgagttact  10680
tttgagatta gctttgtgat atttttttgtg ctcatttgtc caacaaagtc tattttattt  10740
tcatcttaat taggtttttg tatgaatatg caagaaggca tcctgattac tctgtcgtgc  10800
tgctgctgag acttgccaag acatatgaaa ccactctaga gaagtgctgt gccgctgcag  10860
atcctcatga atgctatgcc aaagtggtag gtttattgtt ggaaaaaaat gtagttcttt  10920
gactgatgat tccaataatg agaaagaaaa ataatgcaag aatgtaaaat gatatacagt  10980
gcaatttaga tcttttcttg agatggtttc aattctggaa tcttaaacat gaaagaaaaa  11040
gtagcettag aatgattaac aaaatttaga ctagttagaa tagaaagatc tgaatagagc  11100
aatctctaaa aaatttgat cttttttttct cttttcaca atcctgagaa caaaaaaaaa  11160
ttaaatttaa atgttaatta gaagatattt aacttagatg taaagtgagt taacctgatt  11220
ccaggattaa tcaagtacta gaattagtat cttatggcaa attatagaac ctatcccttt  11280
agaatatttt caaatctttt tgaggatgtt taggaatagt tttacaagaa attaagttag  11340
gagaggaaat ctgttctgga tgattttag ggttcccact agcatatgta atggtttctg  11400
aactattcag aatcagagaa aactcatttt tcctgctttc aagaagctac tgtatgccaa  11460
gcaccatgca caaacaatga ccaacgtaaa atctctcatt ttggagagcc tggaatctaa  11520
ctggaaaggt gaactaataa taataatatg tacaatcata gccatcattt attaaacttt  11580
tattatatgc aaggcactgt ttaatttcat tagcttacct ggtttacaga gcagctctat  11640
gagatgagtg ccatctttgc ccctatttta gggataagga ttctgaaatg tggagatggt  11700
aagtaaaatt gcacaactga agaatgagtt acatgacttg gctcaaatac tggtcattga  11760
actccagagc ctgaatattc ttaaccactt acatgatgca agctcaccaa ataaatagtt  11820
cgaatgtatt gtgacagagc ggcattgata ttcatctatt catgtggctt tgagtaggaa  11880
gaagaaagga tatcattctg accagagggg tgaaaaacaa cctgcatctg atcctgaggc  11940
ataatactat taacacaatt cttttatgtt tcagttcgat gaatttaaac ctcttgtgga  12000
agagcctcag aatttaatca aacaaaattg tgagcttttt gagcagcttg agagtacaa  12060
attccagaat gcgtaagtaa ttttttattga ctgatttttt ttatcaatttt gtaattattt  12120
aagcttaat atatgagcca cctagcatag aacttttaag aatgaaaata cattgcatat  12180
ttctaatcac tctttgtcaa gaaagatagg agaggagaa taaaatagtt gatggggtgg  12240
agaggtctat atttgaatgt agtctaaaaa ttgttctctt aagattggaa gtatgtaggc  12300
tgggagggta aataccaaat cttggtatat cagaactgag catgtcccctt gaaggttaag  12360
aaatagttaa tgggcaaata gagcatggca atattttgta gagcagcaga tagtaggcct  12420
tgaatagatg tcgctcaaaa agtaatatgt aagctgaaca caaaaatgta acaaatgaat  12480
ttagatacat atttgaatat taaattcagg ttgtttggga gatgcaccta gtctttgatg  12540
gttaaaccct tccctccata gaagagacag agacagaatg gcttgctgga ctaatgtccc  12600
aattcaatag agtcttatct atgaaggtta aaaacaagaa gacatatt atacagtaga  12660
tatttattgt gtggctcata cacatgtgtc tcttctgatt atggatttta gagataataa  12720
cagtgaacaa gacatagttt cttttcctcga gtagattaaa gtcatacatt gacttttaat  12780
ggtgactggc attcttaata catgattatt atatattagg taccatgtca gattaattat  12840
aatactttac tactttttaat ttaaccttg aactatccct attgagtcag atatatttcc  12900
ttccattttc tacttgtatc tttcaagttt agcatatgct gatacatatg aagctctctc  12960
caggttttat tgaaagaaga aattaataaa tttattaatg tcactgaatt aggcaactca  13020
ctttcccaag attatgcaag tggtacaggt ggaactcaaa gccaagttta actagttgtt  13080
caggagaatg ttttctaccc tccactaacc cactactctg cagatggaa taatatgatg  13140
aatgagaacat agcaacatct tagttgattc cggccaagtg ttctctgttt tatctactat  13200
gttagacagt ttcttgcctt gctgaaaaca catgacttct ttttttcagg ctattagttc  13260
gttacaccaa gaaagtaccc caagtgtcaa ctccaactct tgtagaggtc tcaagaaacc  13320
taggaaaggt gggcagcaaa tgttgtaaac atcctgaagc aaaaagaatg ccctgtgcag  13380
aagactatgt gagtctttaa aaaaaatataa taaattaata atgaaaaaat tttacctta  13440
gatattgata atgctagctt tcataagcag aaggaagtaa tgtgtgtgtg tgcatgtttg  13500
tgtgcatgtg tgtgtcatg cacgtgtgtg tatgtgtgat attggcagtc aaggccccga  13560
ggatgataat ttttttttttt tttttgagac ggagtctcgc tttgttgtcc aggctggagt  13620
gcagtggtgc catctcggct cactgcaacc tccgcctccc aggttcaagc cattctcctg  13680
cctcagcctc ccaagtagct gggactacag gtgcatgcca ccatgcctgg ctaatttttt  13740
gtatttttag tagaaaattt tcagcttcac ctcttttgaa tttctgctct cctgcctgtt  13800
ctttagctat ccgtggtcct gaaccagtta tgtgtgttgc atgagaaaac gccagtaagt  13860
gacagagtca ccaaatgctg cacagaatcc ttggtgaaca ggcgaccatg ctttttcagct  13920
ctggaagtcg atgaaacata cgttcccaaa gagtttaatg ctgaaacatt caccttccat  13980
gcagatatat gcacactttc tgagaaggag agacaaatca agaaacaaac gtgaggagta  14040
tttcattact gcatgtgttt gtagtcttga tagcaagaac tgtcaattca agctagcaac  14100
tttttcctga agtagtgatt atatttctta gaggaaagta ttggagtgtt gcccttatta  14160
tgctgataag agtacccaga ataaaatgaa taacttttta aagcaaaaat cctctgttat  14220
aatattgcta aaattattca gagtaatatt gtggattaaa gccacaatag aataacatgt  14280
taggccatat tcagtagaaa aagatgaaca attaactgat aaatttgtgc acatggcaaa  14340
ttagttaatg ggaaccatag gagaaattat ttctagatgt aaataattat tttaagtttg  14400
ccctatggtg gccccacaca tgagacaaac ccccaagatg tgactttga gaatgagact  14460
tggataaaaa acatgtagaa atgcaagccc tgaagctcaa ctcccctattg ctatcacagg  14520
ggttataatt gcataaaatt tagctataga aagttgctgt catctcttgt gggctgtaat  14580
```

```
catcgtctag gcttaagagt aatattgcaa aacctgtcat gcccacacaa atctctccct   14640
ggcattgttg tctttgcaga tgtcagtgaa agagaaccag cagctcccat gagtttggat   14700
agccttattt tctatagcct ccccactatt agctttgaag ggagcaaagt ttaagaacca   14760
aatataaagt ttctcatctt tatagatgag aaaaatttta aataaagtcc aagataatta   14820
aattttaag gatcatttt agctctttaa tagcaataaa actcaatatg acataatatg    14880
gcacttccaa aatctgaata atatataatt gcaatgacat acttcttttc agagatttac   14940
tgaaaagaaa tttgttgaca ctacataacg tgatgagtgg tttatactga ttgtttcagt   15000
tggtcttccc accaactcca tgaaagtgga ttttattatc ctcatcatgc agatgagaat   15060
attgagactt atagcggtat gcctgagccc caaagtactc agagttgcct ggctccaaga   15120
tttataatct taaatgatgg gactaccatc cttactctct ccattttct atacgtgagt    15180
aatgttttt ctgttttttt ttttctttt tccattcaaa ctcagtgcac ttgttgagct     15240
cgtgaaacac aagcccaagg caacaaaaga gcaactgaaa gctgttatgg atgatttcgc   15300
agcttttgta gagaagtgct gcaaggctga cgataaggag acctgctttg ccgaggaggt   15360
actacagttc tcttcatttt aatatgtcca gtattcattt ttgcatgttt ggttaggcta   15420
gggcttaggg atttatatat caaaggaggc tttgtacatg tgggacaggg atcttatttt   15480
acaaacaatt gtcttacaaa atgaataaaa cagcactttg tttttatctc ctgctctatt   15540
gtgccatact gttaaatgtt tataatgcct gttctgtttc caaatttgtg atgcttatga   15600
atattaatag gaatatttgt aaggcctgaa atattttgat catgaaatca aaacattaat   15660
ttatttaaac atttacttga aatgtggtgg tttgtgattt agttgatttt ataggctagt   15720
gggagaattt acattcaaat gtctaaatca cttaaaattg ccctttatgg cctgacagta   15780
acttttttt attcatttgg ggacaactat gtccgtgagc ttccgtccag agattatagt    15840
agtaaattgt aattaaagga tatgatgcac gtgaaatcac tttgcaatca tcaatagctt   15900
cataaaatgtt aattttgtat cctaatagta atgctaatat tttcctaaca tctgtcatgt   15960
ctttgtgttc agggtaaaaa acttgttgct gcaagtcaag ctgccttagg cttataacat   16020
cacatttaaa agcatctcag gtaactatat tttgaattt ttaaaaaagt aactataata    16080
gttattatta aaatagcaaa gattgaccat ttccaagacc catatagacc agcaccgacc   16140
actattctaa actatttatg tatgtaaata ttagctttta aaattctcaa aatagttgct   16200
gagttgggaa ccactattat ttctattttg tagatgagaa aatgaagata aacatcaaag   16260
catagattaa gtaattttcc aaagggtcaa aattcaaaat tgaaaccaaa gtttcagtgt   16320
tgcccattgt cctgttctga cttatatgat gcggtacaca gagccatcca agtaagtgat   16380
ggctcagcag tggaatactc tgggaattag gctgaaccac atgaaagagt gctttataga   16440
gcaaaaacag ttgaatatca gtgatttcac atggttcaac ctaatagttc aactcatcct   16500
ttccattgga gaatatgatg gatctacctt ctgtgaactt tatagtgaag aatctgctat   16560
tacattcca atttgtcaac atgctgagct ttaataggac ttatcttctt atgacaacat    16620
ttattggtgt gtcccccttgc ctagcccaac agaagaattc agcagccgta agtctaggac   16680
aggcttaaat tgtttcact ggtgtaaatt gcagaaagat gatctaagta atttggcatt    16740
tattttaata ggtttgaaaa acacatgcca ttttacaaat aagacttata tttgtccttt   16800
tgtttttcag cctaccatga gaataagaga aagaaaatga agatcaaaag cttattcatc   16860
tgttttttctt tttcgttggt gtaaagccaa caccctgtct aaaaaacata aattctta    16920
atcatttttgc ctcttttctc tgtgcttcaa ttaataaaaa atggaaagaa tctaatagag   16980
tggtacagca ctgttatttt tcaaagatgt gttgctatcc tgaaaattct gtaggttctg   17040
tggaagttcc agtgttctct cttattccac ttccggtagag gatttctagt ttcttgtggg   17100
ctaattaaat aaatcattaa tactcttcta agttatggat tataaacatt caaaataata   17160
ttttgacatt atgataattc tgaataaaag aacaaaaacc atggtatagg taaggaatat   17220
aaaacatggc tttaccttta gaaaaaacaa ttctaaaatt catatggaat caaaaagag    17280
cctgcagaac caaagtaaga ctaagcaaaa agaacaaatt acctgatttc aaactacact   17340
ataaggccat agtcaccgaa acagcaaggt actggtataa actcgagata acttcgtata   17400
atgtatgcta tacgaagtta tgctaggtaa ctataacggt cctaaggtag cgagctagca   17460
cacatcacaa ccacaacctt ctcaggtaac tatacttggg acttaaaaaa cataatcata   17520
atcattttc ctaaaacgat caagactgat aaccatttga caagagccat acagacaagc    17580
accagctggc actcttaggt cttcacgtat ggtcatcagt ttgggttcca tttgtagata   17640
agaaactgaa catataaagg tctaggttaa tgcaatttac acaaaaggag accaaaccag   17700
ggagagaagg aaccaaaatt aaaaattcaa accagagcaa aggagttagc cctggttttg   17760
ctctgact                                                           17768

SEQ ID NO: 19            moltype = DNA   length = 120
FEATURE                  Location/Qualifiers
misc_feature             1..120
                         note = Synthetic
misc_feature             1..60
                         note = Mouse Sequence
misc_feature             61..120
                         note = Human Sequence
source                   1..120
                         mol_type = other DNA
                         organism = synthetic construct
SEQUENCE: 19
agagcgagtc tttctgcaca cagatcacct ttcctatcaa ccccactagc ctctggcaaa   60
atgaagtggg taacctttat ttcccttctt tttctcttta gctcggctta ttccaggggt  120

SEQ ID NO: 20            moltype = DNA   length = 160
FEATURE                  Location/Qualifiers
misc_feature             1..160
                         note = Synthetic
misc_feature             1..60
                         note = Human Sequence
misc_feature             61..66
                         note = XhoI
misc_feature             67..100
```

```
                        note = LoxP
misc_feature            101..160
                        note = Cassette
source                  1..160
                        mol_type = other DNA
                        organism = synthetic construct
SEQUENCE: 20
cctgatttca aactacacta taaggccata gtcaccgaaa cagcaaggta ctggtataaa    60
ctcgagataa cttcgtataa tgtatgctat acgaagttat atgcatgcca gtagcagcac   120
ccacgtccac cttctgtcta gtaatgtcca acacctccct                         160

SEQ ID NO: 21           moltype = DNA   length = 192
FEATURE                 Location/Qualifiers
misc_feature            1..192
                        note = Synthetic
misc_feature            1..60
                        note = Cassette
misc_feature            61..94
                        note = LoxP
misc_feature            101..126
                        note = I-CeuI
misc_feature            127..132
                        note = NheI
misc_feature            133..192
                        note = Mouse Sequence
source                  1..192
                        mol_type = other DNA
                        organism = synthetic construct
SEQUENCE: 21
cattctcagt attgttttgc caagttctaa ttccatcaga cctcgacctg cagcccctag    60
ataacttcgt ataatgtatg ctatacgaag ttatgctagg taactataac ggtcctaagg   120
tagcgagcta gcacacatca caaccacaac cttctcaggt aactatactt gggacttaaa   180
aaacataatc at                                                       192

SEQ ID NO: 22           moltype = DNA   length = 198
FEATURE                 Location/Qualifiers
misc_feature            1..198
                        note = Synthetic
misc_feature            1..60
                        note = Human Sequence
misc_feature            61..66
                        note = XhoI
misc_feature            67..100
                        note = LoxP
misc_feature            107..132
                        note = I-CeuI
misc_feature            133..138
                        note = NheI
misc_feature            139..198
                        note = Mouse Sequence
source                  1..198
                        mol_type = other DNA
                        organism = synthetic construct
SEQUENCE: 22
cctgatttca aactacacta taaggccata gtcaccgaaa cagcaaggta ctggtataaa    60
ctcgagataa cttcgtataa tgtatgctat acgaagttat gctaggtaac tataacggtc   120
ctaaggtagc gagctagcac acatcacaac cacaaccttc tcaggtaact atacttggga   180
cttaaaaaac ataatcat                                                 198

SEQ ID NO: 23           moltype = DNA   length = 29
FEATURE                 Location/Qualifiers
misc_feature            1..29
                        note = Synthetic
source                  1..29
                        mol_type = other DNA
                        organism = synthetic construct
SEQUENCE: 23
gtaaccttta tttcccttct ttttctctt                                      29

SEQ ID NO: 24           moltype = DNA   length = 14
FEATURE                 Location/Qualifiers
misc_feature            1..14
                        note = Synthetic
source                  1..14
                        mol_type = other DNA
                        organism = synthetic construct
SEQUENCE: 24
agctcggctt attc                                                     14
```

| | | |
|---|---|---|
| SEQ ID NO: 25<br>FEATURE<br>misc_feature<br><br>source | moltype = DNA   length = 20<br>Location/Qualifiers<br>1..20<br>note = Synthetic<br>1..20<br>mol_type = other DNA<br>organism = synthetic construct | |
| SEQUENCE: 25<br>cgtgcatctc gacgaaacac | | 20 |
| SEQ ID NO: 26<br>FEATURE<br>misc_feature<br><br>source | moltype = DNA   length = 26<br>Location/Qualifiers<br>1..26<br>note = Synthetic<br>1..26<br>mol_type = other DNA<br>organism = synthetic construct | |
| SEQUENCE: 26<br>gcagaaccaa agtaagacta agcaaa | | 26 |
| SEQ ID NO: 27<br>FEATURE<br>misc_feature<br><br>source | moltype = DNA   length = 20<br>Location/Qualifiers<br>1..20<br>note = Synthetic<br>1..20<br>mol_type = other DNA<br>organism = synthetic construct | |
| SEQUENCE: 27<br>agaacaaatt acctgatttc | | 20 |
| SEQ ID NO: 28<br>FEATURE<br>misc_feature<br><br>source | moltype = DNA   length = 23<br>Location/Qualifiers<br>1..23<br>note = Synthetic<br>1..23<br>mol_type = other DNA<br>organism = synthetic construct | |
| SEQUENCE: 28<br>tgtttcggtg actatggcct tat | | 23 |
| SEQ ID NO: 29<br>FEATURE<br>misc_feature<br><br>source | moltype = DNA   length = 22<br>Location/Qualifiers<br>1..22<br>note = Synthetic<br>1..22<br>mol_type = other DNA<br>organism = synthetic construct | |
| SEQUENCE: 29<br>gccgagaagc acgtaagagt tt | | 22 |
| SEQ ID NO: 30<br>FEATURE<br>misc_feature<br><br>source | moltype = DNA   length = 22<br>Location/Qualifiers<br>1..22<br>note = Synthetic<br>1..22<br>mol_type = other DNA<br>organism = synthetic construct | |
| SEQUENCE: 30<br>atgttttttc atctctgctt gt | | 22 |
| SEQ ID NO: 31<br>FEATURE<br>misc_feature<br><br>source | moltype = DNA   length = 27<br>Location/Qualifiers<br>1..27<br>note = Synthetic<br>1..27<br>mol_type = other DNA<br>organism = synthetic construct | |
| SEQUENCE: 31<br>aataccaggc ttccattact agaaaaa | | 27 |
| SEQ ID NO: 32<br>FEATURE<br>misc_feature<br><br>source | moltype = DNA   length = 20<br>Location/Qualifiers<br>1..20<br>note = Synthetic<br>1..20<br>mol_type = other DNA<br>organism = synthetic construct | |
| SEQUENCE: 32<br>ccctcccatg gcctaacaac | | 20 |

-continued

```
SEQ ID NO: 33            moltype = DNA  length = 25
FEATURE                  Location/Qualifiers
misc_feature             1..25
                         note = Synthetic
source                   1..25
                         mol_type = other DNA
                         organism = synthetic construct
SEQUENCE: 33
ttgggcacaa cagatgtcag agagc                                          25

SEQ ID NO: 34            moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 34
acgtgccttg cattgctta                                                 19

SEQ ID NO: 35            moltype = DNA  length = 17335
FEATURE                  Location/Qualifiers
source                   1..17335
                         mol_type = other DNA
                         organism = Homo sapiens
SEQUENCE: 35
atgaagtggg taacctttat ttcccttctt tttctcttta gctcggctta ttccaggggt    60
gtgtttcgtc gagatgcacg taagaaatcc attttttctat tgttcaactt ttattctatt  120
ttcccagtaa aataaagttt tagtaaactc tgcatcttta aagaattatt ttggcattta   180
tttctaaaat ggcatagtat tttgtatttg tgaagtctta caaggttatc ttattaataa   240
aattcaaaca tccctaggtaa aaaaaaaaaa aggtcagaat tgtttagtga ctgtaatttt  300
cttttgcgca ctaaggaaag tgcaaagtaa cttagagtga ctgaaacttc acagaatagg   360
gttgaagatt gaattcataa ctatcccaaa gacctatcca ttgcactatg ctttattttaa  420
aaaccacaaa acctgtgctg ttgatctcat aaatagaact tgtatttata tttattttca   480
ttttagtctg tcttcttggt tgctgttgat agacactaaa agagtattag atattatcta   540
agtttgaata taaggctata aatatttaat aattttttaaa atagtattct tggtaattga  600
attattcttc tgtttaaagg cagaagaaat aattgaacat catcctgagt tttctgtag   660
gaatcagagc ccaatatttt gaaacaaatg caatatctaa gtcaaatgaa aagaaatata  720
aaaagtaaca ttattacttc ttgttttctt cagtatttaa caatccttttt tttctctcc    780
ttgcccagac aagagtgagg ttgctcatcg gtttaaagat ttgggagaag aaaatttcaa   840
agccttgtaa gttaaaatat tgatgaatca aatttaatgt ttctaatagt gttgtttatt   900
attctaaagt gcttatatttt ccttgtcatc agggttcaga ttctaaaaca gtgctgcctc   960
gtagagtttt ctgcgttgag gaagatattc tgtatctggg ctatccaata aggtagtcac  1020
tggtcacatg gctattgagt acttcaaata tgacaagtgc aactgagaaa caaaaactta  1080
aattgtattt aattgtagtt aatttgaatg tatatagtca catgtggcta atggctactg  1140
tattggacag tacagctctg gaacttgctt ggtggaaagg actttaatat aggtttcctt  1200
tggtggctta cccactaaat cttctttaca tagcaagcat tcctgtgctt agttgggaat  1260
atttaattt ttttttttttt taagacaggg tctcgctctg tcgcccaggc tggagtgcag  1320
tggcgcaatc tcggctcact gcaaactccg cctcccgggt tcacgccatt ctcctgcctc  1380
agcctcccga gtagctggga ctacaggcgc ccgccatcac gcccggctaa tctttttgta  1440
ttttttagtaga gatggggttt caccgtgtgc caggatggtc tcaatctcct gacatcgtga  1500
tctgcccacc tcggcctccc aaagtgctgg gattacagga gtgagccacc gcgcccggcc  1560
tatttaaatg tttttttaatc tagtaaaaa tgagaaaatt gttttttttaa aagtctacct  1620
aatcctacag gctaattaaa gacgtgtgtg gggatcaggt gcggtggttc acacctgtaa   1680
tcccagcact ttggaaggct gatgcaggag gattgcttga gcccaggagt tcaagaccag  1740
cctgggcaag tctctttaaa aaaaacaaaa caaacaaaca aaaaaattag gcatggtggc  1800
acatgcctgt agtcctagct acttaggagg ctgacgtagg aggatcgttt ggacctgaga  1860
ggtcaaggct acagtgagcc atgattgtgc cactgcactc cagcctgggt gacagagtga  1920
gactctgtct caaaaaagaa aaaggaaatc tgtggggttt gttttagttt taagtaattc  1980
taaggacttt aaaaaatgcct agtcttgaca attagatcta tttggcatac aatttgcttg  2040
cttaatctat gtgtgtgcat agatctactg acacacgcat acatataaac attagggaac  2100
taccattctc tttgcgtagg aagccacata tgcctatcta ggcctcagat catacctgat  2160
atgaataggc tttctggata atggtgaaga agatgtataa agatagaac ctatacccat  2220
acatgatttg ttctctagcg tagcaacctg ttacatatta aagttttatt atactacatt  2280
tttctacatc ctttgtttca gggtgttgat tgcctttgct cagtatcttc agcagtgtcc  2340
atttgaagat catgtaaaat tagtgaatga agtaactgaa tttgcaaaaa catgtgttgc  2400
tgatgagtca gctgaaaatt gtgacaaatc acttgtaagt acattctaat tgtggagatt  2460
ctttcttctg tttgaagtaa tcccaagcat ttcaaaggaa ttttttttaa gttttctcaa  2520
ttattattaa gtgtcctgat ttgtaagaaa cactaaaaag ttgctcatag actgataagc  2580
cattgtttct tttgtgatag agatgcttta gctatgtcca cagttttaaa atcatttctt  2640
tattgagacc aaacacaaca gtcatggtgt atttaaatgg caatttgtca tttataaaca  2700
cctcttttta aaatttgagg tttggtttct ttttgtagag ctaatagggg atatgatagc  2760
atgtatttat ttattttatttt atcttatttt attatagtaa gaaccttaa catgagatct  2820
accctgttat atttttaagt gtacaatcca ttattgttaa ctacgggtac actgttgtat  2880
agcttactca tcttgctgta ttaaaacttt gtcccattg attagtaacc cctcgtttcg  2940
tcctcccccca gccactggca accagcatta tactctttga ttctatgagt ttgactactt  3000
tagctacctt atataagtgg tattatgtac tgttatctct tttatgactg acttatttcc  3060
cttagcatag tgcattcaaa gtccaaccat gttgttgcct attgcagaat ttccttcttt  3120
```

```
tcaaggctga ataatattcc agtgcatgtg tgtaccacat tttctttatc cattaatttg   3180
ttgattgata gacatttagg ttggttttct acatcttgac tatcatgaat agtgttgcaa   3240
tgaacacagg agagctacta tctcttagag atgatatcat ggttttttatc atcagaaaac   3300
acccactgat ttctatgcta attttgttac ctgggtggaa taatagtaca gctatatatt   3360
cctcatttta gatatctttg tatttctaca tacaataaaa aagcagagta cttagtcatg   3420
ttgaagaact ttaaactttt agtatttcca gatcaatctt caaaacaagg acaggtttat   3480
cttttctctca ccactcaatc tatatatacc tcttgtgggc aaggccagtt tttatcactg   3540
gagcctttcc cctttttatt atgtacctct ccctcacagc agagtcagga ctttaacttt   3600
acacaatact atggctctac atatgaaatc ttaaaaatac ataaaaatta ataaattctg   3660
tctagagtag tatattttcc ctggggttac agttactttc ataataaaaa ttagagataa   3720
ggaaaggact catttattgg aaagtgattt taggtaacat ttctggaaga aaaatgtcta   3780
tatcttaata gtcacttaat atatgatgga ttgtgttact cctcagtttt caatggcata   3840
tactaaaaca tggccctcta aaaaggggc aaatgaaatg agaactctc tgaatgttat   3900
tctcccctag gtgaattcac ctgctgctta gaagcttatt ttctcttgat ttctgttata   3960
atgattgctc ttaccctta gttttaagtt tcaaaatagg agtcatataa ctttccttaa   4020
agctattgac tgtctttttg tcctgttta ttccaccatga gttatagtgt gacagttaat   4080
tcttatgaaa attatataga gatggttaaa tcatcagaaa ctgtaaacct cgattgggag   4140
gggaagcgga ttttaaaatg atttcctgac caagcttaac cagtatatta aatcctttgt   4200
actgttcttt ggctataaag aaaaaaggta ctgtccagca actgaaacct gcttctcttcc   4260
atttagcata ccctttttgg agacaaatta tgcacagttg caactcttcg tgaaacctat   4320
ggtgaaatgg ctgactgctg tgcaaaacaa gaacctgaga gaaatgaatg cttcttgcaa   4380
cacaaagatg acaacccaaa cctccccccga ttggtgagac cagaggttga tgtgatgtgc   4440
actgctttc atgacaatga agagacattt ttgaaaaagt aagtaatcag atgtttatag   4500
ttcaaaatta aaaagcatgg agtaactcca taggccaaca ctctataaaa attaccataa   4560
caaaatatt ttcaacatta agacttgaa gttttgttat gatgattttt taagaagta   4620
gtatttgata ccacaaaatt ctacacagca aaaaatgaca tcaaagatat tttgaagttt   4680
attgaaacag gatacaatct ttctgaaaaa tttaagatag acaaattatt taatgtatta   4740
cgaagatatg tatatatggt tgttataatt gatttcgttt tagtcagcaa cattatattg   4800
ccaaaattta accatttatg cacacacaca cacacacaca cacacttaac cctttttcc   4860
acatacttaa agaatgacag agacaagacc atcatgtgca aattgagctt aattggttaa   4920
ttagatatct ttggaatttg gaggttctgg ggagaatgtc gattacaatt atttctgtaa   4980
tattgtctgc tatagaaaag tgactgtttt tcttttttcaa aatttagata cttatatgaa   5040
attgccagaa gacatcctta cttttatgcc ccggaactcc ttttctttgc taaaaggtat   5100
aaagctgctt ttacagaatg ttgccaagct gctgataaag ctgcctgcct gttgccaaag   5160
gtattatgca aaagaataga aaaaaagagt tcattatcca acctgatttt gtccattttg   5220
tggctagatt tagggaacct gagtgtctga tacaaacttt ccgacatggt caaaaaagcc   5280
ttcctttat ctgtcttgaa aatctttcat cttttgaaggc ctacactctc gtttcttct   5340
ttaagatttg ccaatgatga tctgtcagag gtaatcactg tgcatgtgtt taaagatttc   5400
accactttt atggtggtga tcactatagt gaaatactga aacttgtttg tcaaattgca   5460
cagcaagggg ccacagttct tgtttatctt ttcatgataa ttttttagtag ggagggaatt   5520
caaagtagag aattttactg catctagatg cctgagttca tgcattcatt ccataaaatat   5580
atattatgga atgcttattt ttcttttctg aggagtttac tgatgttggt ggaggagaga   5640
ctgaaatgaa ttatacacaa aatttaaaaa ttagcaaaat tgcagcccct gggatattag   5700
cgtactcttt ctctgacttt tctcccactt taaggctct ttttcctggc aatgtttcca   5760
gttggttct aactacatag ggaattccgc tgtgaccaga atgatcgaat gatctttcct   5820
tttcttagag agcaaaatca ttattcgcta aagggagtac ttgggaattt aggcataaat   5880
tatgccttca aaatttaatt tggcacagtc tcatctgagc tttaggaggg gtgtttcatg   5940
tagaattttt cttctaattt tcatcaaatt attcctttttt gtagctcgat gaacttcggg   6000
atgaagggaa ggcttcgtct gccaaacaga gactcaagtg tgccagtctc caaaaatttg   6060
gagaaagagc tttcaaagca tggtaaatac ttttaaacat agttggcatc tttataacga   6120
tgtaaatgat aatgcttcag tgacaaattg tacatttta tgtattttgc aaagtgcttg   6180
caaatacatt tctttggttg tctaacaggt agaactcaa tagaggtaaa aatcagaata   6240
tcaatgacaa tttgacatta tttttaatct tttcttttct aaatagttga ataatttaga   6300
ggacgctgtc cttttgtcc taaaaaagg gacagatatt taagttctat ttatttataa   6360
aatcttggac tcttattcta atggttcatt atttttatag agctgtaggc atggttcttt   6420
attttatttt ttaaagttat ttttatttt tgtggataca gagtaggtat acatatttac   6480
ggggtatatg agatatttg atataagtat acaacatata taatcccttt atttaatttt   6540
atcttcccc caatgatcta aaactatttg cttgtccttt tatgtcttat agttaaattc   6600
agtcaccaac taagttgaag ttacttctta tttttgcata gctccagctc tgatctttcat   6660
ctcatgtttt tgcctgagcc tctgttttca tattacttag ttggttctgg gagcatactt   6720
taatagccga gtcaagaaaa atactagctg ccccgtcacc cacactcctc acctgctagt   6780
caacagcaaa tcaacacaac aggaaataaa atgaaaataa tagacattat gcatgctctc   6840
tagaaactgt caattgaact gtatttgctc atcattccta ccatctacac caccaaaatc   6900
aaccaaattt atgaaaaaaa acagcccccaa cataaaatta tacacagata aacaggctat   6960
gattggtttt gggaaagaag tcaccttac ctgatttagg caactgtgaa atgactagag   7020
aatgaagaaa attagacgtt tacatcttgt catagagttt gaagatagtg ctggatcttt   7080
ctttttataa gtaagatcaa taaaaactcc ctcattctgt agaagttatg atttctttc   7140
taagagacct ttagaagtca gaaaaaatgt gtttcaattg agaaaaaaga taactggagt   7200
ttgtgtagta cttcccagat tataaaatgc tttgtatgt attatctaat ttaatcctca   7260
aaacttcttc aatttagcat gttgtcatga cactgcagag gctgaagctc agagaggctg   7320
agccctctgc taacaagtcc tactgctaac aagtgataaa gccagagctg gaagtcacat   7380
ctggactcca aacctgatgc ttctcagcct gttgccccctt ttagagttcc ttttttaattt   7440
ctgctttta gacttgctag attctacct accacacaca ctcaaaatg gataattctg   7500
ccctaaggat aagtgattac catttggttc agaactaga ctaatgaatt ttaaaaatta   7560
tttctgtatg tccatttga atttttctat gagaaatagt atttgcctag tgttttcata   7620
taaaatatcg catgataata ccatttttgat tggcgatttt cttttaggg cagtagctcg   7680
cctgagccag agatttccca aagctgagtt tgcagaagtt tccaagttag tgacagatct   7740
taccaaagtc cacacggaat gctgccatgg agatctgctt gaatgctgtg atgacagggt   7800
aaagagtcgt cgatatgctt tttggtagct tgcatgctca agttggtaga atgatggcgt   7860
```

-continued

```
ttggtatcat tggtgatagc tgacagtggg ttgagattgt cttctgtgct ttcgtctgtc   7920
ctatcttcaa tctttccctg cctatggtgg tggtaccttt ctgttttaa cctggctata    7980
aattaccaga taaacccatt cactgatttg taactccttt cagtcatgct ctaactgtaa   8040
atgaaggctt aaactgaagt agaacagtta caaggtttta cttggcagaa catcttgcaa   8100
ggtagatgtc taagaagatt ttttttttctt ttttaagac agagtttcgc tcttgtttcc   8160
caggctgggg tgcaatggtg tgatcttggc tcagcgcaac ctctgcctcc tgggttcaag   8220
tgattctcat gcctcagcct cccaagtagc tgggattaca ggcatgcgcc accacacctg   8280
gctaattttg tattttagt agaggcgggg tttcaccata ttgtccagac tggtctcgaa    8340
ctcctgacct caggtgatcc acccgccttg gcctcccaaa gtgctgggat tacaggcatg   8400
agccaccttg cccagcctaa gaagatttt tgagggaggt aggtggactt ggagaaggtc    8460
actacttgaa gagattttg gaatgatgt attttcttc tctatattcc ttcccttaat      8520
taactctgtt tgttagatgt gcaaatattt ggaatgatat ctcttttctc aaaacttata   8580
atattttctt tctcccttc ttcaagatta aacttatggg caaatactag aatcctaatc    8640
tctcatggca ctttctggaa aatttaaggc ggttatttta tatatgtaag caggggcctat  8700
gactatgatc ttgactcatt tttcaaaaat cttctatatt ttatttagtt atttggtttc   8760
aaaaggcctg cacttaattt tgggggatta tttggaaaaa cagcattgag ttttaatgaa   8820
aaaaacttaa atgccctaac agtagaaaca taaaattaat aaataactga ctgagcacc    8880
tgctactgat tagtctattt taattaagtg ggaatgtttt tgtagtccta tctacatctc   8940
caggtttagg agcaaacaga gtatgttcat agaaggaata tgtgtatggt cttagaaatc   9000
aatgaatatg ttctgccaac ttaataaagg tctgaggaga aagtgtagca atgtcaattc   9060
gtgttgaaca atttccacca acttacttat aggcggacct tgccaagtat atctgtgaaa   9120
atcaagattc gatctccagt aaaactgaagg aatgctgtga aaaacctctg ttggaaaaat  9180
cccactgcat tgccgaagtg gaaaatgatg agatgcctgc tgacttgcct tcattagctg   9240
ctgattttgt tgaaagtaag gatgtttgca aaaactatgc tgaggcaaag gatgtcttcc   9300
tgggcatgta agtagataag aaattattct tttatagctt tggcatgacc tcacaactta   9360
ggaggatagc ctaggctttt ctgtggagtt gctacaattt ccctgctgcc cagaatgttt   9420
cttcatcctt cccttttccca ggctttaaca atttttgaaa tagttaatta gttgaataca   9480
ttgtcataaa ataatacatg ttcatggcaa agctcaacat tccttactcc ttaggggtat   9540
ttctgaaaat acgtctagaa acattttgtg tatatataaa ttatgtatac ttcagtcatt   9600
cattccaagt gtatttcttg aacatcatata atatatgtgc gtgactatgt attgcctgtc   9660
tatctaacta atctaatcta atcagtctca tctatctaat ctatgcaatg atagcaaaga   9720
agtataaaaa gaaatataga gtctgacacc aggtgcttta tatttggtga aaagaccaga   9780
agttcagtat aatggcaata tggtaggcaa ctcaattaca aaataaatgt ttacatattg   9840
tcagaagttg tggtgataaa ctgcattttt gttgttggat tgtgataatg cactaaaataa   9900
tatttcctaa aattatgtac cctacaagat ttcactcata cagagaagaa agagaatatt   9960
ttaagaacat atctctgccc atctatttat cagaatcctt ttgagatgta gtttaaatca  10020
aacaaaatgt taataaaaat aacaagtatc attcatcaaa gacttcatat gtgccaagca  10080
gtgtgtgctt tgtgtagatt atgtcatata gttctcataa tccaccttcc gagacagata  10140
ctatttattt tttgagacag agttttactc ttgttgccca ggctggagtg caatggtgcc  10200
atctcggctc accacaacct ccgcctccca ggttcaagcg attctcctgc ctcagcctcc  10260
tgggattaca ggcatgcacc accatgcctg gctaattttg tattttagt agagatgggg   10320
tttcaccatg ttggtcagac tggtctcaaa ctcctgacct ctggtgatat gcctgcctca  10380
gcctcctaaa gtgctgggat tacaggcatg agccactgtg cccagccgac agatactatt  10440
attatttcca ttctaccgag aaggagacta aggctctgat catttaaata agttgcctaa  10500
ggtgatgcag tgatataagt agcagagcta ggaattgagc cttggtaact ttaactctgg  10560
accccaagtc cttagctact aagctttact gcatgggggtt tagtcaaatt aagacttttg  10620
gaatatgagt tacttttgag attacttttg tgatattttt tgtgctcatt tgtccaacaa  10680
agtctatttt attttcatct taattaggtt tttgtatgaa tatgcaagaa ggcatcctga  10740
ttactctgtc gtgctgctgc tgagacttgc caagacatat gaaaccactc tagagaagtg  10800
ctgtgccgct gcagatcctc atgaatgcta tgccaaagtg gtaggttat tgttggaaaa   10860
aaatgtattt ctttgactga tgattccaat aatgagaaag aaaaataatg caagaatgta  10920
aaatgatata cagtgcaatt tagatctttt cttgagatgg tttcaattct ggaatcttaa  10980
acatgaaaga aaaagtagcc ttagaatgat taacaaaatt tagactagtt agaatagaaa  11040
gatctgaata gagcaatctc taaaaaattt tgatctttt ttctcttttt cacaatcctg   11100
agaacaaaaa aaaattaaat ttaaatgtta attagaagat atttaactta gatgtaaagt  11160
gagttaaacct gattccagga ttaatcaagt actagaatta gtatcttatg gcaaattata  11220
gaacctatcc ctttagaata ttttcaaatc ttttgagga tgtttaggaa tagttttaca   11280
agaaattaag ttaggagagg aaatctgttc tggaggattt taggttcc cactagcata    11340
tgtaatggtt tctgaactat tcagaatcag agaaaactca ttttcctgc tttcaagaag   11400
ctactgtatg ccaggcacca tgcacaaaca atgaccaacg taaatctct cattttggag    11460
agcctggaat ctaactggaa aggtgaacta ataataataa tatgtacaat catagccatc  11520
atttattaaa cttttattat atgcaaggca ctgtttaatt tcattagctt acctggttta  11580
cagagcagct ctatgagatg agtgccatct tgcccctat tttagggata aggattctga   11640
aatgtggaga tggtaagtaa aattgcacaa ctgaagaatg agttacatga cttggctcaa  11700
atactggtca ttgaactcca gagcctgaat attcttaacc acttacatga tgcaagctca  11760
ccaaataaat agttcgaatg tattgtgaca gagcggcatt gatattcatc tattcatgtg  11820
gctttgagta ggaagaagaa aggatatcat tctgaccaga ggggtgaaaa acaacctgca  11880
tctgatcctg aggcataata ctattaacac aattcttta tgtttcagtt cgataatttt   11940
aaacctcttg tggaagagcc tcagaattta atcaaacaaa attgtggct tttgagcag    12000
cttggagagt acaaattcca gaatgcgtaa gtaatttta ttgactgatt tttttttatca   12060
atttgtaatt atttaagact taatatatga gccacctagc ataagacttt taagaatgaa  12120
aatacattgc atatttctaa tcactctttg tcaagaaaga taggagagga gagataaaat  12180
agttgatggg gtggagaggt ctatatttga atgtagtcta aaaattgttc tctaagatt   12240
ggaagtatgt aggctgggag ggtaaataccc aaatcttatg atatcagaac tgagcatgtc  12300
ccttgaaggt taagaaatag ttaatgggca aatagagcat ggcaatattt tgtgagcag   12360
caagtagtag gccttgaata gatgtcgctc aaaaagtaat atgtaagctg aacacaaaaa  12420
tgtaacaaat gaatttagat acatatttga atattaaatt caggttgttt gggagatgca  12480
cctagtcttt gatggttaaa cctttccctc catagaaagag acagagacag aatggcttgc  12540
tggactaatg tcccaattca atagagtctt atctatgaag gttaaaaaca agaagagaca  12600
```

```
tattatacag tagatattta ttgtgtggct catacacatg gtgctcttct gattatggat    12660
tttagagata ataacagtga acaagacata gtttctttcc tcgagtagat taaagtcata    12720
cattgacttt taatggtgac tggcattctt aatacatgat tattatatat taggtaccat    12780
gtcagattaa ttataatact ttactacttt taatttaacc cttgaactat ccctattgag    12840
tcagatatat ttccttccat tttctacttg tatctttcaa gtttagcata tgctgataca    12900
tatgaagctc tctccaggtt ttattgaaag aagaaattaa taaatttatt aatgtcactg    12960
aattaggcaa ctcactttcc caagattatg caagtggtac aggtggaact caaagccaag    13020
tttaactagt tgttcaggag aatgttttct accctccact aacccactac tctgcagatg    13080
gagataatat gatgaatgga acatagcaac atcttagttg attccggcca agtgttctct    13140
gttttatcta ctatgttaga cagtttcttg ccttgctgaa aacacatgac ttctttttttt   13200
caggctatta gttcgttaca ccaagaaagt accccaagtg tcaactccaa ctcttgtaga    13260
ggtctcaaga aacctaggaa aagtgggcag caaatgttgt aaacatcctg aagcaaaaag    13320
aatgccctgt gcagaagact atgtgagtct ttaaaaaaat ataataaatt aataatgaaa    13380
aaattttacc tttagatatt gataatgcta gctttcataa gcagaaggaa gtaatgtgtg    13440
tgtgtgcatg tttgtgtgca tgtgtgtgtg catgcacgtg tgtgtatgtg tgatattggc    13500
agtcaaggcc ccgaggatga taattttttt tttttttttg agacggagtc tcgctttgtt    13560
gtccaggctg gagtgcagtg gtgccatctc ggctcactgc aacctccgcc tcccaggttc    13620
aagccattct cctgcctcag cctcccaagt agctgggact acaggtgcat gccaccatgc    13680
ctggctaatt ttttgtattt ttagtagaaa attttcagct tcacctcttt tgaatttctg    13740
ctctcctgcc tgttctttag ctatccgtgg tcctgaacca gttatgtgtg ttgcatgaga    13800
aaacgccagt aagtgacaga gtcaccaaat gctgcacaga atccttggtg aacaggcgac    13860
catgcttttc agctctggaa gtcgatgaaa catacgttcc caaagagttt aatgctgaaa    13920
cattcacctt ccatgcagat atatgcacac tttctgagaa ggagagacaa atcaagaaac    13980
aaacgtgagg agtatttcat tactgcatgt gtttgtagtc ttgatagcaa gaactgtcaa    14040
ttcaagctag caacttttttc ctgaagtagt gattatattt cttagaggaa agtattggag    14100
tgttgcccctt attatgctga taagagtacc cagaataaaa tgaataactt tttaaagaca    14160
aaatcctctg ttataatatt gctaaaatta ttcagagtaa tattgtggat taaagccaca    14220
atagaataac atgttaggcc atattcagta gaaaaagatg aacaattaac tgataaattt    14280
gtgcacatgg caaattagtt aatgggaacc ataggagaat ttatttctag atgtaaataa    14340
ttatttttaag tttgccctat ggtggcccca cacatgacaa aaaccccccaa gatgtgactt   14400
ttgagaatga gacttggata aaaaacatgt agaaatgcaa gccctgaagc tcaactccct    14460
attgctatca caggggttat aattgcataa aatttagcta tagaaagttg ctgtcatctc    14520
ttgtgggctg taatcatcgt ctaggcttaa gagtaatatt gcaaacctg tcatgcccac     14580
acaaatctct ccctggcatt gttgtctttg cagatgtcag tgaaagagaa ccagcagctc    14640
ccatgagttt ggatagcctt attttctata gcctccccac tattagcttt gaaggggagca   14700
aagtttaaga accaaatata aagtttctca tctttataga tgagaaaaat tttaaataaa    14760
gtccaagata attaaatttt taaggatcat ttttagctct ttaatagcaa taaaactcaa    14820
tatgacataa tatggcactt ccaaaatctg aataatatat aattgcaatg acatacttct    14880
tttcagagat ttactgaaaa gaaatttgtt gacactacat aacgtgatga gtggtttata    14940
ctgattgttt cagttggtct tcccaccaac tccatgaaag tggatttat tatcctcatc      15000
atgcagatga gaatattgag acttatagcg gtatgcctga gccccaaagt actcagagtt    15060
gcctggctcc aagatttata atcttaaatg atgggactac catccttact ctctccattt    15120
ttctatacgt gagtaatgtt ttttcgtttt ttttttttttc ttttccatt caaactcagt    15180
gcacttgttg agctcgtgaa acacaagccc aaggcaacaa aagagcaact gaaagctgtt    15240
atggatgatt tcgcagcttt tgtagagaag tgctgcaagg ctgacgataa ggagacctgc    15300
tttgccgagg aggtactaca gttctcttca ttttaatatg tccagtattc attttttgcat   15360
gtttggttag gctagggctt agggatttat atatcaaagg aggctttgta catgtgggac    15420
agggatctta ttttacaaac aattgtctta caaaatgaat aaaaacagcac tttgtttta    15480
tctcctgctc tattgtgcca tactgttaaa tgtttataat gcctgttctg tttccaaatt    15540
tgtgatgctt atgaatatta ataggaatat ttgtaaggcc tgaaatattt tgatcatgaa    15600
atcaaaacat taattttttt aaacatttac ttgaaatgtg gtggttttgtg atttagttga    15660
ttttataggc tagtgggaga atttacattc aaatgtctaa atcacttaaa attgcccttt    15720
atggcctgac agtaacttttt ttttattcat ttggggacaa ctatgtccgt gagcttccgt    15780
ccagagatta tagtagtaaa ttgtaattaa aggatatgat gcacgtgaaa tcactttgca    15840
atcatcaata gcttcataaa tgttaatttt gtatcctaat agtaatgcta atattttcct    15900
aacatctgtc atgtctttgt gttcagggta aaaaacttgt tgctgcaagt caagctgcct    15960
taggcttata acatcacatt taaaagcatc tcaggtaact atatttttgaa ttttttaaaa   16020
aagtaactat aatagttatt attaaaatag caaagattga ccattccaa gagccatata     16080
gaccagcacc gaccactatt ctaaactatt tatgtatgta aatattagct tttaaaattc    16140
tcaaaatagt tgctgagttg ggaaccacta ttatttctat tttgtagatg agaaaatgaa    16200
gataaacatc aaagcataga ttaagtaatt ttccaaaggg tcaaaattca aaattgaaac    16260
caaagtttca gtgttgccca ttgtcctgtt ctgacttata tgatgcggta cacagagcca    16320
tccaagtaag tgatggctca gcagtggaat actctgggaa ttaggctgaa ccacatgaaa    16380
gagtgcttta tagggcaaaa acagttgaat atcagtgatt tcacatggtt caacctaata    16440
gttcaactca tccttttccat tggagaatat gatggatcta ccttctgtga actttatagt    16500
gaagaatctg ctattacatt tccaatttgt caacatgctg agctttaata ggacttatct    16560
tcttatgaca acatttattg gtgtgtcccc ttgcctagcc caacagaaga attcagcagc    16620
cgtaagtcta ggacaggctt aaattgtttt cactggtgta aattgcagaa agatgatcta    16680
agtaatttgg catttatttt aataggtttg aaaaacacat gccattttac aaataagact    16740
tatatttgtc cttttgtttt tcagcctacc atgagaataa gagaaagaaa atgaagatca    16800
aaagcttatt catctgttttt tcttttttcgt tggtgtaaag ccaacaccct gtctaaaaaa   16860
cataaatttc tttaatcatt ttgcctcttt tctctgtgct tcaattaata aaaaatggaa    16920
agaatctaat agagtggtac agcactgtta tttttcaaag atgtgttgct atcctgaaaa    16980
ttctgtaggt tctgtggaag ttccagtgtt ctctcttatt ccacttcggt agaggatttc    17040
tagtttcttg tgggctaatt aaataaaatca ttaatactct tctaagttat ggattataaa    17100
cattcaaaat aatattttga cattatgata attctgaata aaagaacaaa accatggta      17160
taggtaagga atataaaaca tggctttttac cttagaaaaa acaattctaa aattcatatg    17220
gaatcaaaaa agagcctgca gaaccaaagt aagactaagc aaaaagaaca aattacctga    17280
tttcaaacta cactataagg ccatagtcac cgaaacagca aggtactggt ataaa         17335
```

```
SEQ ID NO: 36          moltype = DNA  length = 2076
FEATURE                Location/Qualifiers
source                 1..2076
                       mol_type = other DNA
                       organism = Mus musculus
SEQUENCE: 36
atattagagc gagtctttct gcacacagat cacctttcct atcaacccca ctagcctctg    60
gcaaaatgaa gtgggtaacc tttctcctcc tcctcttcgt ctccggctct gcttttttcca  120
ggggtgtgtt tcgccgagaa gcacacaaga gtgagatcgc ccatcggtat aatgatttgg   180
gagaacaaca tttcaaaggc ctagtcctga ttgccttttc ccagtatctc cagaaatgct   240
catacgatga gcatgccaaa ttagtgcagg aagtaacaga ctttgcaaag acgtgtgttg   300
ccgatgagtc tgccgccaac tgtgacaaat cccttcacac tcttttttgga gataagttgt  360
gtgccattcc aaacctccgt gaaaactatg gtgaactggc tgactgctgt acaaaacaag   420
agcccgaaag aaacgaatgt ttcctgcaac acaaagatga caaccccagc ctgccaccat   480
ttgaaaggcc agaggctgag gccatgtgca cctcctttaa ggaaacccca accacctta    540
tgggacacta tttgcatgaa gttgccgaaa gacatcctta tttctatgcc ccagaacttc   600
tttactatgc tgagcagtac aatgactcc tgacccagtg ttgtgcagag gctgacaagg    660
aaagctgcct gaccccgaag cttgatggtg tgaaggagaa agcattggtc tcatctgtcc   720
gtcagagaat gaagtgctcc agtatgcaga agtttggaga gagagctttt aaagcatggg   780
cagtagctcg tctgagccag acattcccca atgctgactt tgcagaaatc accaaattgg   840
caacagacct gaccaaagtc aacaaggagt gctgccaatgg tgacctgctg gaatgcgcag   900
atgacagggc ggaacttgcc aagtacatgt gtgaaaacca ggcgactatc tccagcaaac   960
tgcagacttg ctgcgataaa ccactgttga agaaagccca ctgtcttagt gaggtggagc  1020
atgacaccat gcctgctgat ctgcctgcca ttgctgctga ttttgttgag gaccaggaag  1080
tgtgcaagaa ctatgctgag gccaaggatg tcttcctggg cacgttcttg tatgaatatt  1140
caagaagaca ccctgattac tctgtatccc tgttgctgag acttgctaag aaatatgaag  1200
ccactctgga aaagtgctgc gctgaagcca atcctcccgc atgctacggc acagtgcttg  1260
ctgaatttca gcctcttgta gaagagccta gaacttggt caaaaccaac tgtgatcttt  1320
acgaaagct tggagaatat ggattccaaa atgccattct agttcgctac acccagaaag  1380
cacctcaggt gtcaacccca actctcgtgg aggctgcaag aaacctagga agagtgggca  1440
ccaagtgttg tacacttcct gaagatcaga gactgccttg tgtggaagac tatctgtctg  1500
caatcctgaa ccgtgtgtgt ctgctgcatg agaagacccc agtgagtgag catgttacca  1560
agtgctgtag tggatcctg gtggaaaggc ggccatgctt ctctgctctg acagttgatg  1620
aaacatatgt cccccaaagag tttaaagctg agaccttcac cttccactct gatatctcga  1680
cacttccaga gaaggagaag cagattaaga acaaacggc tcttgctgag ctggtgaagc  1740
acaagcccaa ggctacagcg gagcaactga agactgtcat ggatgacttt gcacagttcc  1800
tggatacatg ttgcaaggct gctgacaagg acacctgctt ctcgactgag ggtccaaacc  1860
ttgtcactag atgcaaagac gccttagcct aaacacatca caaccacaac cttctcaggc  1920
taccctgaga aaaaagaca tgaagactca ggactcatct tttctgttgg tgtaaaatca   1980
acaccctaag gaacacaaat ttcttttaaac atttgacttc ttgtctctgt gctgcaatta  2040
ataaaaaatg gaaagaatct aaaaaaaaaa aaaaaa                             2076

SEQ ID NO: 37          moltype = DNA  length = 2285
FEATURE                Location/Qualifiers
source                 1..2285
                       mol_type = other DNA
                       organism = Homo sapiens
SEQUENCE: 37
ctagcttttc tcttctgtca acccacacg cctttggcac aatgaagtgg gtaacctta     60
tttcccttct ttttctcttt agctcggctt attccaggg tgtgtttcgt cgagatgcac   120
acaagagtga ggttgctcat cggttaaag atttgggaga agaaaattc aaagccttga    180
tgttgattgc ctttgctcag tatcttcagc agtgtccatt tgaagatcat gtaaaattag   240
tgaatgaagt aactgaattt gcaaaaacat gtgttgctga tgagtcagct gaaaaattgtg   300
acaaatcact tcatacccct tttggagaca aattatgcac cattgcttaact cttcgtgaaa  360
cctatggtga aatggctgac tgctgtgcaa aacaagaacc tgagagaaat gaatgcttct   420
tgcaacacaa agatgacaac ccaaacctcc ccgattggt gagaccagag ttgatgtga    480
tgtgcactgc ttttcatgac aatgaagaga catttttgaa aaatactta tatgaaattg   540
ccagaagaca tccttacttt tatgcccgg aactccttt ctttgctaaa aggtataaag   600
ctgctttac agaatgttgc caagctgctg ataaagctgc ctgcctgttg ccaaagctca   660
atgaacttcg ggatgaaggg aaggcttcgt ctgccaaaca gagactcaag tgtgccagtc   720
tccaaaaatt tggagaagaa gctttcaaag catgggcagt agctcgcctg agccagagat   780
ttcccaaagc tgagtttgca gaagtttcca agttagtgac agatcttacc aaagtccaca   840
cggaatgctg ccatggagat ctgcttgaat gtgctgatga cagggcggac cttgccaagt   900
atatctgtga aaatcaagat tcgatctcca gtaaactgaa ggaatgctgt gaaaaacctc   960
tgttggaaaa atcccactgc attgccgaag tggaaaatga tgagatgcct gctgacttgc  1020
cttcattagc tgctgatttt gttgaaagta aggatgtttg caaaaactat gctgaggcaa  1080
aggatgtctt cctgggcatg ttttttgtatg aatatgcaag aaggcatcct gattactgtv  1140
tcgtctgtct gctgagactt gccaagacat atgaaaccac tctagagaag tgctgccgg   1200
ctgcagatcc tcatgaatgc tatgccaaag tgttcgatga attaaaccct cttgtggaag  1260
agcctcagaa tttaatcaaa caaaattgtg agctttttga gcagcttgga gagtacaat   1320
tccagaatgc gctattagtt cgttacacca gaaagtacc ccagtgtca actccaactc   1380
ttgtagaggt ctcaagaaac ctaggaaaag tggggcagcaa atgttgtaaa catcctgaag  1440
caaaagaat gccctgtgca gaagactatc tatccgtggt cctgaaccag ttatgtgttg   1500
tgcatgagaa aacgcccagta agtgacagag tcaccaaaatg ctgcacagaa tcctgggtga  1560
acaggcgacc atgctttcca gctctggaag tcgatgaaac atcgttcccc aaagagttta  1620
atgctgaaac attcacctc catgcagata tatgcacact ttctgaagag gagacaaa    1680
tcaagaaaca aactgcactt gttgagctcg tgaaaacaca gcccaaggca caaaagagc   1740
aactgaaagc tgttatggat gatttcgcag cttttgtaga gaagtgctgc aaggctgacg   1800
```

-continued

```
ataaggagac ctgctttgcc gaggagggta aaaaacttgt tgctgcaagt caagctgcct    1860
taggcttata acatcacatt taaaagcatc tcagcctacc atgagaataa agaaagaaaa    1920
atgaagatca aaagcttatt catctgtttt tcttttttcgt tggtgtaaag ccaacaccct    1980
gtctaaaaaa cataaatttc tttaatcatt ttgcctcttt tctctgtgct tcaattaata    2040
aaaaatggaa agaatctaat agagtggtac agcactgtta tttttcaaag atgtgttgc     2100
atcctgaaaa ttctgtaggt tctgtggaag ttccagtgtt ctctcttatt ccacttcggt    2160
agaggatttc tagtttcttg tgggctaatt aaataaatca ttaatactct tctaagttat    2220
ggattataaa cattcaaaat aatattttga cattatgata attctgaata aagaacaaa     2280
aacca                                                                2285
```

| | | |
|---|---|---|
| SEQ ID NO: 38 | moltype = AA   length = 1391 | |
| FEATURE | Location/Qualifiers | |
| REGION | 1..1391 | |
| | note = Synthetic | |
| REGION | 4..10 | |
| | note = MISC_FEATURE - 5' NLS | |
| REGION | 1376..1391 | |
| | note = MISC_FEATURE - 3' NLS | |
| source | 1..1391 | |
| | mol_type = protein | |
| | organism = synthetic construct | |

SEQUENCE: 38

```
MDKPKKKRKV KYSIGLDIGT NSVGWAVITD EYKVPSKKFK VLGNTDRHSI KKNLIGALLF     60
DSGETAEATR LKRTARRRYT RRKNRICYLQ EIFSNEMAKV DDSFFHRLEE SFLVEEDKKH    120
ERHPIFGNIV DEVAYHEKYP TIYHLRKKLV DSTDKADLRL IYLALAHMIK FRGHFLIEGD    180
LNPDNSDVDK LFIQLVQTYN QLFEENPINA SGVDAKAILS ARLSKSRRLE NLIAQLPGEK    240
KNGLFGNLIA LSLGLTPNFK SNFDLAEDAK LQLSKDTYDD DLDNLLAQIG DQYADLFLAA    300
KNLSDAILLS DILRVNTEIT KAPLSASMIK RYDEHHQDLT LLKALVRQQL PEKYKEIFFD    360
QSKNGYAGYI DGGASQEEFY KFIKPILEKM DGTEELLVKL NREDLLRKQR TFDNGSIPHQ    420
IHLGELHAIL RRQEDFYPFL KDNREKIEKI LTFRIPYYVG PLARGNSRFA WMTRKSEETI    480
TPWNFEEVVD KGASAQSFIE RMTNFDKNLP NEKVLPKHSL LYEYFTVYNE LTKVKYVTEG    540
MRKPAFLSGE QKKAIVDLLF KTNRKVTVKQ LKEDYFKKIE CFDSVEISGV EDRFNASLGT    600
YHDLLKIIKD KDFLDNEENE DILEDIVLTL TLFEDREMIE ERLKTYAHLF DDKVMKQLKR    660
RRYTGWGRLS RKLINGIRDK QSGKTILDFL KSDGFANRNF MQLIHDDSLT FKEDIQKAQV    720
SGQGDSLHEH IANLAGSPAI KKGILQTVKV VDELVKVMGR HKPENIVIEM ARENQTTQKG    780
QKNSRERMKR IEEGIKELGS QILKEHPVEN TQLQNEKLYL YYLQNGRDMY VDQELDINRL    840
SDYDVDHIVP QSFLKDDSID NKVLTRSDKN RGKSDNVPSE EVVKKMKNYW RQLLNAKLIT    900
QRKFDNLTKA ERGGLSELDK AGFIKRQLVE TRQITKHVAQ ILDSRMNTKY DENDKLIREV    960
KVITLKSKLV SDFRKDFQFY KVREINNYHH AHDAYLNAVV GTALIKKYPK LESEFVYGDY   1020
KVYDVRKMIA KSEQEIGKAT AKYFFYSNIM NFFKTEITLA NGEIRKRPLI ETNGETGEIV   1080
WDKGRDFATV RKVLSMPQVN IVKKTEVQTG GFSKESILPK RNSDKLIARK KDWDPKKYGG   1140
FDSPTVAYSV LVVAKVEKGK SKKLKSVKEL LGITIMERSS FEKNPIDFLE AKGYKEVKKD   1200
LIIKLPKYSL FELENGRKRM LASAGELQKG NELALPSKYV NFLYLASHYE KLKGSPEDNE   1260
QKQLFVEQHK HYLDEIIEQI SEFSKRVILA DANLDKVLSA YNKHRDKPIR EQAENIIHLF   1320
TLTNLGAPAA FKYFDTTIDR KRYTSTKEVL DATLIHQSIT GLYETRIDLS QLGGDKRPAA   1380
TKKAGQAKKK K                                                       1391
```

| | | |
|---|---|---|
| SEQ ID NO: 39 | moltype = DNA   length = 4176 | |
| FEATURE | Location/Qualifiers | |
| misc_feature | 1..4176 | |
| | note = Synthetic | |
| misc_feature | 1..3 | |
| | note = Start Codon | |
| misc_feature | 10..30 | |
| | note = 5' NLS | |
| misc_feature | 4126..4173 | |
| | note = 3' NLS | |
| misc_feature | 4174..4176 | |
| | note = Stop Codon | |
| source | 1..4176 | |
| | mol_type = other DNA | |
| | organism = synthetic construct | |

SEQUENCE: 39

```
atggacaagc ccaagaaaaa gcggaaagtg aagtacagca tcggcctgga catcggcacc     60
aactctgtgg gctgggccgt gatcaccgac gagtacaagg tgcccagcaa gaaattcaag    120
gtgctgggca acaccgacag gcacagcatc aagaagaacc tgatcggcgc cctgctgttc    180
gacagcggcg aaacagccga ggccaccaga ctgaagagaa ccgccagaag aagatacacc    240
aggcggaaga acaggatctg ctatctgcaa gagatcttca gcaacgagat ggccaaggtg    300
gacgacagct tcttccacag actggaagag tccttcctgg tggaagagga caagaagcac    360
gagagacacc ccatcttcgg caacatcgtg gacgaggtgg cctaccacga agtgtaccc     420
accatctacc acctgagaaa gaaactggtg gacagcaccg acaaggccga cctgagactg    480
atctacctgg ccctggccca catgatcaag ttcagaggcc acttcctgat cgagggcgac    540
ctgaaccccg acaacagcga cgtggacaag ctgttcatcc agctggtgca gacctacaac    600
cagctgttcg aggaaaaccc catcaacgcc agcggcgtgg acgccaaggc tatcctgtct    660
gccagactga gcaagagcag aaggctggaa aatctgatcg cccagctgcc cggcgagaag    720
aagaacggcc tgttcggcaa cctgattgcc ctgagcctgg gcctgacccc caacttcaag    780
agcaacttcg acctggccga ggatgccaaa ctgcagctga gcaaggacac ctacgacgac    840
gacctggaca acctgctggc ccagatcggc gaccagtacg ccgacctgtt cctggccgcc    900
aagaacctgt ctgacgccat cctgctgagc gacatcctga gagtgaacac cgagatcacc    960
```

```
aaggcccccc tgagcgcctc tatgatcaag agatacgacg agcaccacca ggacctgacc   1020
ctgctgaaag ctctcgtgcg gcagcagctg cctgagaagt acaaagaaat cttcttcgac   1080
cagagcaaga acggctacgc cggctacatc gatggcggcg ctagccagga agagttctac   1140
aagttcatca agcccatcct ggaaaagatg gacggcaccg aggaactgct cgtgaagctg   1200
aacagagagg acctgctgag aaagcagaga accttcgaca acggcagcat cccccaccag   1260
atccacctgg gagagctgca cgctatcctg agaaggcagg aagattttta cccattcctg   1320
aaggacaacc gggaaaagat cgagaagatc ctgacctcca ggatcccta ctacgtgggc   1380
cccctggcca gaggcaacag cagattcgcc tggatgacca gaaagagcga ggaaaccatc   1440
accccctgga acttcgagga agtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaaa tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat tcaacgcctc cctgggcaca   1800
taccacgatc tgctgaaaat tatcaaggac aaggacttcc tggataacga agagaacgag   1860
gacattctgg aagatatcgt gctgaccctg acactgtttg aggaccgcga gatgatcgag   1920
gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca agacaatcct ggatttcctg aagtccgacg gcttcgccaa ccggaacttc   2100
atgcagctga tccacgacga cagcctgaca ttcaaagagg acatccagaa agcccaggtg   2160
tccgccaggc gcgactctct gcacgagcat atcgctaacc tggccggcag ccccgctatc   2220
aagaaggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg gcatcaaaga gctgggcagc   2400
cagatcctga agaacacccc cgtggaaaac acccagctgc agaacgagaa gctgtacctg   2460
tactacctgc agaatgggcg ggatatgtac gtggaccaaga aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gccctccgaa   2640
gaggtcgtga gaagatgaa gaactactgg cgacagctgc tgaacgccaa gctgattacc   2700
cagaggaagt tcgataacct gaccaaggcc gagagggcct gagcgctgataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtacccaaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aactttttca gaccgaaat caccctggcc   3180
aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca aagagtctat cctgcccaag   3360
aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
tccaagaaac tgaagagtgt gaaagagctg ctggggatca ccatcatgga agaagcagc   3540
tttgagaaga accctatcga ctttctggaa gccaagggct acaaagaagt gaaaaaggac   3600
ctgatcatca agctgcctaa gtactccctg ttcgagctgg aaaacggcag aaagagaatg   3660
ctggcctctc ccgggcaact gcagaaggga acgagctgcc cctgcctag caaatatgtg   3720
aacttcctgt acctggcctc ccactatgag aagctgaagg gcagccctga ggacaacgaa   3780
cagaaacagc tgtttgtgga acagcataag cactaccggtg acgagatcat cgagcagatc   3840
agcgagttct ccaagagagt gatcctggcc gacgccaatc tggacaaggt gctgtctgcc   3900
tacaacaagc acagggacaa gcctatcaga gagcaggccg agaatatcat ccacctgttc   3960
accctgacaa acctgggcgc tcctgccgcc ttcaagtact tgaccaccat catcgaccgg   4020
aagaggtaca ccagcaccaa agaggtgctg gacgccaccc tgatccacca gagcatcacc   4080
ggcctgtacg agacaagaat cgacctgtct cagctgggag gcgacaagag acctgccgcc   4140
actaagaagg ccggacaggc caaaaagaag aagtga                             4176

SEQ ID NO: 40         moltype = RNA   length = 16
FEATURE               Location/Qualifiers
misc_feature          1..16
                      note = Synthetic
source                1..16
                      mol_type = other RNA
                      organism = synthetic construct
SEQUENCE: 40
gttttagagc tatgct                                                   16

SEQ ID NO: 41         moltype = RNA   length = 67
FEATURE               Location/Qualifiers
misc_feature          1..67
                      note = Synthetic
source                1..67
                      mol_type = other RNA
                      organism = synthetic construct
SEQUENCE: 41
agcatagcaa gttaaaataa ggctagtccg ttatcaactt gaaaaagtgg caccgagtcg   60
gtgcttt                                                             67

SEQ ID NO: 42         moltype = RNA   length = 77
FEATURE               Location/Qualifiers
misc_feature          1..77
```

```
                        note = Synthetic
source                  1..77
                        mol_type = other RNA
                        organism = synthetic construct
SEQUENCE: 42
gttttagagc tagaaatagc aagttaaaat aaggctagtc cgttatcaac ttgaaaaagt    60
ggcaccgagt cggtgct                                                  77

SEQ ID NO: 43           moltype = RNA   length = 82
FEATURE                 Location/Qualifiers
misc_feature            1..82
                        note = Synthetic
source                  1..82
                        mol_type = other RNA
                        organism = synthetic construct
SEQUENCE: 43
gttggaacca ttcaaaacag catagcaagt taaaataagg ctagtccgtt atcaacttga    60
aaaagtggca ccgagtcggt gc                                            82

SEQ ID NO: 44           moltype = RNA   length = 76
FEATURE                 Location/Qualifiers
misc_feature            1..76
                        note = Synthetic
source                  1..76
                        mol_type = other RNA
                        organism = synthetic construct
SEQUENCE: 44
gttttagagc tagaaatagc aagttaaaat aaggctagtc cgttatcaac ttgaaaaagt    60
ggcaccgagt cggtgc                                                   76

SEQ ID NO: 45           moltype = RNA   length = 86
FEATURE                 Location/Qualifiers
misc_feature            1..86
                        note = Synthetic
source                  1..86
                        mol_type = other RNA
                        organism = synthetic construct
SEQUENCE: 45
gtttaagagc tatgctggaa acagcatagc aagtttaaat aaggctagtc cgttatcaac    60
ttgaaaaagt ggcaccgagt cggtgc                                        86

SEQ ID NO: 46           moltype =    length =
SEQUENCE: 46
000

SEQ ID NO: 47           moltype =    length =
SEQUENCE: 47
000

SEQ ID NO: 48           moltype =    length =
SEQUENCE: 48
000

SEQ ID NO: 49           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 49
gagcaacctc actcttgtct                                               20

SEQ ID NO: 50           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 50
tgcatttgtt tcaaaatatt                                               20

SEQ ID NO: 51           moltype = RNA   length = 20
FEATURE                 Location/Qualifiers
misc_feature            1..20
                        note = Synthetic
source                  1..20
                        mol_type = other RNA
```

```
                                -continued
                      organism = synthetic construct
SEQUENCE: 51
atttatgaga tcaacagcac                                              20

SEQ ID NO: 52         moltype = RNA   length = 20
FEATURE               Location/Qualifiers
misc_feature          1..20
                      note = Synthetic
source                1..20
                      mol_type = other RNA
                      organism = synthetic construct
SEQUENCE: 52
ttaaataaag catagtgcaa                                              20

SEQ ID NO: 53         moltype = RNA   length = 20
FEATURE               Location/Qualifiers
misc_feature          1..20
                      note = Synthetic
source                1..20
                      mol_type = other RNA
                      organism = synthetic construct
SEQUENCE: 53
taaagcatag tgcaatggat                                              20

SEQ ID NO: 54         moltype = RNA   length = 20
FEATURE               Location/Qualifiers
misc_feature          1..20
                      note = Synthetic
source                1..20
                      mol_type = other RNA
                      organism = synthetic construct
SEQUENCE: 54
taataaaatt caaacatcct                                              20

SEQ ID NO: 55         moltype = RNA   length = 20
FEATURE               Location/Qualifiers
misc_feature          1..20
                      note = Synthetic
source                1..20
                      mol_type = other RNA
                      organism = synthetic construct
SEQUENCE: 55
tgactgaaac ttcacagaat                                              20

SEQ ID NO: 56         moltype = RNA   length = 20
FEATURE               Location/Qualifiers
misc_feature          1..20
                      note = Synthetic
source                1..20
                      mol_type = other RNA
                      organism = synthetic construct
SEQUENCE: 56
gactgaaact tcacagaata                                              20

SEQ ID NO: 57         moltype = RNA   length = 20
FEATURE               Location/Qualifiers
misc_feature          1..20
                      note = Synthetic
source                1..20
                      mol_type = other RNA
                      organism = synthetic construct
SEQUENCE: 57
agtgcaatgg ataggtcttt                                              20

SEQ ID NO: 58         moltype = RNA   length = 20
FEATURE               Location/Qualifiers
misc_feature          1..20
                      note = Synthetic
source                1..20
                      mol_type = other RNA
                      organism = synthetic construct
SEQUENCE: 58
cctcactctt gtctgggcaa                                              20

SEQ ID NO: 59         moltype = RNA   length = 20
FEATURE               Location/Qualifiers
misc_feature          1..20
                      note = Synthetic
source                1..20
```

```
                        mol_type = other RNA
                        organism = synthetic construct
SEQUENCE: 59
acctcactct tgtctgggca                                                 20

SEQ ID NO: 61           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 60
tgagcaacct cactcttgtc                                                 20

SEQ ID NO: 61           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 61
tactttgcac tttccttagt                                                 20

SEQ ID NO: 62           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 62
cactcttgtc tgtggaaaca                                                 20

SEQ ID NO: 63           moltype = DNA  length = 6150
FEATURE                 Location/Qualifiers
misc_feature            1..6150
                        note = Synthetic
source                  1..6150
                        mol_type = other DNA
                        organism = synthetic construct
SEQUENCE: 63
aacacccctt gtattactgt ttatgtaagc agacagtttt attgttcatg atgatatatt       60
tttatcttgt gcaatgtaac atcagagatt ttgagcacg ggccagagct gcatcgcgcg     120
tttcggtgat gacggtgaaa acctctgaca catgcagctc ccggagacgg tcacagcttg     180
tctgtaagcg gatgccggga gcagacaagc ccgtcaggc gcgtcagcgg gtgttggcgg     240
gtgtcgggc tggcttaact atgcggcatc agagcagatt gtactgagag tgcaccatat     300
gcggtgtgaa ataccgcaca gatgcgtaag gagaaaatac cgcatcaggc gccattcgcc     360
attcaggctg cgcaactgtt gggaagggcg atcggtgcgg gcctcttcgc tattacgcca     420
gctggcgaaa gggggatgtg ctgcaaggcg attaagttgg gtaacgccag ggttttccca     480
gtcacgacgt tgtaaaacga cggccagaga attcgagctc ggtacctcgc gaatacatct     540
agataggaac ccctagtgat ggagttggcc actccctctc tgcgcgctcg ctcgctcact     600
gaggccgccc gggcaaagcc cgggcgtcgg gcgacctttg gtcgcccggc ctcagtgagc     660
gagcgagcgc gcagagaggg agtggccaaa gatctcttag gtcagtgaag agaagaacaa     720
aaagcagcat attacagtta gttgtcttca tcaatcttta aatatgttgt gtggttttc     780
tctccctgtt tccacagttt ttcttgatca tgaaaacgcc aacaaaattc tgaatcggcc     840
aaagaggtat aattcaggta aattggaaga gtttgttcaa gggaaccttg agagagaatg     900
tatggaagaa aagtgtagtt ttgaagaagc acgagaagtt tttgaaaaca ctgaaagaac     960
aactgaattt tggaagcagt atgttgatgg agatcagtgt gagtccaatc catgtttaaa    1020
tggcggcagt tgcaaggatg acattaattc ctatgaatgt tggtgtccct ttggatttga    1080
aggaaagaac tgtgaattag atgtaacatg taacattaag aatggcagat gcgagcagtt    1140
ttgtaaaaat agtgctgata acaaggtggt ttgctcctgt actgagggat atcgacttgc    1200
agaaaaccag aagtcctgtg aaccagcagt gccatttcca tgtgaagag gttctgtttc    1260
acaaacttct aagctcaccc gtgctgagac tgtttttcct gatgtggact atgtaaattc    1320
tactgaagct gaaaccattt tggataacat cactcaaagc acccaatcat ttaatgactt    1380
cactcgggtt gttggtggag aagatgccaa accaggtcaa ttcccttggc aggttgtttt    1440
gaatggtaaa gttgatgcat tctgtggagg ctctatcgtt aatgaaaaat ggattgtaac    1500
tgctgcccac tgtgttgaaa ctggtgttaa aattacagtt gtcgcaggtg aacataatat    1560
tgaggagaca gaacatacag agcaaaagcg aaatgtgatt cgaattattc ctcaccacaa    1620
ctacaatgca gctattaata gtacaacca tgacattgcc cttctggaac tggacgaacc    1680
cttagtgcta aacagctacg ttacacctat ttgcattgct gacaaggaat acacgaacat    1740
cttcctcaaa tttggatctg gctatgtaag tggctgggga agtcttcc acaaagggag    1800
atcagcttta gttcttcagt accttagagt tccacttgtt gaccgagcca catgtcttct    1860
atctacaaag ttcaccatct ataacaacat gttctgtgct ggcttccatg aaggaggtag    1920
agattcatgt caaggagata gtgggggacc ccatgttact gaagtggaag gaccagttt    1980
cttaactgga attattagct ggggtgaaga gtgtgcaatg aaaggcaaat atggaatata    2040
taccaaggta tcccggtatg tcaactggat taaggaaaa acaaagctca cttaacctcg    2100
actgtgcctt ctagttgcca gccatctgtt gtttgcccct ccccgtgcc ttccttgacc    2160
```

```
ctggaaggtg ccactcccac tgtcctttcc taataaaatg aggaaattgc atcgcattgt   2220
ctgagtaggt gtcattctat tctgggggt ggggtggggc aggacagcaa ggggggaggat   2280
tgggaagaca atagcaggca tgctggggat gcggtgggct ctatggcttc tgaggcggaa   2340
agaaccagct ggggctctag ggggtatccc caaaaaacct cccacacctc cccctgaacc   2400
tgaaacataa aatgaatgca attgttgttg ttaacttgtt tattgcagct tataatggtt   2460
acaaataaag caatagcatc acaaatttca caaataaagc attttttca ctgcattcta    2520
gttgtggttt gtccaaactc atcaatgtat cttatcatgt ctgttaggtg agcttagtct    2580
tttcttttat ccaattcacg tagcgagaga ccttcgtata gatgccatat ttccccttca    2640
tcgcacattc ctcccccaa cttattatcc cggtcaagaa acttgttcct tcgacttcag     2700
tgacgtgtgg tccacctgaa tcaccttggc atgagtcgcg accgccctcg tgaaacccga    2760
cacaaaacat gttattgtaa atcgtaaatt tcgtggacag aagacaggtc gctctatcga    2820
ccaacgggac gcgcaaatat tgcagaacga gggctgatcg acctttgtgg aagacccgcc    2880
cccacccact cacatatccg ctcccaaatt tcaagaagat atttgtatat tcttttatcgg   2940
ctatacaaat cgggtaaca taggagttaa gtacgagtgg ctcgtccagc tccaggaggg    3000
ctatatcatg gttgtacttg tttatagcgg cattataatt gtgatgggt atgatcctga    3060
taacattcct tttctgttca gtatgctcag tttcttcaat gttgtgttcg ccagccacga    3120
ccgtaatctt aaccccgtc tcgacacagt gtgcggccgt tacaatccac tttcattga    3180
ctatgagcc cccacaaaac gcgtcgactt ttccgttgag caccacctgc catggaaatt   3240
ggccaggttt agcgtcctcg cccccgacaa ccctagtaaa gtcattaaat gactgtgtgg   3300
attgtgttat attatcaaga atcgtttcgg cttcagtaga gttaacgtag tccacatcgg   3360
gaaaaactgt ctcggccctt gtcaactttg atgtctggga cacacttacc cgaccgcacg   3420
ggaaggggcac cgccggttca cagctctttt gattctcagc gagccggtag ccctcagtgc  3480
aactacacac aactttgttg tcggcggaat ttttacagaa ttgctcgcat cgtccatttt   3540
taatgttgca ggtgacgtcc aactcgcagt tttttccttc aaaaccaaaa gggcaccaac   3600
actcgtagga atttatatcg tctttacaac tcccccatt cagacatgga ttagattcgc    3660
attggtcccc atcgacatat tgcttccaga actcagtggt ccgttctgta ttctcaaaca    3720
cctcgcgcgc ttcttcaaaa ctgcattttt cctccataca ctctcgctcc aagttcctt    3780
gcacgaattc ttcaagcttt cctgagttat acctttagg ccggttaagt atcttattcg     3840
cgttttcgtg gtccagaaaa actgtggaaa cagggagaga aaaaccacac aacatattta    3900
aagattgatg aagacaacta actgtaatat gctgcttttt gttcttctct tcactgacct     3960
aagagatcta ggaaccccta gtgatggagt tggccactcc ctctctgcgc gctcgctcgc    4020
tcactgaggc cgcccgggca aagcccgggc gtcgggcgac ctttggtcgc ccggcctcag   4080
tgagcgagcg agcgcgcaga gagggagtgg ccaaactcgg atcccgggcc cgtcgactgc    4140
agaggcctgc atgcaagcgt ggtgtaatca tggtcatagc tgtttcctgt gtgaaattgt     4200
tatccgctca caattccaca caacatacga gccggaagca taagtgtaaa agcctgggt    4260
gcctaatgag tgagctaact cacattaatt gcgttgcgct cactgcccgc tttccagtcg    4320
ggaaacctgt cgtgccagct gcattaatga atcggccaac gcgcggggag aggcggtttg    4380
cgtattgggc gctcttccgc ttcctcgctc actgactcgc tgcgctcggt cgttcggctg    4440
cggcgagccg tatcagctca ctcaaaggcg gtaatacgt tatccacaga atcagggga    4500
aacgcaggaa agaacatgtg agcaaaaggc cagcaaaagg ccaggaaccg taaaaaggcc    4560
gcgttgctgg cgttttttcca taggctccgc cccctgacg agcatcacaa aaatcgacgc   4620
tcaagtcaga ggtggcgaaa cccgacagga ctataaagat accaggcgtt ccccctgga    4680
agctccctcg tgcgctctcc tgttccgacc ctgccgctta ccggatacct gtccgccttt    4740
ctcccttcgg gaagcgtggc gctttctcat agctcacgct gtaggtatct cagttcggtg    4800
taggtcgttc gctccaagct gggctgtgtg cacgaacccc ccgttcagcc cgaccgctgc    4860
gccttatccg gtaactatcg tcttgagtcc aacccggtaa gacacgactt atcgccactg    4920
gcagcagcca ctggtaacag gattagcaga gcgaggtatg taggcggtgc tacagagttc    4980
ttgaagtggt ggcctaacta cggctacact agaagaacag tatttggtat ctgcgctctg    5040
ctgaagccag ttaccttcgg aaaaagagtt ggtagctctt gatccggcaa acaaaccacc    5100
gctggtagcg gtggttttttt tgtttgcaag cagcagatta cgcgcagaaa aaaggatct    5160
caagaagatc ctttgatctt ttctacgggg tctgacgctc agtggaacga aaactcacgt    5220
taagggattt tggtcatgag attatcaaaa aggatcttca cctagatcct ttttaaattaa   5280
aaatgaagtt ttaaatcaag cccaatctga ataatgttac aaccaattaa ccaattctga   5340
ttagaaaaac tcatcgagca tcaaatgaaa ctgcaattta ttcatatcag gattatcaat    5400
accatatttt tgaaaaagcc gtttctgtaa tgaaggagaa aactcaccga ggcagttcca   5460
taggatggca agatcctggt atcggtctgc gattccgact cgtccaacat caatacaacc    5520
tattaatttc ccctcgtcaa aaataaggtt atcaagtgag aaatcaccat gagtgacgac    5580
tgaatccggt gagaatggca aaagtttatg catttctttc cagacttgtt caacaggcca    5640
gccattacgc tcgtcatcaa aatcactcgc atcaaccaaa ccgttattca ttcgtgattg   5700
cgcctgagcg agacgaaata cgcgatcgct gttaaaagga caattacaaa caggaatcga   5760
atgcaaccgg cgcaggaaca ctgccagcgc atcaacaata ttttcacctg aatcaggata    5820
ttcttctaat acctggaatg ctgttttttcc gggatcgca gtggtgagta accatgcatc    5880
atcaggagta cggataaaat gcttgatggt cggaagaggc ataaattccg tcagccagtt    5940
tagtctgacc atctcatctg taacatcatt ggcaacgcta cctttgccat gtttcagaaa   6000
caactctggc gcatcgggct tcccatacaa gcgatagatt gtcgcacctg attgcccgac    6060
attatcgcga gcccatttat acccatataa atcagcatcc atgttggaat ttaatcgcgg    6120
cctcgacgtt tcccgttgaa tatggctcat                                      6150

SEQ ID NO: 64         moltype = DNA   length = 6901
FEATURE               Location/Qualifiers
misc_feature          1..6901
                      note = Synthetic
source                1..6901
                      mol_type = other DNA
                      organism = synthetic construct
SEQUENCE: 64
gaggcccttt cgtctcgcgc gtttcggtga tgacggtgaa aacctctgac acatgcagct    60
cccggagacg gtcacagctt gtctgtaagc ggatgccggg agcagacaag cccgtcaggg    120
cgcgtcagcg ggtgttggcg ggtgtcgggg ctggcttaac tatgcggcat cagagcagat    180
```

```
tgtactgaga gtgcaccata tgcggtgtga aataccgcac agatgcgtaa ggagaaaata   240
ccgcatcagg cgccattcgc cattcaggct gcgcaactgt tgggaagggc gatcggtgcg   300
ggcctcttcg ctattacgcc agctggcgaa aggggggatgt gctgcaaggc gattaagttg  360
ggtaacgcca gggttttccc agtcacgacg ttgtaaaacg acggccagtg aattcgagct   420
cggtacccct gcaggcagct gcgcgctcgc tcgctcactg acgcgccgg ggcaaagccc    480
gggcgtcggg cgacctttgg tcgcccggcc tcagtgagcg agcgagcgcg cagagaggga   540
gtggccaact ccatcactag ggggttcctcg ggcaaagcca cgcgtactag ttattaatag  600
taatcaatta cggggtcatt agttcatagc ccatatatgg agttccgcgt tacataactt   660
acggtaaatg gcccgcctgg ctgaccgccc aacgaccccc gcccattgac gtcaataatg   720
acgtatgttc ccatagtaac gccaataggg actttccatt gacgtcaatg ggtggagtat   780
ttacggtaaa ctgcccactt ggcagtacat caagtgtatc atatgccaag tacgccccct   840
attgacgtca atgacggtaa atggcccgcc tggcattatg cccagtacat gaccttatgg   900
gactttccta cttggcagta catctacgta ttagtcatcg ctattaccat ggtcgaggtg   960
agccccacgt tctgcttcac tctccccatc tcccccccc cccacccc aattttgtat     1020
ttatttattt tttaattatt ttgtgcagcg atggggggcgg gggggggggg ggggcgcgcg  1080
ccaggcgggg cggggcgggg cgaggggcgg ggcggggcga ggcggagagg tgcggcggca   1140
gccaatcaga gcggcgcgct ccgaaagttt ccttttatgg cgaggcggcg gcggcggcgg   1200
ccctataaaa agcgaagcgc gcggcgggcg gggagtcgct gcgacgctgc cttcgccccg   1260
tgccccgctc cgccgccgcc tcgcgccgcc cgccccggct ctgactgacc gcgttactcc   1320
cacaggtgag cgggcgggac ggcccttctc ctccgggctg taattagcgc ttggtttaat   1380
gacggcttgt ttcttttctg tggctgcgtg aaagccttga gggctccgg gagggccctt    1440
tgtgcggggg gagcggctcg gggggtgcgt gcgtgtgtgt gtgcgtgtgg agcgccgcgt   1500
gcggctccgc gctgcccggc ggctgtgagc gctgcgcggg cggcgcgggg ctttgtgcgc   1560
tccgcagtgt gcgcgagggg agcgcggccg ggggcggtgc cccgcggtgc gggggggggct 1620
gcgagggaa caaaggctgc gtgcggggtg tgtgcgtggg ggggtgagca ggggtgtgg    1680
gcgcgtcggt cgggctgcaa cccccctgc accccctcc ccgagttgct gagcacgcgc    1740
cggcttcggg tgcggggctc cgtacggggc gtgcgcggg gctcgccgtg ccgggcgggg   1800
ggtggcggca ggtgggggtg ccggggcggg cgggccgcc tcgggccggg gagggctcgg    1860
gggagggcgc cggcggcccc cggagcgccg gcggctgtcg aggcgcggcg agccgcagcc   1920
attgccttt atggtaatcg tgcgagaggg gcgcagggact tcctttgtcc caaatctgtg   1980
cggagccgaa atctgggagg cgccgccgca cccctctag cgggcgcggg gcgaagcggt    2040
gcggcgccgg caggaaggaa atgggcgggg agggccttcg tgcgtcgccg cgccgccgtc   2100
cccttctccc tctccagcct cggggctgtc cgcgggggga cggctgcctt cgggggggac   2160
ggggcagggc ggggttcggc ttctggcgtg tgaccgcgg ctctagagcc tctgctaacc    2220
atgttcatgc cttcttcttt ttcctacagc tcctggcaca cgtgctggtt attgtgctgt   2280
ctcatcattt tggcaaagaa ttcctcgaga tgcagcgcgt gaacatgatc atggcagaat   2340
caccaggcct catcaccatc tgccttttag gatatctact cagtgctgaa tgtacagttt   2400
ttcttgatca tgaaaacgcc aacaaaattc tgaatcggcc aaagaggtat aattcaggta   2460
aattggaaga gtttgttcaa gggaaccttg agagagaagta tatggaagaa aagtgtagtt  2520
ttgaagaagc acgagaagtt tttgaaaaca ctgaaagaac aactgaattt tggaagcagt   2580
atgttgatgg agatcagtgt gagtccaatc catgtttaaa tggcggcagt tgcaaggatg   2640
acattaattc ctatgaatgt tggtgtccct ttggatttga aggaaagaac tgtgaattag   2700
atgtaacatg taacattaag aatggcagat gcgagcagtt ttgtaaaaat agtgctgata   2760
acaaggtggt ttgctcctgt actgagggat atcgacttgc agaaaaccag aagtcctgtg   2820
aaccagcagt gccatttcca tgtggaagag tttctgtttc acaaacttct aagctcaccc   2880
gtgctgagac tgtttttcct gatgtggact atgtaaattc tactgaagct gaaaccattt   2940
tggataacat cactcaaagc acccaatcat ttaatgactt cactcgggtt gttggtggag   3000
aagatgccaa accaggtcaa ttcccttggc aggttgtttt gaatggtaaa gttgatgcat   3060
tctgtggagg ctctatcgtt aatgaaaaat ggattgtaac tgctgccac tgtgttgaaa    3120
ctggtgttaa aattacagtt gtcgcaggtg aacataatat tgaggagaca gaacatacag   3180
agcaaaagcg aaatgtgatt cgaattattc ctccaccaca ctacaatgca gctattaata   3240
agtacaacca tgacattgcc cttctgaac tggacgaacc cttagtgcta aacagctacg    3300
ttacacctat ttgcattgct gacaaggaat acacgaacat cttcctcaaa tttggatctg   3360
gctatgtaag tggctgggga agagtcttcc acaaagggag atcagcttta gttcttcagt   3420
accttagagt tccacttgtt gaccgagcca catgtcttcg atctacaaag ttcaccatct   3480
ataacaacat gttctgtgct ggcttccatg aaggaggtag agattcatgt caaggagata   3540
gtggggggacc ccatgttact gaagtggaag ggaccagttt cttaactgga attattagct   3600
ggggtgaaga gtgtgcaatg aaaggcaaat atggaatata taccaaggta tcccggtatg   3660
tcaactggat taaggaaaaa acaaagctca cgtttaaa ctcaacctct                3720
ggattacaaa atttgtgaaa gattgactgg tattcttaac tatgttctc cttttacgct    3780
atgtggatac gctgctttaa tgcctttgta tcatgctatt gcttcccgta tggctttcat   3840
tttctcctcc ttgtataaat cctgttgct gtctctttat gaggagttgt ggcccgttgt    3900
caggcaacgt ggcgtggtgt gcactgtgtt tgctgacgca accccactg gttggggcat   3960
tgccaccacc tgtcagctcc tttccggac tttcgcttc cttgccaccc tactgcccga    4020
ggaactcatc gccgcctgcc ttgcccgctg ctgacaggg gctcggctgt tgggcactga   4080
caattccgtg gtgttgtcgg ggaaatcatc gtcctttcct tggctgctcg cctgtgttgc   4140
cacctggatt ctgcgcggga cgtccttctg ctacgtccct tcggccctca atccagcgga   4200
ccttccttcc cgcggcctgc tgcggctct gcggcctctt ccgcgtcttc gccttcgccc   4260
tcagacgagt cggatctccc tttgggccgc ctccccgcag aattcctgca gctagttgcc  4320
agccatctgt tgtttgcccc tcccgtgc cttccttgac cctggaaggt gccactccca   4380
ctgtcctttc ctaataaaat gaggaaattg catcgcattg tctgagtagg tgtcattcta   4440
ttctgggggg tggggtgggg caggacagca agggggagga ttgggaagac aatagcaggc   4500
atgctgggga tgcggtgggc tctatgggt aaccaggaac cctagtgat ggagttggcc     4560
actccctctc tgcgcgctcg ctcgctcact gaggccggga gaccaaaggt cgcccgacgc   4620
ccgggctttg cccgggcggc ctcagtgagc gagcgagcgc gcagctgcct gcaggaagct   4680
tggcgtaatc atggtcatag ctgtttcctg tgtgaaattg ttatccgctc acaattccac   4740
acaacatacg agccggaagc ataaagtgta aagcctgggg tgcctaatga gtgagctaac   4800
tcacattaat tgcgttgcgc tcactgcccg ctttccagtc gggaaacctg tcgtgccagc   4860
tgcattaatg aatcggccaa cgcgcgggga gaggcggttt gcgtattggg cgctcttccg   4920
```

```
cttcctcgct cactgactcg ctgcgctcgg tcgttcggct gcggcgagcg gtatcagctc    4980
actcaaaggc ggtaatacgg ttatccacag aatcagggga taacgcagga aagaacatgt    5040
gagcaaaagg ccagcaaaag gccaggaacc gtaaaaaggc cgcgttgctg gcgttttcc     5100
ataggctccg cccccctgac gagcatcaca aaaatcgacg ctcaagtcag aggtggcgaa    5160
acccgacagg actataaaga taccaggcgt ttccccctgg aagctccctc gtgcgctctc    5220
ctgttccgac cctgccgctt accggatacc tgtccgcctt tctcccttcg ggaagcgtgg    5280
cgctttctca tagctcacgc tgtaggtatc tcagttcggt gtaggtcgtt cgctccaagc    5340
tgggctgtgt gcacgaaccc cccgttcagc ccgaccgctg cgccttatcc ggtaactatc    5400
gtcttgagtc caacccggta agacacgact tatcgccact ggcagcagcc actggtaaca    5460
ggattagcag agcgaggtat gtaggcggtg ctacagagtt cttgaagtgg tggcctaact    5520
acggctacac tagaaggaca gtatttggta tctgcgctct gctgaagcca gttaccttcg    5580
gaaaaagagt tggtagctct tgatccggca aacaaaccac cgctggtagc ggtggttttt    5640
ttgtttgcaa gcagcagatt acgcgcagaa aaaaggatc tcaagaagat cctttgatct     5700
tttctacggg gtctgacgct cagtggaacg aaaactcacg ttaagggatt ttggtcatga    5760
gattatcaaa aaggatcttc acctagatcc ttttaaatta aaaatgaagt tttaaatcaa    5820
tctaaagtat atatgagtaa acttggtctg acagttacca atgcttaatc agtgaggcac    5880
ctatctcagc gatctgtcta tttcgttcat ccatagttgc ctgactcccc gtcgtgtaga    5940
taactacgat acgggagggc ttaccatctg gccccagtgc tgcaatgata ccgcgagacc    6000
cacgctcacc ggctccagat ttatcagcaa taaaccagcc agccggaagg gccgagcgca    6060
gaagtggtcc tgcaacttta tccgcctcca tccagtctat taattgttgc cgggaagcta    6120
gagtaagtag ttcgccagtt aatagtttgc gcaacgttgt tgccattgct acaggcatcg    6180
tggtgtcacg ctcgtcgttt ggtatggctt cattcagctc cggttcccaa cgatcaaggc    6240
gagttacatg atcccccatg ttgtgcaaaa aagcggttag ctccttcggt cctccgatcg    6300
ttgtcagaag taagttggcc gcagtgttat cactcatggt tatggcagca ctgcataatt    6360
ctcttactgt catgccatcc gtaagatgct tttctgtgac tggtgagtac tcaaccaagt    6420
cattctgaga atagtgtatg cggcgaccga gttgctcttg cccggcgtca atacgggata    6480
ataccgcgcc acatagcaga actttaaaag tgctcatcat tggaaaacgt tcttcgggtgc   6540
gaaaactctc aaggatctta ccgctgttga gatccagttc gatgtaaccc actcgtgcac    6600
ccaactgatc ttcagcatct tttactttca ccagcgtttc tgggtgagca aaaacaggaa    6660
ggcaaaatgc cgcaaaaaag ggaataaggg cgacacggaa atgttgaata ctcatactct    6720
tcctttttca atattattga agcatttatc agggttattg tctcatgagc ggatacatat    6780
ttgaatgtat ttagaaaaat aaacaaatag gggttccgcg cacatttccc cgaaagtgc     6840
cacctgacgt ctaagaaacc attattatca tgacattaac ctataaaaat aggcgtatca    6900
c                                                                    6901
```

METHOD OF USING A GENETICALLY MODIFIED MOUSE THAT EXPRESSES HUMAN ALBUMIN

CROSS-REFERENCE TO RELATED APPLICATIONS

This application is a divisional of U.S. application Ser. No. 16/894,302, filed Jun. 5, 2020, which claims the benefit of U.S. Application No. 62/858,589, filed Jun. 7, 2019, and U.S. Application No. 62/916,666, filed Oct. 17, 2019, each of which is herein incorporated by reference in its entirety for all purposes.

REFERENCE TO A SEQUENCE LISTING SUBMITTED AS AN XML FILE VIA EFS WEB

The Sequence Listing written in file 057766-590633 SEQLIST.xml is 179 kilobytes, was created on Feb. 27, 2023, and is hereby incorporated by reference.

BACKGROUND

Gene therapy is a promising therapeutic approach for several human diseases. One approach to gene therapy is insertion of a transgene into a safe harbor locus in the genome. Safe harbor loci include chromosomal loci where transgenes or other exogenous nucleic acid inserts can be stably and reliably expressed in all tissues of interest without overtly altering cell behavior or phenotype. Often, a safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

One example of a safe harbor locus is albumin. However, there remains a need for suitable non-human animals providing the true or close approximation of the true human genomic DNA target of human-albumin-targeting reagents at the endogenous albumin locus in vivo, thereby enabling testing of the efficacy and mode of action of such agents in live animals as well as pharmacokinetic and pharmacodynamics studies in a setting where the humanized gene is the only version of albumin present.

SUMMARY

Non-human animals comprising a humanized albumin (ALB) locus are provided, as well as methods of making and using such non-human animals. Non-human animal genomes or cells comprising a humanized albumin (ALB) locus are also provided. Humanized albumin genes are also provided.

In one aspect, provided are non-human animal genomes, non-human animal cells, or non-human animals comprising a humanized albumin (ALB) locus. Such non-human animal genomes, non-human animal cells, or non-human animals can comprise in their genomes a humanized endogenous albumin locus in which a segment of the endogenous albumin locus has been deleted and replaced with a corresponding human albumin sequence.

In some such non-human animal genomes, non-human animal cells, or non-human animals the humanized endogenous albumin locus encodes a protein comprising a human serum albumin peptide. In some such non-human animal genomes, non-human animal cells, or non-human animals the humanized endogenous albumin locus encodes a protein comprising a human albumin propeptide. In some such non-human animal genomes, non-human animal cells, or non-human animals the humanized endogenous albumin locus encodes a protein comprising a human albumin signal peptide.

In some such non-human animal genomes, non-human animal cells, or non-human animals a region of the endogenous albumin locus comprising both coding sequence and non-coding sequence has been deleted and replaced with a corresponding human albumin sequence comprising both coding sequence and non-coding sequence. In some such non-human animal genomes, non-human animal cells, or non-human animals the humanized endogenous albumin locus comprises the endogenous albumin promoter, wherein the human albumin sequence is operably linked to the endogenous albumin promoter. In some such non-human animal genomes, non-human animal cells, or non-human animals at least one intron and at least one exon of the endogenous albumin locus have been deleted and replaced with the corresponding human albumin sequence.

In some such non-human animal genomes, non-human animal cells, or non-human animals the entire albumin coding sequence of the endogenous albumin locus has been deleted and replaced with the corresponding human albumin sequence. Optionally, the region of the endogenous albumin locus from the start codon to the stop codon has been deleted and replaced with the corresponding human albumin sequence.

In some such non-human animal genomes, non-human animal cells, or non-human animals the humanized endogenous albumin locus comprises a human albumin 3' untranslated region. In some such non-human animal genomes, non-human animal cells, or non-human animals the endogenous albumin 5' untranslated region has not been deleted and replaced with the corresponding human albumin sequence.

In some such non-human animal genomes, non-human animal cells, or non-human animals the region of the endogenous albumin locus from the start codon to the stop codon has been deleted and replaced with a human albumin sequence comprising the corresponding human albumin sequence and a human albumin 3' untranslated region, and the endogenous albumin 5' untranslated region has not been deleted and replaced with the corresponding human albumin sequence, and the endogenous albumin promoter has not been deleted and replaced with the corresponding human albumin sequence.

In some such non-human animal genomes, non-human animal cells, or non-human animals the human albumin sequence at the humanized endogenous albumin locus comprises a sequence at least 90%, 95%, 96%, 97%, 98%, 99%, or 100% identical to the sequence set forth in SEQ ID NO: 35. In some such non-human animal genomes, non-human animal cells, or non-human animals the humanized endogenous albumin locus encodes a protein comprising a sequence at least 90%, 95%, 96%, 97%, 98%, 99%, or 100% identical to the sequence set forth in SEQ ID NO: 5. In some such non-human animal genomes, non-human animal cells, or non-human animals the humanized endogenous albumin locus comprises a coding sequence comprising a sequence at least 90%, 95%, 96%, 97%, 98%, 99%, or 100% identical to the sequence set forth in SEQ ID NO: 13. In some such non-human animal genomes, non-human animal cells, or non-human animals the humanized endogenous albumin locus comprises a sequence at least 90%, 95%, 96%, 97%, 98%, 99%, or 100% identical to the sequence set forth in SEQ ID NO: 17 or 18. In some such non-human animal genomes, non-human animal cells, or non-human animals the human albumin sequence at the humanized endogenous albumin locus comprises a sequence at least about 90%, at least about 95%, at least about 96%, at least about 97%, at least about 98%, at least about 99%, or about 100% identical to the sequence set forth in SEQ ID NO: 35. In some such non-human animal genomes, non-human animal cells, or non-human animals the humanized endogenous albumin locus encodes a protein comprising a sequence at least about 90%, at least about 95%, at least about 96%, at least about 97%, at least about 98%, at least about 99%, or about 100% identical to the sequence set forth in SEQ ID NO: 5. In some such non-human animal genomes, non-human animal cells, or non-human animals the humanized endogenous albumin locus comprises a coding sequence comprising a sequence at least about 90%, at least about 95%, at least about 96%, at least about 97%, at least about 98%, at least about 99%, or about 100% identical to the sequence set forth in SEQ ID NO: 13. In some such non-human animal genomes, non-human animal cells, or non-human animals the humanized endogenous albumin locus comprises a sequence at least about 90%, at least about 95%, at least about 96%, at least about 97%, at least about 98%, at least about 99%, or about 100% identical to the sequence set forth in SEQ ID NO: 17 or 18.

In some such non-human animal genomes, non-human animal cells, or non-human animals the humanized endogenous albumin locus does not comprise a selection cassette or a reporter gene.

In some such non-human animal genomes, non-human animal cells, or non-human animals the non-human animal is homozygous for the humanized endogenous albumin locus. In some such non-human animal genomes, non-human animal cells, or non-human animals the non-human animal comprises the humanized endogenous albumin locus in its germline.

In some such non-human animal genomes, non-human animal cells, or non-human animals the non-human animal is a mammal. Optionally, the non-human animal is a rat or mouse. Optionally, the non-human animal is a mouse.

In some such non-human animal genomes, non-human animal cells, or non-human animals, the non-human animal comprises serum albumin levels of at least about 10 mg/mL. In some such non-human animal genomes, non-human animal cells, or non-human animals, serum albumin levels in the non-human animal are at least as high as serum albumin levels in a control non-human animal comprising a wild type albumin locus.

In some such non-human animal genomes, non-human animal cells, or non-human animals, the genome, cell, or animal is heterozygous for the humanized endogenous albumin locus. In some such non-human animal genomes, non-human animal cells, or non-human animals, the genome, cell, or animal is homozygous for the humanized endogenous albumin locus. In some such non-human animal genomes, non-human animal cells, or non-human animals, the genome, cell, or animal further comprises the coding sequence for an exogenous protein integrated into at least one allele of the humanized endogenous albumin locus in one or more cells of the non-human animal. Optionally, the coding sequence for the exogenous protein is integrated into intron 1 of the at least one allele of the humanized endogenous albumin locus (e.g., in the one or more cells of the non-human animal). In some such non-human animal genomes, non-human animal cells, or non-human animals, the genome, cell, or animal further comprises an inactivated endogenous locus that is not the endogenous albumin locus. Optionally, the non-human animal genome, non-human animal cell, or non-human animal further comprises the coding sequence for an exogenous protein integrated into at least one allele of the humanized endogenous albumin locus (e.g., in one or more cells of the non-human animal), wherein the exogenous protein replaces the function of the inactivated endogenous locus. Optionally, the inactivated endogenous locus is an inactivated F9 locus.

In another aspect, providing are targeting vectors for generating the non-human animal genomes, non-human animal cells, or non-human animals described above. Such targeting vectors can be for generating a humanized endogenous albumin locus in which a segment of the endogenous albumin locus has been deleted and replaced with a corresponding human albumin sequence, wherein the targeting vector comprises an insert nucleic acid comprising the corresponding human albumin sequence flanked by a 5' homology arm targeting a 5' target sequence at the endogenous albumin locus and a 3' homology arm targeting a 3' target sequence at the endogenous albumin locus.

In another aspect, provided are methods of assessing the activity of a human-albumin-targeting reagent in vivo. Some such methods comprise: (a) administering the human-albumin-targeting reagent to a non-human animal described above; and (b) assessing the activity of the human-albumin-targeting reagent in the non-human animal.

In some such methods, the administering comprises adeno-associated virus (AAV)-mediated delivery, lipid nanoparticle (LNP)-mediated delivery, or hydrodynamic delivery (HDD). Optionally, the administering comprises LNP-mediated delivery. Optionally, the LNP dose is between about 0.1 mg/kg and about 2 mg/kg. In some such methods, the administering comprises AAV8-mediated delivery.

In some such methods, step (b) comprises isolating a liver from the non-human animal and assessing activity of the human-albumin-targeting reagent in the liver.

In some such methods, the human-albumin-targeting reagent is a genome-editing agent, and the assessing comprises assessing modification of the humanized endogenous albumin locus. Optionally, the assessing comprises measuring the frequency of insertions or deletions within the humanized endogenous albumin locus.

In some such methods, the assessing comprises measuring expression of an albumin messenger RNA encoded by the humanized endogenous albumin locus. In some such methods, the assessing comprises measuring expression of an albumin protein encoded by the humanized endogenous albumin locus. Optionally, assessing expression of the albumin protein comprises measuring serum levels of the albumin protein in the non-human animal. Optionally, assessing expression of the albumin protein comprises measuring expression of the albumin protein in the liver of the non-human animal.

In some such methods, the human-albumin-targeting reagent comprises a nuclease agent designed to target a region of a human albumin gene. In some such methods, the human-albumin-targeting reagent comprises a nuclease agent or a nucleic acid encoding the nuclease agent, wherein the nuclease agent is designed to target a region of a human albumin gene. Optionally, the nuclease agent comprises a Cas protein and a guide RNA designed to target a guide RNA target sequence in the human albumin gene. Optionally, the guide RNA target sequence is in intron 1 of the human albumin gene. Optionally, the Cas protein is a Cas9 protein.

In some such methods, the human-albumin-targeting reagent comprises an exogenous donor nucleic acid, wherein the exogenous donor nucleic acid is designed to target the human albumin gene, and optionally wherein the exogenous donor nucleic acid is delivered via AAV. Optionally, the exogenous donor nucleic acid is a single-stranded oligodeoxynucleotide (ssODN). Optionally, the exogenous donor nucleic acid is capable of insertion into a humanized albumin locus by non-homologous end joining.

In some methods, the exogenous donor nucleic acid does not comprise homology arms. In some methods, the exogenous donor nucleic acid comprises an insert nucleic acid flanked by a 5' homology arm targeting a 5' target sequence at the humanized endogenous albumin locus and a 3' homology arm targeting a 3' target sequence at the humanized endogenous albumin locus. Optionally, each of the 5' target sequence and the 3' target sequence comprises a segment of intron 1 of the human albumin gene.

In some such methods, the exogenous donor nucleic acid encodes an exogenous protein. Optionally, the protein encoded by a humanized endogenous albumin locus that has been targeted with the exogenous donor nucleic acid is a heterologous protein comprising a human albumin signal peptide fused to the exogenous protein. Optionally, the exogenous protein is a factor IX protein. Optionally, the assessing comprises measuring serum levels of the factor IX protein in the non-human animal and/or comprises assessing activated partial thromboplastin time or performing a thrombin generation assay. Optionally, the non-human animal further comprises an inactivated F9 locus, and the assessing comprises measuring serum levels of the factor IX protein in the non-human animal and/or comprises assessing activated partial thromboplastin time or performing a thrombin generation assay. Optionally, the human-albumin-targeting reagent comprises (1) a nuclease agent designed to target a region of a human albumin gene and (2) an exogenous donor nucleic acid, the exogenous donor nucleic acid is designed to target the human albumin gene, the exogenous donor nucleic acid encodes an exogenous protein, and the protein encoded by a humanized endogenous albumin locus that has been targeted with the exogenous donor nucleic acid is a heterologous protein comprising a human albumin signal peptide fused to the exogenous protein. Optionally, the assessing comprises measuring expression of a messenger RNA encoded by the exogenous donor nucleic acid. Optionally, the assessing comprises measuring expression of the exogenous protein. Optionally, assessing expression of the heterologous protein comprises measuring serum levels of the heterologous protein in the non-human animal. Optionally, assessing expression of the heterologous protein comprises measuring expression in the liver of the non-human animal.

In another aspect, provided are methods of optimizing the activity of a human-albumin-targeting reagent in vivo. Some such methods comprise: (I) performing any of the above methods of assessing the activity of a human-albumin-targeting reagent in vivo a first time in a first non-human animal comprising in its genome a humanized endogenous albumin locus; (II) changing a variable and performing the method of step (I) a second time with the changed variable in a second non-human animal comprising in its genome a humanized endogenous albumin locus; and (III) comparing the activity of the human-albumin-targeting reagent in step (I) with the activity of the human-albumin-targeting reagent in step (II), and selecting the method resulting in the higher activity.

In some such methods, the changed variable in step (II) is the delivery method of introducing the human-albumin-targeting reagent into the non-human animal. Optionally, the administering comprises LNP-mediated delivery, and the changed variable in step (II) is the LNP formulation. In some such methods, the changed variable in step (II) is the route of administration of introducing the human-albumin-targeting reagent into the non-human animal. In some such methods, the changed variable in step (II) is the concentration or amount of the human-albumin-targeting reagent introduced into the non-human animal. In some such methods, the changed variable in step (II) is the form of the human-albumin-targeting reagent introduced into the non-human animal. In some such methods, the changed variable in step (II) is the human-albumin-targeting reagent introduced into the non-human animal.

In some such methods, the human-albumin-targeting reagent comprises a Cas protein and a guide RNA designed to target a guide RNA target sequence in a human albumin gene. In some such methods, the human-albumin-targeting reagent comprises a Cas protein or a nucleic acid encoding the Cas protein and a guide RNA or a DNA encoding the guide RNA, wherein the guide RNA is designed to target a guide RNA target sequence in a human albumin gene. Optionally, the changed variable in step (II) is the guide RNA sequence or the guide RNA target sequence. Optionally, the Cas protein and the guide RNA are each administered in the form of RNA, and the changed variable in step (II) is the ratio of Cas mRNA to guide RNA. Optionally, the changed variable in step (II) is guide RNA modifications. Optionally, the human-albumin-targeting reagent comprises a messenger RNA (mRNA) encoding the Cas protein and the guide RNA, and the changed variable in step (II) is the ratio of Cas mRNA to guide RNA.

In some such methods, the human-albumin-targeting reagent comprises an exogenous donor nucleic acid. Optionally, the changed variable in step (II) is the form of the exogenous donor nucleic acid. Optionally, the exogenous donor nucleic acid comprises an insert nucleic acid flanked by a 5' homology arm targeting a 5' target sequence at the humanized endogenous albumin locus and a 3' homology arm targeting a 3' target sequence at the humanized endogenous albumin locus, and the changed variable in step (II) is the sequence or length of the 5' homology arm and/or the sequence or length of the 3' homology arm.

In another aspect, provided are methods of making any of the above non-human animals. Some such methods comprise: (a) introducing into a non-human animal embryonic stem (ES) cell: (i) a nuclease agent that targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human ES cell comprising in its genome the humanized endogenous albumin locus comprising the human albumin sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous albumin locus comprising the human albumin sequence. In another aspect, provided are methods of making any of the above non-human animals. Some such methods comprise: (a) introducing into a non-human animal embryonic stem (ES) cell: (i) a nuclease agent or a nucleic acid encoding the nuclease agent, wherein the nuclease agent targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human ES cell comprising in its genome the humanized endogenous albumin locus comprising the human albumin sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous albumin locus comprising the human albumin sequence. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo: (i) a nuclease agent that targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human one-cell stage embryo comprising in its genome the humanized endogenous albumin locus comprising the human albumin sequence; (b) gestating the genetically modified non-human animal one-cell stage embryo in a surrogate mother to produce a genetically modified F0 generation non-human animal comprising in its genome the humanized endogenous albumin locus comprising the human albumin sequence. Some such methods comprise: (a) introducing into a non-human animal one-cell stage embryo: (i) a nuclease agent or a nucleic acid encoding the nuclease agent, wherein the nuclease agent targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human one-cell stage embryo comprising in its genome the humanized endogenous albumin locus comprising the human albumin sequence; (b) gestating the genetically modified non-human animal one-cell stage embryo in a surrogate mother to produce a genetically modified F0 generation non-human animal comprising in its genome the humanized endogenous albumin locus comprising the human albumin sequence.

In some such methods, the nuclease agent comprises a Cas protein and a guide RNA. Optionally, the Cas protein is a Cas9 protein. Optionally, step (a) further comprises introducing a second guide RNA that targets a second target sequence within the endogenous albumin locus.

In some such methods, the non-human animal is a mouse or a rat. Optionally, the non-human animal is a mouse.

In another aspect, provided are methods of making any of the above non-human animals. Some such methods comprise: (a) modifying the genome of a pluripotent non-human animal cell to comprise the humanized endogenous albumin locus; (b) identifying or selecting the genetically modified pluripotent non-human animal cell comprising the humanized endogenous albumin locus; (c) introducing the genetically modified pluripotent non-human animal cell into a non-human animal host embryo; and (d) gestating the non-human animal host embryo in a surrogate mother. Some such methods comprise: (a) modifying the genome of a non-human animal one-cell stage embryo to comprise the humanized endogenous albumin locus; (b) selecting the genetically modified non-human animal one-cell stage embryo comprising the humanized endogenous albumin locus; and (c) gestating the genetically modified non-human animal one-cell stage embryo in a surrogate mother.

BRIEF DESCRIPTION OF THE FIGURES

FIG. 1A (not to scale) shows a schematic of the humanized mouse albumin (Alb) locus with the neomycin selection cassette (MAID 7626). The sequences for junctions A, B, and C are set forth in SEQ ID NOS: 19-21, respectively.

FIG. 1B (not to scale) shows a schematic of the humanized mouse albumin (Alb) locus following removal of the neomycin selection cassette (MAID 7627). The sequences for junctions A and D are set forth in SEQ ID NOS: 19 and 22, respectively.

FIGS. 3A and 3B show an alignment of the mouse (mouse Alb), human (human ALB), and humanized (7626 HumIn Prot) albumin proteins. Boxed residues constitute the signal peptide. Dotted lines denote the serum albumin peptide sequence. Heavy solid line denotes the propeptide sequence. All residues in the humanized albumin protein are encoded by introduced human exons.

FIG. 10A shows a TGA-EA profile of human normal and Factor-IXdeficient plasma samples. FIG. 10B shows a TGA-EA profile of mouse plasma from AAV-hF9 insertion in ALB$^{m/hu}$×F9$^{-/-}$ mice.

DEFINITIONS

Figure 2:
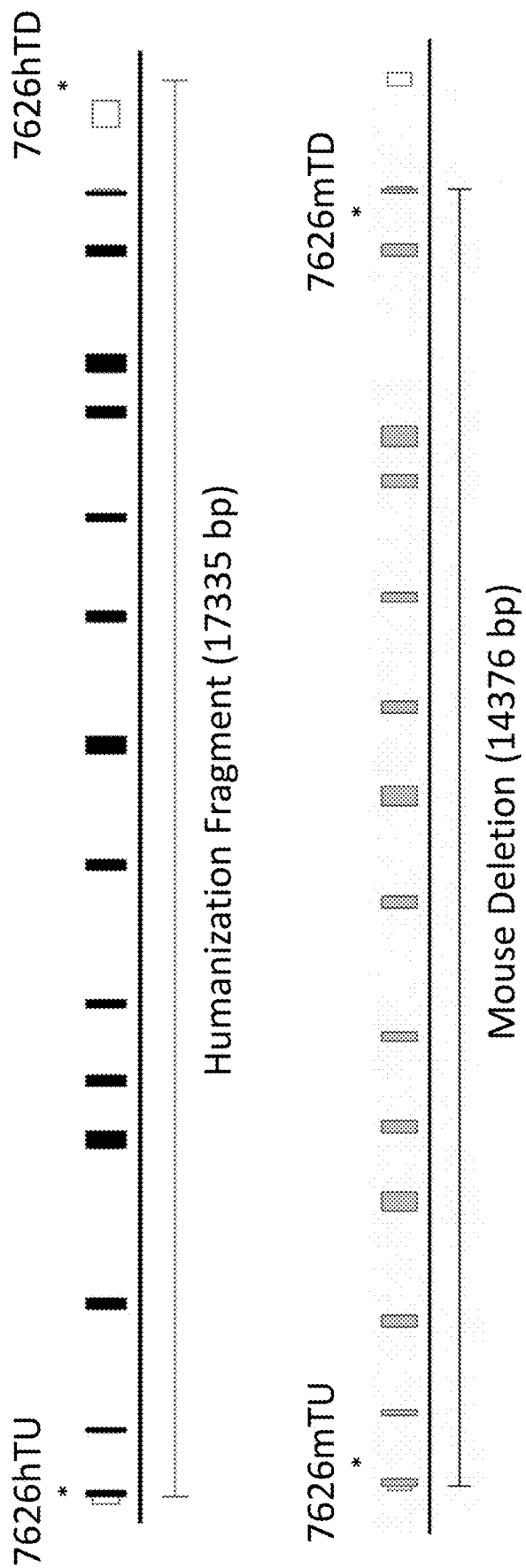
FIG. 2 (not to scale) shows the location of the TAQMAN® probes for screening humanization of the mouse albumin (Alb) locus. Gain-of-allele (GOA) probes include 7626hU and 7626hD. Loss-of-allele (LOA) probes include 7626mTU and 7626mTD.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues (e.g., liver samples), proteins, and nucleic acids includes cells, tissues (e.g., liver samples), proteins, and nucleic acids that are relatively purified with respect to other bacterial, viral, cellular, or other components that may normally be present in situ, up to and including a substantially pure preparation of the cells, tissues (e.g., liver samples), proteins, and nucleic acids. The term "isolated" also includes cells, tissues (e.g., liver samples), proteins, and nucleic acids that have no naturally occurring counterpart, have been chemically synthesized and are thus substantially uncontaminated by other cells, tissues (e.g., liver samples), proteins, and nucleic acids, or has been separated or purified from most other components (e.g., cellular components) with which they are naturally accompanied (e.g., other cellular proteins, polynucleotides, or cellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous albumin sequence of a non-human animal refers to a native albumin sequence that naturally occurs at the albumin locus in the non-human animal.

"Exogenous" molecules or sequences include molecules or sequences that are not normally present in a cell in that form or location (e.g., genomic locus). Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form and location in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "albumin locus" or "Alb locus" may refer to the specific location of an albumin (Alb) gene, albumin DNA sequence, albumin-encoding sequence, or albumin position on a chromosome of the genome of an organism that has been identified as to where such a sequence resides. An "albumin locus" may comprise a regulatory element of an albumin gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.*

31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

Disclosed herein are non-human animal genomes, non-human animal cells, and non-human animals comprising a humanized albumin (ALB) locus and methods of using such non-human animal cells and non-human animals. Non-human animal cells or non-human animals comprising a humanized albumin locus express a human albumin protein or a chimeric albumin protein comprising one or more fragments of a human albumin protein. Such non-human animal cells and non-human animals can be used to assess delivery or efficacy of human-albumin-targeting agents (e.g., CRISPR/Cas9 genome editing agents) in vitro, ex vivo, or in vivo and can be used in methods of optimizing the delivery of efficacy of such agents in vitro, ex vivo, or in vivo.

In some of the non-human animal cells and non-human animals disclosed herein, most or all of the human albumin genomic DNA is inserted into the corresponding orthologous non-human animal albumin locus. In some of the non-human animal cells and non-human animals disclosed herein, most or all of the non-human animal albumin genomic DNA is replaced one-for-one with corresponding orthologous human albumin genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. In contrast, insertion of human albumin cDNA into a non-human animal albumin locus would abolish conserved regulatory elements such as those contained within the first exon and intron of the non-human animal albumin. Replacing the non-human animal genomic sequence with the corresponding orthologous human genomic sequence or inserting human albumin genomic sequence in the corresponding orthologous non-human albumin locus is more likely to result in faithful expression of the transgene from the endogenous albumin locus. Similarly, transgenic non-human animals with transgenic insertion of human-albumin-coding sequences at a random genomic locus rather than the endogenous non-human-animal albumin locus will not as accurately reflect the endogenous regulation of albumin expression. A humanized albumin allele resulting from replacing most or all of the non-human animal genomic DNA one-for-one with corresponding orthologous human genomic DNA or inserting human albumin genomic sequence in the corresponding orthologous non-human albumin locus will provide the true human target or a close approximation of the true human target of human-albumin-targeting reagents (e.g., CRISPR/Cas9 reagents designed to target human albumin), thereby enabling testing of the efficacy and mode of action of such agents in live animals as well as pharmacokinetic and pharmacodynamics studies in a setting where the humanized protein and humanized gene are the only version of albumin present.

II. Non-Human Animals Comprising a Humanized Albumin (ALB) Locus

The non-human animal genomes, non-human animal cells, and non-human animals disclosed herein comprise a humanized albumin (ALB) locus. Cells or non-human animals comprising a humanized albumin locus express a human albumin protein or a partially humanized, chimeric albumin protein in which one or more fragments of the native albumin protein have been replaced with corresponding fragments from human albumin. Also disclosed herein are humanized non-human animal albumin genes in which a segment of the non-human albumin gene has been deleted and replaced with a corresponding human albumin sequence.

The non-human animal genomes, non-human animal cells, and non-human animals disclosed herein can further comprise an inactivated (knocked out) endogenous gene that is not the albumin locus. Such non-human animal genomes, non-human animal cells, and non-human animals can be used, for example, to screen gene therapy reagents (e.g., transgenes) for insertion into the humanized albumin locus to replace the inactivated endogenous gene. The insertion into the humanized albumin locus to replace the inactivated endogenous gene can, for example, rescue the knockout. In one specific example, the non-human animal genomes, non-human animal cells, and non-human animals disclosed herein can further comprise an inactivated (knocked out) endogenous F9 gene (encodes coagulating factor IX). An inactivated (knocked out) endogenous F9 gene is one that does not express any coagulation factor IX (also known as Christmas factor, plasma thromboplastin component, or PTC). The wild type human coagulation factor IX protein has been assigned UniProt accession number P00740, and the human F9 gene has been assigned GeneID 2158. The wild type mouse coagulation factor IX protein has been assigned UniProt accession number P16294, and the mouse F9 gene has been assigned GeneID 14071. The wild type rat coagulation factor IX protein has been assigned UniProt accession number P16296, and the rat F9 gene has been assigned GeneID 24946.

The non-human animal genomes, non-human animal cells, and non-human animals disclosed herein can further comprise the coding sequence for an exogenous protein integrated into at least one allele of the humanized albumin locus (e.g., in one or more cells of the non-human animal such as in one or more liver cells in the non-human animal). The coding sequence can be integrated, for example, in intron 1, intron 12, or intron 13 of the humanized albumin locus. In some cases, expression of human albumin from the humanized albumin locus is maintained at the same level following integration of the coding sequence for the exogenous protein into at least one allele of the humanized albumin locus (e.g., in one or more cells of the non-human animal such as in one or more liver cells in the non-human animal). In one example, the non-human animal genome, cell, or animal further comprises an inactivated (knocked out) endogenous gene that is not the albumin locus, and the exogenous protein replaces the function of the inactivated endogenous gene (e.g., rescues the knockout). In one specific example, the exogenous protein is coagulation factor IX (e.g., human coagulation factor IX).

A. Albumin

The cells and non-human animals described herein comprise a humanized albumin (ALB) locus. Albumin is encoded by the ALB gene (also known as albumin, serum albumin, PRO0883, PRO0903, HSA, GIG20, GIG42, PRO1708, PRO2044, PRO2619, PRO2675, and UNQ696/PRO1341). Albumin is synthesized in the liver as preproalbumin, which has an N-terminal peptide that is removed before the nascent protein is released from the rough endoplasmic reticulum. The product, proalbumin, is in turn cleaved in the Golgi vesicles to produce the secreted albumin (serum albumin). Human serum albumin is the serum albumin found in human blood. It is the most abundant protein in human blood plasma; it constitutes about half of serum protein. It is produced in the liver. It is soluble in water and monomeric. Albumin transports hormones, fatty acids, and other compounds, buffers pH, and maintains oncotic pressure, among other functions. Human albumin concentrations in serum are typically approximately 35-50 g/L (3.5-5.0 g/dL). It has a serum half-life of approximately 20 days. It has a molecular mass of 66.5 kDa.

Albumin is considered to be a genomic safe harbor locus because of its very high expression level and the tractability of liver for gene delivery and in vivo editing relative to other tissues. Safe harbor loci include chromosomal loci where transgenes or other exogenous nucleic acid inserts can be stably and reliably expressed in all tissues of interest without overtly altering cell behavior or phenotype. Often, a safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

The albumin gene structure is suited for transgene targeting into intronic sequences because its first exon encodes a secretory peptide (signal peptide) that is cleaved from the final protein product. For example, integration of a promoterless cassette bearing a splice acceptor and a therapeutic transgene would support expression and secretion of many different proteins.

Human ALB maps to human 4q13.3 on chromosome 4 (NCBI RefSeq Gene ID 213; Assembly GRCh38.p12 (GCF_000001405.38); location NC_000004.12 (73404239 . . . 73421484 (+))). The gene has been reported to have 15 exons. Of these, 14 of the exons are coding exon, and exon 15 is a non-coding exon that is part of the 3' untranslated region (UTR). The wild type human albumin protein has been assigned UniProt accession number P02768. At least three isoforms are known (P02768-1 through P02768-3). The sequence for one isoform, P02768-1 (identical to NCBI Accession No. NP_000468.1), is set forth in SEQ ID NO: 5. An mRNA (cDNA) encoding the canonical isoform is assigned NCBI Accession No. NM_000477.7 and is set forth in SEQ ID NO: 37. An exemplary coding sequence (CDS) is assigned CCDS ID CCDS3555.1 and is set forth in SEQ ID NO: 13. The full-length human albumin protein set forth in SEQ ID NO: 5 has 609 amino acids, including a signal peptide (amino acids 1-18), a propeptide (amino acids 19-24), and serum albumin (amino acids 25-609). Delineations between these domains are as designated in UniProt. Reference to human albumin includes the canonical (wild type) forms as well as all allelic forms and isoforms. Any other forms of human albumin have amino acids numbered for maximal alignment with the wild type form, aligned amino acids being designated the same number.

Mouse Alb maps to mouse 5 E1; 5 44.7 cM on chromosome 5 (NCBI RefSeq Gene ID 11657; Assembly GRCm38.p4 (GCF_000001635.24); location NC_000071.6 (90,460,870 . . . 90,476,602 (+))). The gene has been reported to have 15 exons. Of these, 14 of the exons are coding exon, and exon 15 is a non-coding exon that is part of the 3' untranslated region (UTR). The wild type mouse albumin protein has been assigned UniProt accession number P07724. The sequence for mouse albumin (identical to NCBI Accession No. NP_033784.2), is set forth in SEQ ID NO: 1. An exemplary mRNA (cDNA) isoform encoding the canonical isoform is assigned NCBI Accession No. NM_009654.4 and is set forth in SEQ ID NO: 36. An exemplary coding sequence (CDS) (CCDS ID CCDS19412.1) is set forth in SEQ ID NO: 9. The canonical full-length mouse albumin protein set forth in SEQ ID NO: 1 has 608 amino acids, including a signal peptide (amino acids 1-18), a propeptide (amino acids 19-24) and serum albumin (amino acids 25-608). Delineations between these domains are as designated in UniProt. Reference to mouse albumin includes the canonical (wild type) forms as well as all allelic forms and isoforms. Any other forms of mouse albumin have amino acids numbered for maximal alignment with the wild type form, aligned amino acids being designated the same number.

Albumin sequences for many other non-human animals are also known. These include, for example, bovine (UniProt accession number P02769; NCBI RefSeq Gene ID 280717), rat (UniProt accession number P02770; NCBI RefSeq Gene ID 24186), chicken (UniProt accession number P19121), Sumatran orangutan (UniProt accession number Q5NVH5; NCBI RefSeq Gene ID 100174145), horse (UniProt accession number P35747; NCBI RefSeq Gene ID 100034206), cat (UniProt accession number P49064; NCBI RefSeq Gene ID 448843), rabbit (UniProt accession number P49065; NCBI RefSeq Gene ID 100009195), dog (UniProt accession number P49822; NCBI RefSeq Gene ID 403550), pig (UniProt accession number P08835; NCBI RefSeq Gene ID 396960), Mongolian gerbil (UniProt accession number 035090), rhesus macaque (UniProt accession number Q28522; NCBI RefSeq Gene ID 704892), donkey (UniProt accession number Q5XLE4; NCBI RefSeq Gene ID 106835108), sheep (UniProt accession number P14639; NCBI RefSeq Gene ID 443393), American bullfrog (UniProt accession number P21847), golden hamster (UniProt accession number A6YF56; NCBI RefSeq Gene ID 101837229), and goat (UniProt accession number P85295).

B. Humanized Albumin Loci

A humanized albumin locus is an albumin locus in which a segment of the endogenous albumin locus has been deleted and replaced with an orthologous human albumin sequence. A humanized albumin locus can be an albumin locus in which the entire albumin gene is replaced with the corresponding orthologous human albumin sequence, or it can be an albumin locus in which only a portion of the albumin gene is replaced with the corresponding orthologous human albumin sequence (i.e., humanized). For example, the entire albumin coding sequence at the endogenous albumin locus can be deleted and replaced with the corresponding human albumin sequence. A human albumin sequence corresponding to a particular segment of endogenous albumin sequence refers to the region of human albumin that aligns with the particular segment of endogenous albumin sequence when human albumin and the endogenous albumin are optimally aligned. Optimally aligned refers to the greatest number of perfectly matched residues. The corresponding orthologous human sequence can comprise, for example, complementary DNA (cDNA) or genomic DNA. Optionally, the corresponding orthologous human albumin sequence is modified to be codon-optimized based on codon usage in the non-human animal. Replaced or inserted (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, 9, 10, 11, 12, 13, 14, or all 15 exons of the human albumin gene can be humanized. For example, exons corresponding to all exons (i.e., exons 1-15) of the human albumin gene can be humanized. As another example, exons corresponding to 1, 2, 3, 4, 5, 6, 7, 8, 9, 10, 11, 12, 13, or all 14 coding exons of the human albumin gene can be humanized. For example, exons corresponding to all coding exons (i.e., exons 1-14) of the human albumin gene can be humanized. Likewise, introns corresponding to 1, 2, 3, 4, 5, 6, 7, 8, 9, 10, 11, 12, 13, or all 14 introns of the human albumin gene can be humanized or can remain endogenous. For example, introns corresponding to all of the introns (i.e., introns 1-14) of the human albumin gene can be humanized. Likewise, introns corresponding to 1, 2, 3, 4, 5, 6, 7, 8, 9, 10, 11, 12, or all 13 of the introns between coding exons of the human albumin gene can be humanized or can remain endogenous. For example, introns corresponding to all of the introns between coding exons (i.e., introns 1-13) of the human albumin gene can be humanized. Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. One or both of the human 5' and 3' UTRs can be inserted, and/or one or both of the endogenous 5' and 3' UTRs can be deleted. In a specific example, both the 5' UTR and the 3' UTR remain endogenous. In another specific example, the 5' UTR remains endogenous and the 3' UTR is humanized. Depending on the extent of replacement by orthologous sequences, regulatory sequences, such as a promoter, can be endogenous or supplied by the replacing human orthologous sequence. For example, the humanized albumin locus can include the endogenous non-human animal albumin promoter (i.e., the human albumin sequence can be operably linked to the endogenous non-human animal promoter).

One or more or all of the regions encoding the signal peptide, the propeptide, or the serum albumin can be humanized, or one or more of such regions can remain endogenous. Exemplary coding sequences for a mouse albumin signal peptide, propeptide, and serum albumin are set forth in SEQ ID NOS: 10-12, respectively. Exemplary coding sequences for a human albumin signal peptide, propeptide, and serum albumin are set forth in SEQ ID NOS: 14-16, respectively.

For example, all or part of the region of the albumin locus encoding the signal peptide can be humanized, and/or all or part of the region of the albumin locus encoding the propeptide can be humanized, and/or all or part of the region of the albumin locus encoding the serum albumin can be humanized. Alternatively or additionally, all or part of the region of the albumin locus encoding the signal peptide can remain endogenous, and/or all or part of the region of the albumin locus encoding the propeptide can remain endogenous, and/or all or part of the region of the albumin locus encoding the serum albumin can remain endogenous. In one example, all or part of the regions of the albumin locus encoding the signal peptide, propeptide, and serum albumin are humanized. Optionally, the CDS of the humanized region of the albumin locus comprises, consists essentially of, or consists of a sequence that is at least 85%, 90%, 95%, 96%, 97%, 98%, 99%, or 100% identical to SEQ ID NO: 13 (or degenerates thereof). Optionally, the CDS of the humanized region of the albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 13 (or degenerates thereof). Optionally, the humanized region of the albumin locus comprises, consists essentially of, or consists of a sequence that is at least 85%, 90%, 95%, 96%, 97%, 98%, 99%, or 100% identical to SEQ ID NO: 35. Optionally, the humanized region of the albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 35. Optionally, the humanized albumin locus encodes a protein that comprises, consists essentially of, or consists of a sequence that is at least 85%, 90%, 95%, 96%, 97%, 98%, 99%, or 100% identical to SEQ ID NO: 5. Optionally, the humanized albumin locus encodes a protein that comprises, consists essentially of, or consists of a sequence that is at least about 85%, at least about 90%, at least about 95%, at least about 96%, at least about 97%, at least about 98%, at least about 99%, or about 100% identical to SEQ ID NO: 5. Optionally, the humanized albumin locus comprises, consists essentially of, or consists of a sequence that is at least 85%, 90%, 95%, 96%, 97%, 98%, 99%, or 100% identical to SEQ ID NO: 17 or 18. Optionally, the humanized albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 17 or 18.

The albumin protein encoded by the humanized albumin locus can comprise one or more domains that are from a human albumin protein and/or one or more domains that are from an endogenous (i.e., native) albumin protein. Exemplary amino acid sequences for a mouse albumin signal peptide, propeptide, and serum albumin are set forth in SEQ ID NOS: 2-4, respectively. Exemplary amino acid sequences for a human albumin signal peptide, propeptide, and serum albumin are set forth in SEQ ID NOS: 6-8, respectively.

The albumin protein can comprise one or more or all of a human albumin signal peptide, a human albumin propeptide, and a human serum albumin. Alternatively or additionally, the albumin protein can comprise one or more domains that are from the endogenous (i.e., native) non-human animal albumin protein. For example, the albumin protein can comprise a signal peptide from the endogenous (i.e., native) non-human animal albumin protein and/or a propeptide from the endogenous (i.e., native) non-human animal albumin protein and/or a serum albumin from the endogenous (i.e., native) non-human animal albumin protein and/or. As one example, the albumin protein can comprise a human signal peptide, propeptide, and serum albumin.

Domains in a chimeric albumin protein that are from a human albumin protein can be encoded by a fully humanized sequence (i.e., the entire sequence encoding that domain is replaced with the orthologous human albumin sequence) or can be encoded by a partially humanized sequence (i.e., some of the sequence encoding that domain is replaced with the orthologous human albumin sequence, and the remaining endogenous (i.e., native) sequence encoding that domain encodes the same amino acids as the orthologous human albumin sequence such that the encoded domain is identical to that domain in the human albumin protein). Likewise, domains in a chimeric protein that are from the endogenous albumin protein cay be encoded by a fully endogenous sequence (i.e., the entire sequence encoding that domain is the endogenous albumin sequence) or can be encoded by a partially humanized sequence (i.e., some of the sequence encoding that domain is replaced with the orthologous human albumin sequence, but the orthologous human albumin sequence encodes the same amino acids as the replaced endogenous albumin sequence such that the encoded domain is identical to that domain in the endogenous albumin protein).

As one example, the albumin protein encoded by the humanized albumin locus can comprise a human albumin signal peptide. Optionally, the human albumin signal peptide comprises, consists essentially of, or consists of a sequence that is at least 85%, 90%, 95%, 96%, 97%, 98%, 99%, or 100% identical to SEQ ID NO: 6. Optionally, the human albumin signal peptide comprises, consists essentially of, or consists of a sequence that is at least about 85%, at least about 90%, at least about 95%, at least about 96%, at least about 97%, at least about 98%, at least about 99%, or about 100% identical to SEQ ID NO: 6. As another example, the albumin protein encoded by the humanized albumin locus can comprise a human albumin propeptide. Optionally, the human albumin propeptide comprises, consists essentially of, or consists of a sequence that is at least 85%, 90%, 95%, 96%, 97%, 98%, 99%, or 100% identical to SEQ ID NO: 7. Optionally, the human albumin propeptide comprises, consists essentially of, or consists of a sequence that is at least about 85%, at least about 90%, at least about 95%, at least about 96%, at least about 97%, at least about 98%, at least about 99%, or about 100% identical to SEQ ID NO: 7. As another example, the albumin protein encoded by the humanized albumin locus can comprise a human serum albumin. Optionally, the human serum albumin comprises, consists essentially of, or consists of a sequence that is at least 85%, 90%, 95%, 96%, 97%, 98%, 99%, or 100% identical to SEQ ID NO: 8. Optionally, the human serum albumin comprises, consists essentially of, or consists of a sequence that is at least about 85%, at least about 90%, at least about 95%, at least about 96%, at least about 97%, at least about 98%, at least about 99%, or about 100% identical to SEQ ID NO: 8. For example, the albumin protein encoded by the humanized albumin locus can comprise, consist essentially of, or consist of a sequence that is at least 85%, 90%, 95%, 96%, 97%, 98%, 99%, or 100% identical to SEQ ID NO: 5. For example, the albumin protein encoded by the humanized albumin locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 5. Optionally, the albumin CDS encoded by the humanized albumin locus can comprise, consist essentially of, or consist of a sequence that is at least 85%, 90%, 95%, 96%, 97%, 98%, 99%, or 100% identical to SEQ ID NO: 13 (or degenerates thereof). Optionally, the albumin CDS encoded by the humanized albumin locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 13 (or degenerates thereof).

The humanized albumin protein can retain the activity of the native albumin protein and/or the human albumin protein.

Optionally, a humanized albumin locus can comprise other elements. Examples of such elements can include selection cassettes, reporter genes, recombinase recognition sites, or other elements. Alternatively, the humanized albumin locus can lack other elements (e.g., can lack a selection marker or selection cassette). Examples of suitable reporter genes and reporter proteins are disclosed elsewhere herein.

Examples of suitable selection markers include neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized albumin locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized albumin locus (e.g., a humanized mouse albumin locus) is one in which a region from the start codon through the stop codon is replaced with the corresponding human sequence. See FIGS. 1A and 1B and SEQ ID NOS: 17 and 18. In a specific example, a region from the ATG start codon through the stop codon (i.e., coding exons 1-14) can be deleted from the non-human animal (e.g., mouse) albumin (Alb) locus, and a corresponding region of the human albumin (ALB) from the ATG start codon to about 100 bp downstream of the stop codon can be inserted in place of the deleted endogenous region.

C. Non-Human Animal Genomes, Non-Human Animal Cells, and Non-Human Animals Comprising a Humanized Albumin (ALB) Locus Non-human animal genomes, non-human animal cells, and non-human animals comprising a humanized albumin (ALB) locus as described elsewhere herein are provided. The genomes, cells, or non-human animals can be male or female. The genomes, cells, or non-human animals can be heterozygous or homozygous for the humanized albumin locus. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized albumin locus can comprise the humanized endogenous albumin locus in its germline.

The non-human animal genomes or cells provided herein can be, for example, any non-human animal genome or cell comprising an albumin locus or a genomic locus homologous or orthologous to the human albumin locus. The genomes can be from or the cells can be eukaryotic cells, which include, for example, fungal cells (e.g., yeast), plant cells, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized albumin locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/01a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

Non-human animals (e.g., mice or rats) comprising a humanized albumin locus (e.g., a homozygous humanized albumin locus) can express albumin from the humanized albumin locus such that serum albumin levels (e.g., serum human albumin levels) are comparable to serum albumin levels in control wild type non-human animals. In one example, non-human animals comprising a humanized albumin locus (e.g., a homozygous humanized albumin locus) can have serum albumin levels (e.g., serum human albumin levels) that are at least about 75%, at least about 80%, at least about 85%, at least about 90%, at least about 95%, or at least about 100% of serum albumin levels in a control wild type non-human animal. In another example, non-human animals comprising a humanized albumin locus (e.g., a homozygous humanized albumin locus) can have serum albumin levels (e.g., serum human albumin levels) that are at least as high as serum albumin levels in a control wild type non-human animal. In another example, non-human animals comprising a humanized albumin locus (e.g., a homozygous humanized albumin locus) can have serum albumin levels (e.g., serum human albumin levels) that are higher than serum albumin levels in a control wild type non-human animal. For example, a non-human animal comprising a humanized albumin locus (e.g., a homozygous humanized albumin locus) can have serum albumin levels (e.g., serum human albumin levels) of at least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 11 mg/mL, at least about 12 mg/mL, at least about 13 mg/mL, at least about 14 mg/mL, or at least about 15 mg/mL. In a more specific example, the non-human animal comprising a humanized albumin locus (e.g., a homozygous humanized albumin locus) can be a mouse and can have serum albumin levels (e.g., serum human albumin levels) of at least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 11 mg/mL, at least about 12 mg/mL, at least about 13 mg/mL, at least about 14 mg/mL, or at least about 15 mg/mL. In a specific example, the non-human animal (e.g., a mouse) comprising a humanized albumin locus (e.g., a homozygous humanized albumin locus) can have serum albumin levels (e.g., serum human albumin levels) of between about 10 mg/mL and about 15 mg/mL. In any of the above examples, the albumin encoded by the humanized albumin locus can comprise, for example, a human albumin signal peptide. For example, in one example, the entire albumin coding sequence of the endogenous albumin locus has been deleted and replaced with the corresponding human albumin sequence or the region of the endogenous albumin locus from the start codon to the stop codon has been deleted and replaced with the corresponding human albumin sequence.

III. Methods of Using Non-Human Animals Comprising a Humanized Albumin Locus for Assessing Efficacy of Human-Albumin-Targeting Reagents In Vivo or Ex Vivo Various methods are provided for using the non-human animals comprising a humanized albumin locus as described elsewhere herein for assessing or optimizing delivery or efficacy of human-albumin-targeting reagents (e.g., therapeutic molecules or complexes) in vivo or ex vivo. Because the non-human animals comprise a humanized albumin locus, the non-human animals will more accurately reflect the efficacy of a human-albumin-targeting reagent. Such non-human animals are particularly useful for testing genome-editing reagents designed to target the human albumin gene because the non-human animals disclosed herein comprise humanized endogenous albumin loci rather than transgenic insertions of human albumin sequence at random genomic loci, and the humanized endogenous albumin loci can comprise orthologous human genomic albumin sequence from both coding and non-coding regions rather than an artificial cDNA sequence.

A. Methods of Testing Efficacy of Human-Albumin-Targeting Reagents In Vivo or Ex Vivo Various methods are provided for assessing delivery or efficacy of human-albumin-targeting reagents in vivo using non-human animals comprising a humanized albumin locus as described elsewhere herein. Such methods can comprise: (a) introducing into the non-human animal a human-albumin-targeting reagent (i.e., administering the human-albumin-targeting reagent to the non-human animal); and (b) assessing the activity of the human-albumin-targeting reagent.

The human-albumin-targeting reagent can be any biological or chemical agent that targets the human albumin locus (the human albumin gene), the human albumin mRNA, or the human albumin protein. Examples of human-albumin-targeting reagents are disclosed elsewhere herein and include, for example, genome-editing agents. For example, the human-albumin-targeting reagent can be an albumin-targeting nucleic acid (e.g., CRISPR/Cas guide RNAs, short hairpin RNAs (shRNAs), or small interfering RNAs (siRNAs)) or nucleic acid encoding an albumin-targeting protein (e.g., a Cas protein such as Cas9, a ZFN, or a TALEN). Alternatively, the human-albumin-targeting reagent can be an albumin-targeting antibody or antigen-binding protein, or any other large molecule or small molecule that targets human albumin. In one example, the human-albumin-targeting reagent is a genome-editing agent such as a nuclease agent and/or an exogenous donor nucleic acid (e.g., a targeting vector). In a particular example, the genome-editing agent can target intron 1, intron 12, or intron 13 of the human albumin gene. For example, the genome-editing agent can target intron 1 of the human albumin gene.

Such human-albumin-targeting reagents can be administered by any delivery method (e.g., AAV, LNP, or HDD) as disclosed in more detail elsewhere herein and by any route of administration. Means of delivering therapeutic complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose. For example, in some methods in which the reagents (e.g., Cas9 mRNA and gRNA) are delivered by LNP-mediated delivery, the dose can be between about 0.01 and about 10 mg/kg, about 0.01 and about 5 mg/kg, between about 0.01 and about 4 mg/kg, between about 0.01 and about 3 mg/kg, between about 0.01 and about 2 mg/kg, between about 0.01 and about 1 mg/kg, between about 0.1 and about 10 mg/kg, between about 0.1 and about 6 mg/kg; between about 0.1 and about 5 mg/kg, between about 0.1 and about 4 mg/kg, between about 0.1 and about 3 mg/kg, between about 0.1 and about 2 mg/kg, between about 0.1 and about 1 mg/kg, between about 0.3 and about 10 mg/kg, between about 0.3 and about 6 mg/kg; between about 0.3 and about 5 mg/kg, between about 0.3 and about 4 mg/kg, between about 0.3 and about 3 mg/kg, between about 0.3 and about 2 mg/kg, between about 0.3 and about 1 mg/kg, about 0.1 mg/kg, about 0.3 mg/kg, about 1 mg/kg, about 2 mg/kg, or about 3 mg/kg. In a specific example, the dose is between about 0.1 and about 6 mg/kg; between about 0.1 and about 3 mg/kg, or between about 0.1 and about 2 mg/kg.

Methods for assessing activity of the human-albumin-targeting reagent are well-known and are provided elsewhere herein. Assessment of activity can be in any cell type, any tissue type, or any organ type as disclosed elsewhere herein. In some methods, assessment of activity is in liver cells. If the albumin-targeting reagent is a genome editing reagent (e.g., a nuclease agent), such methods can comprise assessing modification of the humanized albumin locus. As one example, the assessing can comprise measuring non-homologous end joining (NHEJ) activity at the humanized albumin locus. This can comprise, for example, measuring the frequency of insertions or deletions within the humanized albumin locus. For example, the assessing can comprise sequencing the humanized albumin locus in one or more cells isolated from the non-human animal (e.g., next-generation sequencing). Assessment can comprise isolating a target organ or tissue (e.g., liver) or tissue from the non-human animal and assessing modification of humanized albumin locus in the target organ or tissue. Assessment can also comprise assessing modification of humanized albumin locus in two or more different cell types within the target organ or tissue. Similarly, assessment can comprise isolating a non-target organ or tissue (e.g., two or more non-target organs or tissues) from the non-human animal and assessing modification of humanized albumin locus in the non-target organ or tissue.

Such methods can also comprise measuring expression levels of the mRNA produced by the humanized albumin locus, or by measuring expression levels of the protein encoded by the humanized albumin locus. For example, protein levels can be measured in a particular cell, tissue, or organ type (e.g., liver), or secreted levels can be measured in the serum. Methods for assessing expression of albumin mRNA or protein expressed from the humanized albumin locus are provided elsewhere herein and are well-known. As one example, the BASESCOPE™ RNA in situ hybridization (ISH) assay can be used, for example, to quantify cell-specific edited transcripts.

In some methods, the human-albumin-targeting reagent comprises an exogenous donor nucleic acid (e.g., targeting vector). Such exogenous donor nucleic acids can encode an exogenous protein not encoded or expressed by a wild type endogenous albumin locus (e.g., can comprise an insert nucleic acid that encodes an exogenous protein). In one example, the exogenous protein can be a heterologous protein comprising a human albumin signal peptide fused to a protein not encoded or expressed by a wild type endogenous albumin locus. In one example, the exogenous protein encoded by the exogenous donor nucleic acid once integrated into the humanized albumin locus can be a heterologous protein comprising a human albumin signal peptide fused to a protein not encoded or expressed by a wild type endogenous albumin locus. In some methods, assessment can comprise measuring expression of a messenger RNA encoded by the exogenous donor nucleic acid. Assessment can also comprise measuring expression of the exogenous protein. For example, expression of the exogenous protein can be measured in the liver of the non-human animal, or serum levels of the exogenous protein can be measured.

In some methods, the non-human animals comprising a humanized albumin locus as described elsewhere herein further comprise an inactivated (knocked out) endogenous gene that is not the albumin locus, and optionally the human-albumin-targeting reagent comprises an exogenous donor nucleic acid (e.g., targeting vector) encoding an exogenous protein to replace the function of the inactivated endogenous gene. In a specific example, the inactivated endogenous gene is F9, and the exogenous protein is coagulation factor IX (e.g., human coagulation factor IX).

In some methods, the human-albumin-targeting reagent comprises (1) a nuclease agent designed to target a region of a human albumin gene and (2) an exogenous donor nucleic acid, wherein the exogenous donor nucleic acid is designed to target the human albumin gene. The exogenous donor nucleic acid can, for example, encode an exogenous protein, optionally wherein the protein encoded by a humanized endogenous albumin locus that has been targeted with the exogenous donor nucleic acid is a heterologous protein comprising a human albumin signal peptide fused to the exogenous protein.

As one specific example, if the human-albumin-targeting reagent is a genome editing reagent (e.g., a nuclease agent), percent editing (e.g., total number of insertions or deletions observed over the total number of sequences read in the PCR reaction from a pool of lysed cells) at the humanized albumin locus can be assessed (e.g., in liver cells).

The various methods provided above for assessing activity in vivo can also be used to assess the activity of human-albumin-targeting reagents ex vivo as described elsewhere herein.

In some methods, the human-albumin-targeting reagent is a nuclease agent, such as a CRISPR/Cas nuclease agent, that targets the human albumin gene. Such methods can comprise, for example: (a) introducing into the non-human animal a nuclease agent designed to cleave the human albumin gene (e.g., Cas protein such as Cas9 and a guide RNA designed to target a guide RNA target sequence in the human albumin gene); and (b) assessing modification of the humanized albumin locus.

In the case of a CRISPR/Cas nuclease, for example, modification of the humanized albumin locus will be induced when the guide RNA forms a complex with the Cas protein and directs the Cas protein to the humanized albumin locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the human albumin gene. For example, two guide RNAs can be designed to excise a genomic sequence between the two guide RNA target sequences. Modification of the humanized albumin locus will be induced when the first guide RNA forms a complex with the Cas protein and directs the Cas protein to the humanized albumin locus, the second guide RNA forms a complex with the Cas protein and directs the Cas protein to the humanized albumin locus, the first Cas/guide RNA complex cleaves the first guide RNA target sequence, and the second Cas/guide RNA complex cleaves the second guide RNA target sequence, resulting in excision of the intervening sequence.

Additionally or alternatively, an exogenous donor nucleic acid (e.g., targeting vector) capable of recombining with and modifying a human albumin gene is also introduced into the non-human animal. Optionally, the nuclease agent or Cas protein can be tethered to the exogenous donor nucleic acid as described elsewhere herein. Modification of the humanized albumin locus will be induced, for example, when the guide RNA forms a complex with the Cas protein and directs the Cas protein to the humanized albumin locus, the Cas/guide RNA complex cleaves the guide RNA target sequence, and the humanized albumin locus recombines with the exogenous donor nucleic acid to modify the humanized albumin locus. The exogenous donor nucleic acid can recombine with the humanized albumin locus, for example, via homology-directed repair (HDR) or via NHEJ-mediated insertion. Any type of exogenous donor nucleic acid can be used, examples of which are provided elsewhere herein.

In some methods, the human-albumin-targeting reagent comprises an exogenous donor nucleic acid (e.g., targeting vector). Such exogenous donor nucleic acids can encode an exogenous protein not encoded or expressed by a wild type endogenous albumin locus (e.g., can comprise an insert nucleic acid that encodes an exogenous protein). In one example, the exogenous protein can be a heterologous protein comprising a human albumin signal peptide fused to a protein not encoded or expressed by a wild type endogenous albumin locus. For example, the exogenous donor nucleic acid can be a promoterless cassette comprising a splice acceptor, and the exogenous donor nucleic acid can be targeted to the first intron of human albumin.

B. Methods of Optimizing Delivery or Efficacy of Human-Albumin-Targeting Reagent In Vivo or Ex Vivo Various methods are provided for optimizing delivery of human-albumin-targeting reagents to a cell or non-human animal or optimizing the activity or efficacy of human-albumin-targeting reagents in vivo. Such methods can comprise, for example: (a) performing the method of testing the efficacy of a human-albumin-targeting reagent as described above a first time in a first non-human animal or first cell comprising a humanized albumin locus; (b) changing a variable and performing the method a second time in a second non-human animal (i.e., of the same species) or a second cell comprising a humanized albumin locus with the changed variable; and (c) comparing the activity of the human-albumin-targeting reagent in step (a) with the activity of the human-albumin-targeting reagent in step (b), and selecting the method resulting in the higher activity.

Methods of measuring delivery, efficacy, or activity of human-albumin-targeting reagents are disclosed elsewhere herein. For example, such methods can comprise measuring modification of the humanized albumin locus. More effective modification of the humanized albumin locus can mean different things depending on the desired effect within the non-human animal or cell. For example, more effective modification of the humanized albumin locus can mean one or more or all of higher levels of modification, higher precision, higher consistency, or higher specificity. Higher levels of modification (i.e., higher efficacy) of the humanized albumin locus refers to a higher percentage of cells is targeted within a particular target cell type, within a particular target tissue, or within a particular target organ (e.g., liver). Higher precision refers to more precise modification of the humanized albumin locus (e.g., a higher percentage of targeted cells having the same modification or having the desired modification without extra unintended insertions and deletions (e.g., NHEJ indels)). Higher consistency refers to more consistent modification of the humanized albumin locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which the human-albumin-targeting reagent or reagents are introduced into the cell or non-human animal. Examples of delivery methods, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-albumin-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-albumin-targeting reagent or reagents introduced. As another example, the changed variable can be the concentration or the amount of one human-albumin-targeting reagent introduced (e.g., guide RNA, Cas protein, or exogenous donor nucleic acid) relative to the concentration or the amount another human-albumin-targeting reagent introduced (e.g., guide RNA, Cas protein, or exogenous donor nucleic acid).

As another example, the changed variable can be the timing of introducing the human-albumin-targeting reagent or reagents relative to the timing of assessing the activity or efficacy of the reagents. As another example, the changed variable can be the number of times or frequency with which the human-albumin-targeting reagent or reagents are introduced. As another example, the changed variable can be the timing of introduction of one human-albumin-targeting reagent introduced (e.g., guide RNA, Cas protein, or exogenous donor nucleic acid) relative to the timing of introduction of another human-albumin-targeting reagent introduced (e.g., guide RNA, Cas protein, or exogenous donor nucleic acid).

As another example, the changed variable can be the form in which the human-albumin-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth.

As another example, the changed variable can be the human-albumin-targeting reagent or reagents that are introduced. For example, if the human-albumin-targeting reagent comprises a guide RNA, the changed variable can be introducing a different guide RNA with a different sequence (e.g., targeting a different guide RNA target sequence). Likewise, if the human-albumin-targeting reagent comprises a Cas protein, the changed variable can be introducing a different Cas protein (e.g., introducing a different Cas protein with a different sequence, or a nucleic acid with a different sequence (e.g., codon-optimized) but encoding the same Cas protein amino acid sequence. Likewise, if the human-albumin-targeting reagent comprises an exogenous donor nucleic acid, the changed variable can be introducing a different exogenous donor nucleic acid with a different sequence (e.g., a different insert nucleic acid or different homology arms (e.g., longer or shorter homology arms or homology arms targeting a different region of the human albumin gene)).

In a specific example, the human-albumin-targeting reagent comprises a Cas protein and a guide RNA designed to target a guide RNA target sequence in a human albumin gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-Albumin-Targeting Reagents

A human-albumin-targeting reagent can be any reagent that targets a human albumin gene, a human albumin mRNA, or a human albumin protein. For example, it can be a genome-editing reagent such as a nuclease agent that cleaves a target sequence within the human albumin gene and/or an exogenous donor sequence that recombines with a human albumin gene, it can be an antisense oligonucleotide targeting a human albumin mRNA, it can be an antigen-binding protein targeting an epitope of a human albumin protein, or it can be a small molecule targeting human albumin. Human-albumin-targeting reagents in the methods disclosed herein can be known human-albumin-targeting reagents, can be putative-albumin-targeting reagents (e.g., candidate reagents designed to target human albumin), or can be reagents being screened for human-albumin-targeting activity.

(1) Nuclease Agents Targeting Human Albumin Gene

A human-albumin-targeting reagent can be a genome editing reagent such as a nuclease agent that cleaves a target sequence within the human albumin gene. A nuclease target sequence includes a DNA sequence at which a nick or double-strand break is induced by a nuclease agent. The target sequence for a nuclease agent can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell. In a particular example, the nuclease target sequence can be in intron 1, intron 12, or intron 13 of the human albumin gene. For example, the nuclease target sequence can be in intron 1 of the human albumin gene.

The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) Methods in Enzymology 476:295-307, which is incorporated by reference herein in its entirety for all purposes.

The target sequence of the nuclease agent can be positioned anywhere in or near the albumin locus. The target sequence can be located within a coding region of the albumin gene, or within regulatory regions that influence the expression of the gene. A target sequence of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148, each of which is herein incorporated by reference in its entirety.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2;

US20130123484; US20100291048; WO/2011/017293A2; and Gaj et al. (2013) *Trends in Biotechnology*, 31(7):397-405, each of which is herein incorporated by reference.

Another type of nuclease agent is an engineered meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) *Crit Rev Biochem Mol Biot* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346, each of which is herein incorporated by reference in its entirety.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Nuclease agents can further comprise CRISPR/Cas systems as described in more detail below.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The nuclease agent may be introduced into a cell or non-human animal by any known means. A polypeptide encoding the nuclease agent may be directly introduced into the cell or non-human animal. Alternatively, a polynucleotide encoding the nuclease agent can be introduced into the cell or non-human animal. When a polynucleotide encoding the nuclease agent is introduced, the nuclease agent can be transiently, conditionally, or constitutively expressed within the cell. The polynucleotide encoding the nuclease agent can be contained in an expression cassette and be operably linked to a conditional promoter, an inducible promoter, a constitutive promoter, or a tissue-specific promoter. Examples of promoters are discussed in further detail elsewhere herein. Alternatively, the nuclease agent can be introduced into the cell as an mRNA encoding the nuclease agent.

A polynucleotide encoding a nuclease agent can be stably integrated in the genome of a cell and operably linked to a promoter active in the cell. Alternatively, a polynucleotide encoding a nuclease agent can be in a targeting vector.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given eukaryotic cell of interest, including a human cell, a non-human cell, a mammalian cell, a rodent cell, a mouse cell, a rat cell or any other host cell of interest, as compared to the naturally occurring polynucleotide sequence.

(2) CRISPR/Cas Systems Targeting Human Albumin Gene

A particular type of human-albumin-targeting reagent can be a Clustered Regularly Interspersed Short Palindromic Repeats (CRISPR)/CRISPR-associated (Cas) system that targets the human albumin gene. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins and Polynucleotides Encoding Cas Proteins. Cas proteins generally comprise at least one RNA recognition or binding domain that can interact with guide RNAs (gRNAs). Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.*

Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. An exemplary Cas9 protein sequence can comprise, consist essentially of, or consist of SEQ ID NO: 38. An exemplary DNA encoding the Cas9 protein can comprise, consist essentially of, or consist of SEQ ID NO: 39.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens,* and *Porphyromonas macacae.* Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins (e.g., nuclease-active Cas proteins or nuclease-inactive Cas proteins) can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. In one example, the exogenous donor nucleic acid or labeled nucleic acid is tethered to the C-terminus or the N-terminus of the Cas protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. For example, the Cas protein can be tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs. A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 40). Any of the DNA-targeting segments disclosed herein can be joined to the 5' end of SEQ ID NO: 40 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of (SEQ ID NO: 41)
AGCAUAGCAAGUUAAAAUAAGGCUAGUCCGUUAUCAACUUGAAAAGUG

GCACCGAGUCGGUGCUUU.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment joined to a scaffold sequence (i.e., the protein-binding or Cas-binding sequence of the guide RNA). For example, such guide RNAs can have a 5' DNA-targeting segment and a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACCGAGUCGGUGCU (version 1; SEQ ID NO: 42); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 43); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 44); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 45). Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 42-45 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) Cell Reports 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) Nat. Biotech. 35(12): 1179-1187, herein incorporated by reference in its entirety for all purposes. Other examples of modified guide RNAs are provided, e.g., in WO 2018/107028 A1, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

Guide RNA Target Sequences. Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both. In a particular example, the guide RNA target sequence can be in intron 1, intron 12, or intron 13 of the human albumin gene. For example, the guide RNA target sequence can be in intron 1 of the human albumin gene.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-$CCN_2$-3', where N2 is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 46) or $N_{20}NGG$ (SEQ ID NO: 47). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 48) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 46-48, including the 5' G or GG and the 3' GG or NGG. Yet other guide RNA target sequences PAMs can have between 14 and 20 nucleotides in length of SEQ ID NOS: 46-48.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

(3) Exogenous Donor Nucleic Acids Targeting Human Albumin Gene

The methods and compositions disclosed herein can utilize exogenous donor nucleic acids to modify the humanized albumin locus following cleavage of the humanized albumin locus with a nuclease agent or independent of cleavage of the humanized albumin locus with a nuclease agent. In such methods using a nuclease agent, the nuclease agent protein cleaves the humanized albumin locus to create a single-strand break (nick) or double-strand break, and the exogenous donor nucleic acid recombines the humanized albumin locus via non-homologous end joining (NHEJ)-mediated ligation or through a homology-directed repair event. Optionally, repair with the exogenous donor nucleic acid removes or disrupts the nuclease target sequence so that alleles that have been targeted cannot be re-targeted by the nuclease agent.

The exogenous donor nucleic acid can target any sequence in the human albumin gene. Some exogenous donor nucleic acids comprise homology arms. Other exogenous donor nucleic acids do not comprise homology arms. The exogenous donor nucleic acids can be capable of insertion into a humanized albumin locus by homology-directed repair, and/or they can be capable of insertion into a humanized albumin locus by non-homologous end joining. In one example, the exogenous donor nucleic acid (e.g., a targeting vector) can target intron 1, intron 12, or intron 13 of the human albumin gene. For example, the exogenous donor nucleic acid can target intron 1 of the human albumin gene.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) *Nat. Commun.* 7:10431, herein incorporated by reference in its entirety for all purposes. Exogenous donor nucleic acids can be naked nucleic acids or can be delivered by viruses, such as AAV. In a specific example, the exogenous donor nucleic acid can be delivered via AAV and can be capable of insertion into a humanized albumin locus by non-homologous end joining (e.g., the exogenous donor nucleic acid can be one that does not comprise homology arms).

An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE® 700).

Exogenous donor nucleic acids can also comprise nucleic acid inserts including segments of DNA to be integrated at the humanized albumin locus. Integration of a nucleic acid insert at a humanized albumin locus can result in addition of a nucleic acid sequence of interest to the humanized albumin locus, deletion of a nucleic acid sequence of interest at the humanized albumin locus, or replacement of a nucleic acid sequence of interest at the humanized albumin locus (i.e., deletion and insertion). Some exogenous donor nucleic acids are designed for insertion of a nucleic acid insert at the humanized albumin locus without any corresponding deletion at the humanized albumin locus. Other exogenous donor nucleic acids are designed to delete a nucleic acid sequence of interest at the humanized albumin locus without any corresponding insertion of a nucleic acid insert. Yet other exogenous donor nucleic acids are designed to delete a nucleic acid sequence of interest at the humanized albumin locus and replace it with a nucleic acid insert.

The nucleic acid insert or the corresponding nucleic acid at the humanized albumin locus being deleted and/or replaced can be various lengths. An exemplary nucleic acid insert or corresponding nucleic acid at the humanized albumin locus being deleted and/or replaced is between about 1 nucleotide to about 5 kb in length or is between about 1 nucleotide to about 1,000 nucleotides in length. For example, a nucleic acid insert or a corresponding nucleic acid at the humanized albumin locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the humanized albumin locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the humanized albumin locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the humanized albumin locus. Optionally, such point mutations can result in a conservative amino acid substitution (e.g., substitution of aspartic acid [Asp, D] with glutamic acid [Glu, E]) in the encoded polypeptide.

Some exogenous donor nucleic acids can encode an exogenous protein not encoded or expressed by a wild type endogenous albumin locus (e.g., can comprise an insert nucleic acid that encodes an exogenous protein). In one example, a humanized albumin locus targeted by the exogenous donor nucleic acid can encode a heterologous protein comprising a human albumin signal peptide fused to a protein not encoded or expressed by a wild type endogenous albumin locus. For example, the exogenous donor nucleic acid can be a promoterless cassette comprising a splice acceptor, and the exogenous donor nucleic acid can be targeted to the first intron of human albumin.

Donor Nucleic Acids for Non-Homologous-End-Joining-Mediated Insertion. Some exogenous donor nucleic acids are capable of insertion into a humanized albumin locus by non-homologous end joining. In some cases, such exogenous donor nucleic acids do not comprise homology arms. For example, such exogenous donor nucleic acids can be inserted into a blunt end double-strand break following cleavage with a nuclease agent. In a specific example, the exogenous donor nucleic acid can be delivered via AAV and can be capable of insertion into a humanized albumin locus by non-homologous end joining (e.g., the exogenous donor nucleic acid can be one that does not comprise homology arms). In a specific example, the exogenous donor nucleic acid can be inserted via homology-independent targeted integration. For example, the insert sequence in the exogenous donor nucleic acid to be inserted into a humanized albumin locus can be flanked on each side by a target site for a nuclease agent (e.g., the same target site as in the humanized albumin locus, and the same nuclease agent being used to cleave the target site in the humanized albumin locus). The nuclease agent can then cleave the target sites flanking the insert sequence. In a specific example, the exogenous donor nucleic acid is delivered AAV-mediated delivery, and cleavage of the target sites flanking the insert sequence can remove the inverted terminal repeats (ITRs) of the AAV. In some methods, the target site in the humanized albumin locus (e.g., a gRNA target sequence including the flanking protospacer adjacent motif) is no longer present if the insert sequence is inserted into the humanized albumin locus in the correct orientation but it is reformed if the insert sequence is inserted into the humanized albumin locus in the opposite orientation. This can help ensure that the insert sequence is inserted in the correct orientation for expression.

Other exogenous donor nucleic acids have short single-stranded regions at the 5' end and/or the 3' end that are complementary to one or more overhangs created by nuclease-mediated cleavage at the humanized albumin locus. These overhangs can also be referred to as 5' and 3' homology arms. For example, some exogenous donor nucleic acids have short single-stranded regions at the 5' end and/or the 3' end that are complementary to one or more overhangs created by nuclease-mediated cleavage at 5' and/or 3' target sequences at the humanized albumin locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the humanized albumin locus or only at the 3' end complementary to an overhang created at a 3' target sequence at the humanized albumin locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by nuclease-mediated cleavage at the humanized albumin locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

Donor Nucleic Acids for Insertion by Homology-Directed Repair. Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the humanized albumin locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a nuclease agent is used in combination with an exogenous donor nucleic acid, the 5' and 3' target sequences are preferably located in sufficient proximity to the nuclease cleavage site (e.g., within sufficient proximity to a the nuclease target sequence) so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the targeted locus that correspond to the 5' and 3' homology arms of the exogenous donor nucleic acid are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor nucleic acid can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor nucleic acid and the nuclease cleavage site can vary. For example, target sequences can be located 5' to the nuclease cleavage site, target sequences can be located 3' to the nuclease cleavage site, or the target sequences can flank the nuclease cleavage site.

(4) Other Human-Albumin-Targeting Reagents

The activity of any other known or putative human-albumin-targeting reagent can also be assessed using the non-human animals disclosed herein. Similarly, any other molecule can be screened for human-albumin-targeting activity using the non-human animals disclosed herein.

Examples of other human-albumin-targeting reagents include antisense oligonucleotides (e.g., siRNAs or shRNAs) that act through RNA interference (RNAi). Antisense oligonucleotides (ASOs) or antisense RNAs are short synthetic strings of nucleotides designed to prevent the expression of a targeted protein by selectively binding to the RNA that encodes the targeted protein and thereby preventing translation. These compounds bind to RNA with high affinity and selectivity through well characterized Watson-Crick base pairing (hybridization). RNA interference (RNAi) is an endogenous cellular mechanism for controlling gene expression in which small interfering RNAs (siRNAs) that are bound to the RNA-induced silencing complex (RISC) mediate the cleavage of target messenger RNA (mRNA).

Other human-albumin-targeting reagents include antibodies or antigen-binding proteins designed to specifically bind a human albumin epitope. Other human-albumin-targeting reagents include small-molecule reagents.

D. Administering Human-Albumin-Targeting Reagents to Non-Human Animals or Cells

The methods disclosed herein can comprise introducing into a non-human animal or cell various molecules (e.g., human-albumin-targeting reagents such as therapeutic molecules or complexes), including, for example, nucleic acids, proteins, nucleic-acid-protein complexes, or protein complexes. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a molecule (e.g., a nucleic acid or protein) into a cell or non-human animal. Methods for introducing molecules into various cell types are known and include, for example, stable transfection methods, transient transfection methods, and virus-mediated methods.

Transfection protocols as well as protocols for introducing molecules into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). *Transfer and Expression: A Laboratory Manual. New York: W. H. Freeman and Company*. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of molecules (e.g., nucleic acids or proteins) into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109: 9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4):694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as 5010, 5024, 5027, 5031, or 5033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Reports 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) Cell Reports 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino)propoxy)carbonyl)oxy)hexadecanoyl)oxy)propane-1,3-diyl (9Z,9′Z,12Z,12′Z)-bis(octadeca-9,12-dienoate). Another example of a suitable lipid is Lipid D, which is 3-(((3-(dimethylamino)propoxy)carbonyl)oxy)-13-(octanoyloxy)tridecyl 3-octylundecanoate. Other suitable lipids include heptatriaconta-6,9,28,31-tetraen-19-yl 4-(dimethylamino)butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), di stearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lyso-phosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl) oxy)-2-((((3-(diethylamino)propoxy)carbonyl)oxy)methyl) propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by MEW molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-Albumin-Targeting Reagents In Vivo or Ex Vivo The methods disclosed herein can further comprise detecting or measuring activity of human-albumin-targeting reagents. For example, if the human-albumin-targeting reagent is a genome editing reagent (e.g., CRISPR/Cas designed to target the human albumin locus), the measuring can comprise assessing the humanized albumin locus for modifications.

Various methods can be used to identify cells having a targeted genetic modification. The screening can comprise a quantitative assay for assessing modification-of-allele (MOA) of a parental chromosome. See, e.g., US 2004/0018626; US 2014/0178879; US 2016/0145646; WO 2016/081923; and Frendewey et al. (2010)*Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized albumin locus in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-albumin-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized albumin locus, affect expression of the humanized albumin locus, prevent translation of the humanized albumin mRNA, or clear the humanized albumin protein, the measuring can comprise assessing humanized albumin mRNA or protein expression. This measuring can be within the liver or particular cell types or regions within the liver, or it can involve measuring serum levels of secreted humanized albumin protein.

If the reagent is an exogenous donor nucleic acid encoding an exogenous protein not encoded or expressed by a wild type endogenous albumin locus, the measuring can comprise assessing expression of the mRNA encoded by the exogenous donor nucleic acid or assessing expression of the exogenous protein. This measuring can be within the liver or particular cell types or regions within the liver, or it can involve measuring serum levels of secreted exogenous protein. In a specific example, the exogenous protein is a factor IX protein. Optionally, the assessing comprises measuring serum levels of the factor IX protein in the non-human animal and/or comprises assessing activated partial thromboplastin time or performing a thrombin generation assay. Optionally, the non-human animal further comprises an inactivated F9 locus, and the assessing comprises measuring serum levels of the factor IX protein in the non-human animal and/or comprises assessing activated partial thromboplastin time (aPTT) or performing a thrombin generation assay (TGA). These assays are described in more detail in the examples.

One example of an assay that can be used is the BASESCOPE™ RNA in situ hybridization (ISH) assay, which a method that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe, and it can differentially detect single nucleotide edits and mutations in intact fixed tissue.

Production and secretion of the humanized albumin protein or exogenous protein can be assessed by any known means. For example, expression can be assessed by measuring levels of the encoded mRNA in the liver of the non-human animal or levels of the encoded protein in the liver of the non-human animal using known assays. Secretion of the humanized albumin protein or exogenous protein can be assessed by measuring or plasma levels or serum levels of the encoded humanized albumin protein or exogenous protein in the non-human animal using known assays.

IV. Methods of Making Non-Human Animals Comprising a Humanized Albumin Locus

Various methods are provided for making a non-human animal genome, non-human animal cell, or non-human animal comprising a humanized albumin (ALB) locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted albumin locus.

For example, the method of producing a non-human animal comprising a humanized albumin locus can comprise: (1) modifying the genome of a pluripotent cell to comprise the humanized albumin locus; (2) identifying or selecting the genetically modified pluripotent cell comprising the humanized albumin locus; (3) introducing the genetically modified pluripotent cell into a non-human animal host embryo; and (4) implanting and gestating the host embryo in a surrogate mother. For example, the method of producing a non-human animal comprising a humanized albumin locus can comprise: (1) modifying the genome of a pluripotent cell to comprise the humanized albumin locus; (2) identifying or selecting the genetically modified pluripotent cell comprising the humanized albumin locus; (3) introducing the genetically modified pluripotent cell into a non-human animal host embryo; and (4) gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized albumin locus.

The methods can further comprise identifying a cell or animal having a modified target genomic locus. Various methods can be used to identify cells and animals having a targeted genetic modification.

The step of modifying the genome can, for example, utilize exogenous donor nucleic acids (e.g., targeting vectors) to modify an albumin locus to comprise a humanized albumin locus disclosed herein. As one example, the targeting vector can be for generating a humanized albumin gene at an endogenous albumin locus (e.g., endogenous non-human animal albumin locus), wherein the targeting vector comprises a 5' homology arm targeting a 5' target sequence at the endogenous albumin locus and a 3' homology arm targeting a 3' target sequence at the endogenous albumin locus. Exogenous donor nucleic acids can also comprise nucleic acid inserts including segments of DNA to be integrated in the albumin locus. Integration of a nucleic acid insert in the albumin locus can result in addition of a nucleic acid sequence of interest in the albumin locus, deletion of a nucleic acid sequence of interest in the albumin locus, or replacement of a nucleic acid sequence of interest in the albumin locus (i.e., deletion and insertion). The homology arms can flank an insert nucleic acid comprising human albumin sequence to generate the humanized albumin locus (e.g., for deleting a segment of the endogenous albumin locus and replacing with an orthologous human albumin sequence).

The exogenous donor nucleic acids can be for non-homologous-end-joining-mediated insertion or homologous recombination. Exogenous donor nucleic acids can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous donor nucleic acids can also comprise a heterologous sequence that is not present at an untargeted endogenous albumin locus. For example, an exogenous donor nucleic acids can comprise a selection cassette, such as a selection cassette flanked by recombinase recognition sites.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the albumin locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the endogenous albumin locus is included in an insert nucleic acid flanked by the homology arms.

In cells other than one-cell stage embryos, the exogenous donor nucleic acid can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites, wherein the insert nucleic acid comprises a human albumin sequence to generate a humanized albumin locus; and (b) identifying at least one cell comprising in its genome the insert nucleic acid integrated at the endogenous albumin locus (i.e., identifying at least one cell comprising the humanized albumin locus). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized albumin locus; and (b) identifying at least one cell comprising in its genome the insert nucleic acid integrated at the target genomic locus.

Alternatively, the modified pluripotent cell can be generated by (a) introducing into the cell: (i) a nuclease agent, wherein the nuclease agent induces a nick or double-strand break at a target site within the endogenous albumin locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human albumin sequence to generate a humanized albumin locus; and (c) identifying at least one cell comprising in its genome the insert nucleic acid integrated at the endogenous albumin locus (i.e., identifying at least one cell comprising the humanized albumin locus). Alternatively, the modified pluripotent cell can be generated by (a) introducing into the cell: (i) a nuclease agent or a nucleic acid encoding the nuclease agent, wherein the nuclease agent induces a nick or double-strand break at a target site within the endogenous albumin locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human albumin sequence to generate a humanized albumin locus; and (c) identifying at least one cell comprising in its genome the insert nucleic acid integrated at the endogenous albumin locus (i.e., identifying at least one cell comprising the humanized albumin locus). Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized albumin locus; and (c) identifying at least one cell comprising a modification (e.g., integration of the insert nucleic acid) at the target genomic locus. Any nuclease agent that induces a nick or double-strand break into a desired recognition site can be used. Alternatively, the modified pluripotent cell can be generated by (a) introducing into the cell: (i) a nuclease agent or a nucleic acid encoding the nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized albumin locus; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9).

See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized albumin locus using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the humanized albumin locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized albumin locus. It is recognized that depending on the method used to generate the F0 animal, the number of cells within the F0 animal that have the humanized albumin locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized albumin locus or can be homozygous for the humanized albumin locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
| --- | --- | --- |
| 1 | Protein | Mouse Albumin Protein (P07724.3; NP_033784.2) |
| 2 | Protein | Mouse Albumin Protein - Signal Peptide |
| 3 | Protein | Mouse Albumin Protein - Propeptide |
| 4 | Protein | Mouse Albumin Protein - Serum Albumin |

TABLE 2-continued

Description of Sequences.

| SEQ ID NO | Type | Description |
|---|---|---|
| 5 | Protein | Human Albumin Protein (P02768.2; NP_000468.1) |
| 6 | Protein | Human Albumin Protein - Signal Peptide |
| 7 | Protein | Human Albumin Protein - Propeptide |
| 8 | Protein | Human Albumin Protein - Serum Albumin |
| 9 | DNA | Mouse Alb CDS |
| 10 | DNA | Mouse Alb CDS - Signal Peptide |
| 11 | DNA | Mouse Alb CDS - Propeptide |
| 12 | DNA | Mouse Alb CDS - Serum Albumin |
| 13 | DNA | Human ALB CDS |
| 14 | DNA | Human ALB CDS - Signal Peptide |
| 15 | DNA | Human ALB CDS - Propeptide |
| 16 | DNA | Human ALB CDS - Serum Albumin |
| 17 | DNA | MAID 7626 Allele (ALB Humanized Region with Neo Self-Deleting Cassette) |
| 18 | DNA | MAID 7627 Allele (ALB Humanized Region, Cassette-Deleted) |
| 19 | DNA | A - 5' Mouse/5' Human Junction |
| 20 | DNA | B - Human/XhoI/LoxP Cassette Junction |
| 21 | DNA | C - Cassette loxP/I-CeuI/NheI/Mouse Junction |
| 22 | DNA | D - Human/XhoI/LoxP/I-CeuI/NheI/Mouse Junction |
| 23 | DNA | 7626hTU - Fwd |
| 24 | DNA | 7626hTU - Probe |
| 25 | DNA | 7626hTU - Rev |
| 26 | DNA | 7626hTD - Fwd |
| 27 | DNA | 7626hTD - Probe |
| 28 | DNA | 7626hTD - Rev |
| 29 | DNA | 7626mTU - Fwd |
| 30 | DNA | 7626mTU - Probe |
| 31 | DNA | 7626mTU - Rev |
| 32 | DNA | 7626mTD - Fwd |
| 33 | DNA | 7626mTD - Probe |
| 34 | DNA | 7626mTD - Rev |
| 35 | DNA | Human Albumin Sequence in MAID 7626 and MAID 7627 Alleles |
| 36 | DNA | Mouse Albumin mRNA (NM_009654A) |
| 37 | DNA | Human Albumin mRNA (NM_000477.7) |
| 38 | Protein | Cas9 |
| 39 | DNA | Cas9 |
| 40 | RNA | crRNA Tail |
| 41 | RNA | TracrRNA |
| 42 | RNA | Guide RNA Scaffold v1 |
| 43 | RNA | Guide RNA Scaffold v2 |
| 44 | RNA | Guide RNA Scaffold v3 |
| 45 | RNA | Guide RNA Scaffold v4 |
| 46 | DNA | Guide RNA Target Sequence Plus PAM v1 |
| 47 | DNA | Guide RNA Target Sequence Plus PAM v1 |
| 48 | DNA | Guide RNA Target Sequence Plus PAM v1 |
| 49 | RNA | G009844 Guide Sequence |
| 50 | RNA | G009852 Guide Sequence |
| 51 | RNA | G009857 Guide Sequence |
| 52 | RNA | G009859 Guide Sequence |
| 53 | RNA | G009860 Guide Sequence |
| 54 | RNA | G009874 Guide Sequence |
| 55 | RNA | G012752 Guide Sequence |
| 56 | RNA | G012753 Guide Sequence |
| 57 | RNA | G012761 Guide Sequence |
| 58 | RNA | G012764 Guide Sequence |
| 59 | RNA | G012765 Guide Sequence |
| 60 | RNA | G012766 Guide Sequence |
| 61 | RNA | G009864 Guide Sequence |
| 62 | RNA | G000666 Guide Sequence |
| 63 | DNA | Bidirectional hF9 Insertion Template |
| 64 | DNA | CAGG-hF9 Construct |

EXAMPLES

Example 1. Generation of Mice Comprising a Humanized Albumin (ALB) Locus

A large targeting vector (LTVEC) comprising a 5' homology arm comprising 20 kb of the mouse albumin (Alb) locus (from bMQ-127G8) and 3' homology arm comprising 127 kb of the mouse albumin (Alb) locus (from bMQ-127G8) was generated to replace a region of 14.4 kb (14,376 bp) from the mouse albumin (Alb) gene with 17.3 kb (17,335 bp) of the corresponding human sequence of albumin (ALB) (from RP11-31P12). Information on mouse and human albumin is provided in Table 3. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

TABLE 3

Mouse and Human Albumin (ALB).

| | Official Symbol | NCBI Gene ID | Primary Source | RefSeq mRNA ID | UniProt ID | Genomic Assembly | Location |
|---|---|---|---|---|---|---|---|
| Mouse | Alb | 11657 | MGI: 87991 | NM_009654 | P07724 | GRCm38.p4 | Chr 5: 90,460,870 ... 90,476,602 (+) |
| Human | ALB | 213 | HGNC: 399 | NM_000477 | P02768 | GRCh38.p12 | Chr 4: 73404239 ... 73421484 (+) |

Specifically, a region from the ATG start codon through the stop codon (i.e., coding exons 1-14) was deleted from the mouse albumin (Alb) locus. A corresponding region of the human albumin (ALB) from the ATG start codon to 100 bp downstream of the stop codon was inserted in place of the deleted mouse region. A loxP-mPrm1-Crei-pA-hUb1-em7-Neo-pA-loxP cassette (4,766 bp) was inserted downstream of the human 3' UTR, with a buffer of ~100 bp of 3' human sequence after the 3' UTR just before the cassette. This is the MAID 7626 allele. See FIG. 1A. After cassette deletion, loxP and cloning sites (38 bp) remained downstream of the human 3' UTR, with a buffer of 100 bp of 3' human sequence after the 3' UTR just before the remaining loxP site. This is the MAID 7627 allele. See FIG. 1B.

Sequences for the mouse albumin signal peptide, propeptide, and serum albumin are set forth in SEQ ID NOS: 2-4, respectively, with the corresponding coding sequences set forth in SEQ ID NOS: 10-12, respectively. Sequences for the human albumin signal peptide, propeptide, and serum albumin are set forth in SEQ ID NOS: 6-8, respectively, with the corresponding coding sequences set forth in SEQ ID NOS: 14-16, respectively. The expected encoded humanized albumin protein is identical to the human albumin protein. See FIGS. 1A and 1B. An alignment of the mouse and human albumin proteins along with the humanized albumin protein is provided in FIGS. 3A-3B. The mouse and human Alb/ALB coding sequences are set forth in SEQ ID NOS: 9 and 13, respectively. The mouse and human albumin protein sequences are set forth in SEQ ID NOS: 1 and 5, respectively. The sequences for the expected humanized ALB coding sequence and the expected humanized albumin protein are set forth in SEQ ID NOS: 13 and 5, respectively.

To generate the mutant allele, the large targeting vector described above was introduced into F1H4 mouse embryonic stem cells. F1H4 mouse ES cells were derived from hybrid embryos produced by crossing a female C57BL/6NTac mouse to a male 12956/SvEvTac mouse. See, e.g., US 2015-0376651 and WO 2015/200805, each of which is herein incorporated by reference in its entirety for all purposes. Following antibiotic selection, colonies were picked, expanded, and screened by TAQMAN®. See FIG. 2. Loss-of-allele assays were performed to detect loss of the endogenous mouse allele, and gain-of-allele assays were performed to detect gain of the humanized allele using the primers and probes set forth in Table 4.

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

F0 mice were generated from the modified ES cells using the VELOCIMOUSE® method. Specifically, mouse ES cell clones comprising the humanized albumin locus described above that were selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived. In the VELOCIMOUSE® method, the injected pre-morula stage embryos were cultured to the blastocyst stage, and the blastocyst-stage embryos are introduced into and gestated in surrogate mothers to produce the F0 generation mice. When starting with mouse ES cell clones homozygous for the targeted modification, F0 mice homozygous for the targeted modification are produced. When starting with mouse ES cell clones heterozygous for the targeted modification, subsequent breeding can be performed to produce mice homozygous for the targeted modification.

Example 2. Validation of Mice Comprising a Humanized Albumin (ALB) Locus

To validate the humanized albumin mice, mouse and human albumin levels were measured in plasma samples using human and mouse serum albumin ELISA kits (Abcam ab179887 and ab207620, respectively). The humanized mice used for the validation were F1 mice in which the

TABLE 4

Screening Assays.

Figure 4:
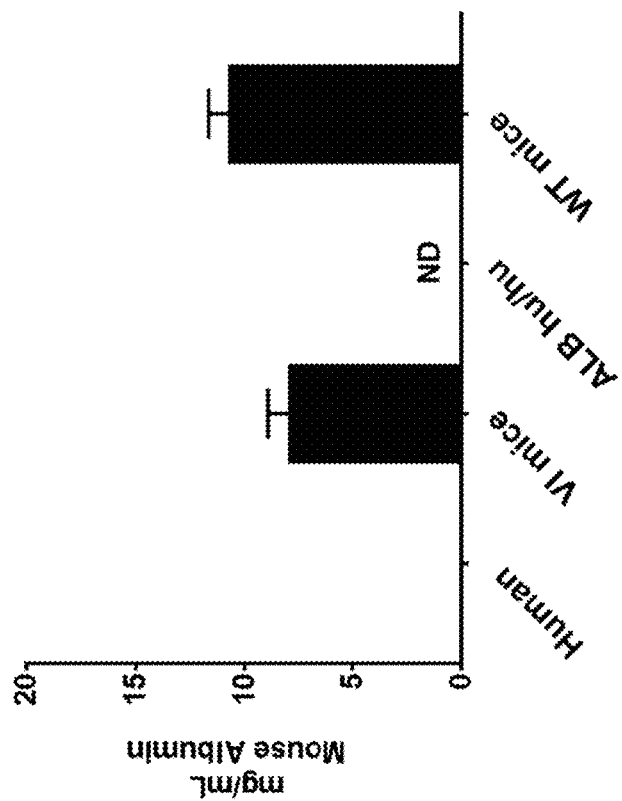
FIG. 4 shows human albumin levels in plasma samples from humanized albumin mice ($ALB^{hu/hu}$) and wild type (WT) mice. Pooled normal human plasma (George King-Biomedical Inc.) was used as a positive control. VelocImmune (VI) mice were used as a negative control.
Figure 5:
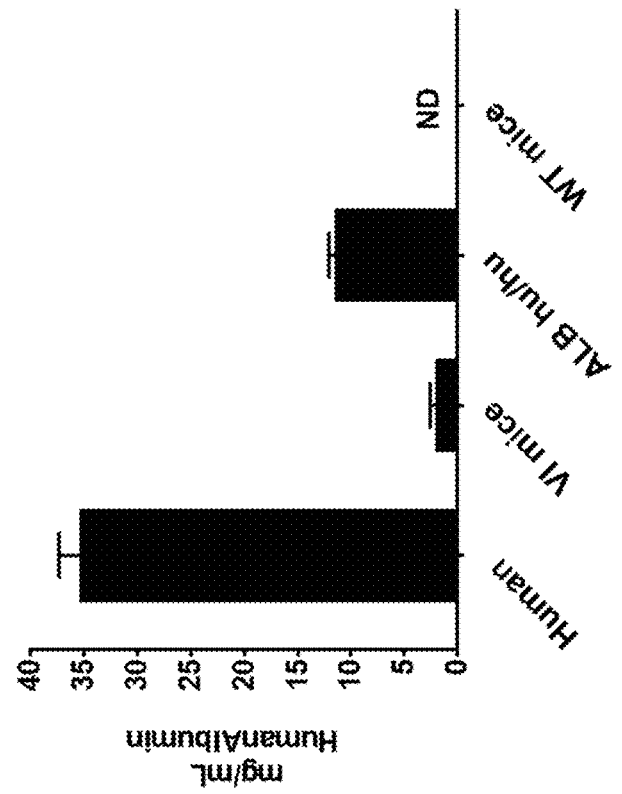
FIG. 5 shows mouse albumin levels in plasma samples from humanized albumin mice ($ALB^{hu/hu}$) and wild type (WT) mice. Pooled normal human plasma (George King-Biomedical Inc.) was used as a negative control. VI mice were used as a positive control.

| Assay | Description | Primer/Probe | Sequence |
|---|---|---|---|
| 7626hTU | Upstream Human Insertion | Fwd<br>Probe (MGB)<br>Rev | GTAACCTTTATTTCCCTTCTTTTTCTCTT (SEQ ID NO: 23)<br>AGCTCGGCTTATTC (SEQ ID NO: 24)<br>CGTGCATCTCGACGAAACAC (SEQ ID NO: 25) |
| 7626hTD | Downstream Human Insertion | Fwd<br>Probe (MGB)<br>Rev | GCAGAACCAAAGTAAGACTAAGCAAA (SEQ ID NO: 26)<br>AGAACAAATTACCTGATTTC (SEQ ID NO: 27)<br>TGTTTCGGTGACTATGGCCTTAT (SEQ ID NO: 28) |
| 7626mTU | Upstream Mouse LOA | Fwd<br>Probe (MGB)<br>Rev | GCCGAGAAGCACGTAAGAGTTT (SEQ ID NO: 29)<br>ATGTTTTTTCATCTCTGCTTGT (SEQ ID NO: 30)<br>AATACCAGGCTTCCATTACTAGAAAAA (SEQ ID NO: 31) |
| 7626mTD | Downstream Mouse LOA | Fwd<br>Probe (BHQ)<br>Rev | CCCTCCCATGGCCTAACAAC (SEQ ID NO: 32)<br>TTGGGCACAACAGATGTCAGAGAGC (SEQ ID NO: 33)<br>ACGTGCCTTGCATTGCTTA (SEQ ID NO: 34) | self-deleting selection cassette was self-deleted. Human albumin protein was detected in normal human plasma and humanized albumin mouse plasma samples but not in wild type (WT) mouse or VelocImmune (VI) mouse plasma samples. See FIG. 4. Mouse albumin protein was detected in wild type mouse plasma samples and VI mouse plasma samples but not in humanized albumin mice plasma samples. See FIG. 5. In particular, pooled normal human plasma (purchased from George King-Biomedical Inc.) had about 30-40 mg/mL of human albumin. Humanized albumin mice plasma had about 10-15 mg/mL of human albumin, but mouse albumin was not detectable. Normal VI and WT mouse plasma had about 7-13 mg/mL of mouse albumin.

Example 3. Validation of Mice Comprising a Humanized Albumin (ALB) Locus—Guide RNAs Targeting Human Albumin for F9 Insertion To further validate the humanized albumin mice, the humanized albumin mice were used to evaluate the use of CRISPR/Cas9 technology to integrate a F9 transgene into the albumin locus. Specifically, we tested integration and expression of integrated human F9 Padua variant (hF9-R338L) in homozygous humanized albumin mice. Various guide RNAs were designed against intron 1 of the human albumin locus. Two separate mouse experiments were set up using the ALB$^{hu/hu}$ mice to screen a total of 11 guide RNAs, each targeting the first intron of the human albumin locus. All mice were weighed and injected via tail vein at day 0 of the experiment. Blood was collected at weeks 1, 3, 4, and 6 via tail bleed, and plasma was separated. Mice were terminated at week 7. Blood was collected via the vena cava, and plasma was separated. Livers and spleens were dissected as well. The guide sequences (DNA-targeting segments) of these guide RNAs are provided in Table 5.

AAV8 packaged with a bi-directional hF9 insertion template (SEQ ID NO: 63; ITR-splice acceptor-hF9 (exons 2-8)-bGH-SV40 polyA-codon optimized hF9-pLac-pMB-splice acceptor-Kan resistance) at a dose of 3E11 viral genomes per mouse. Five ALB$^{hu/hu}$ male mice between 12 and 14 weeks old were injected per group. Five mice from same cohort were injected with AAV8 packaged with a CAGG promoter operably linked to hF9 (SEQ ID NO: 64; CAGG-ITR-hF9-WPRE-bGH-ITR-pLac-pMB-Amp resistance), which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

In the second experiment, the LNPs comprising Cas9 mRNAs and each of the following six guide RNAs separately were tested: G009860, G012764, G009844, G009857, G012752, G012753, and G012761. LNPs were diluted to 0.3 mg/kg (using an average weight of 40 grams) and co-injected with AAV8 packaged with the bi-directional hF9 insertion template (SEQ ID NO: 63) at a dose of 3E11 viral genomes per mouse. Five ALB$^{hu/hu}$ male mice 30 weeks old were injected per group. Five mice from same cohort were injected with AAV8 packaged with a CAGG promoter operably linked to hF9 (SEQ ID NO: 64), which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

For analysis, an ELISA was performed to measure levels of hFIX circulating in the mice at each timepoint. Human Factor IX ELISA Kits (ab188393) were used for this purpose, and all plates were run with human pooled normal

TABLE 5

Human Albumin gRNA Sequences and Chromosomal Coordinates.

| Guide ID | Guide Sequence | Human Genomic Coordinates (hg38) | SEQ ID NO: |
|---|---|---|---|
| G009844 | GAGCAACCUCACUCUUGUCU | chr4:73405113-73405133 | 49 |
| G009852 | UGCAUUUGUUUCAAAAUAUU | chr4:73404999-73405019 | 50 |
| G009857 | AUUUAUGAGAUCAACAGCAC | chr4:73404761-73404781 | 51 |
| G009859 | UUAAAUAAAGCAUAGUGCAA | chr4:73404727-73404747 | 52 |
| G009860 | UAAAGCAUAGUGCAAUGGAU | chr4:73404722-73404742 | 53 |
| G009874 | UAAUAAAAUUCAAACAUCCU | chr4:73404561-73404581 | 54 |
| G012752 | UGACUGAAACUUCACAGAAU | chr4:73404664-73404684 | 55 |
| G012753 | GACUGAAACUUCACAGAAUA | chr4:73404665-73404685 | 56 |
| G012761 | AGUGCAAUGGAUAGGUCUUU | chr4:73404714-73404734 | 57 |
| G012764 | CCUCACUCUUGUCUGGGCAA | chr4:73405107-73405127 | 58 |
| G012765 | ACCUCACUCUUGUCUGGGCA | chr4:73405108-73405128 | 59 |
| G012766 | UGAGCAACCUCACUCUUGUC | chr4:73405114-73405134 | 60 |

Figure 6A:
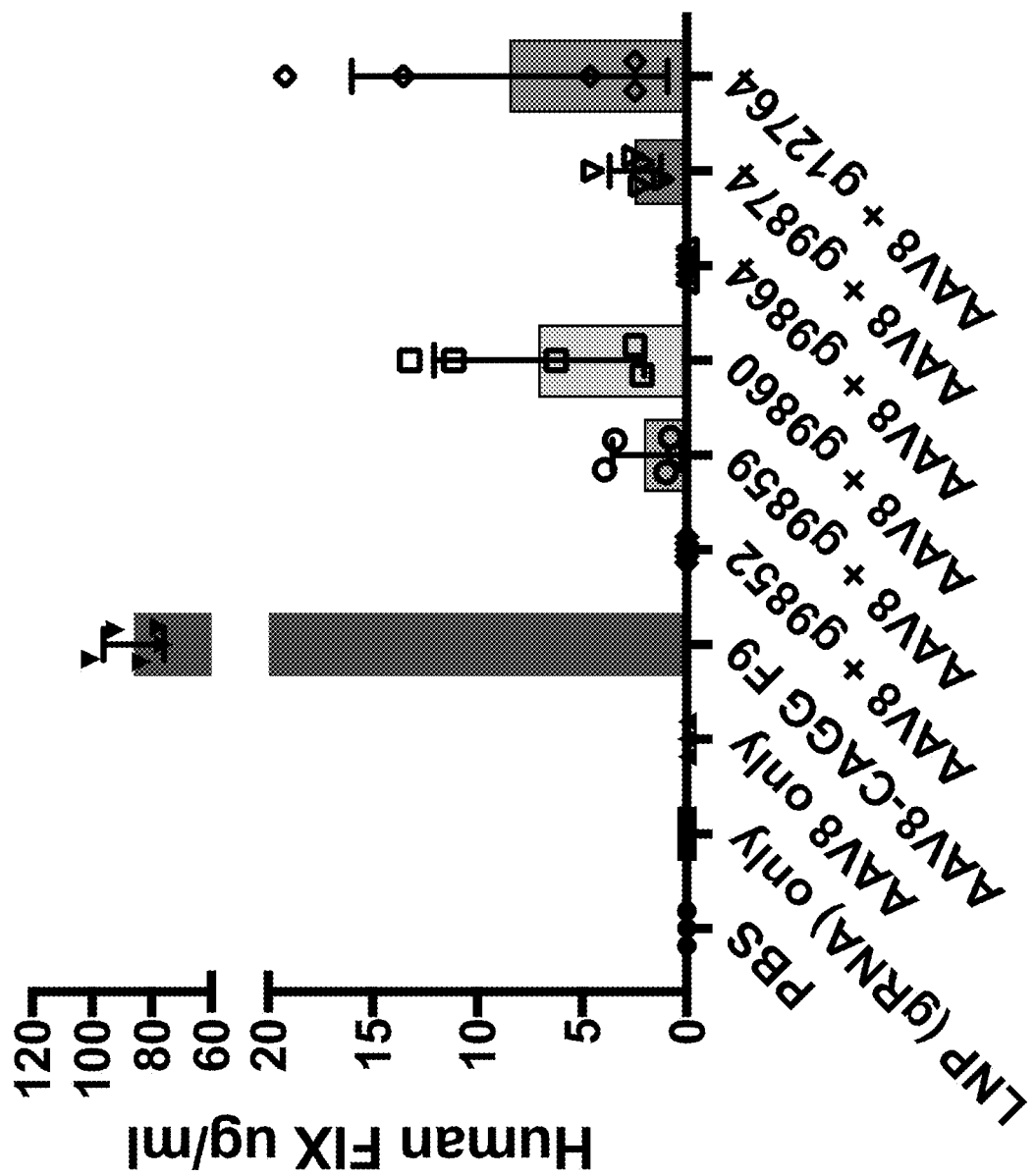
FIGS. 6A and 6B show human Factor IX plasma levels from AAV-hF9 insertion in humanized albumin mice.
Figure 6B:
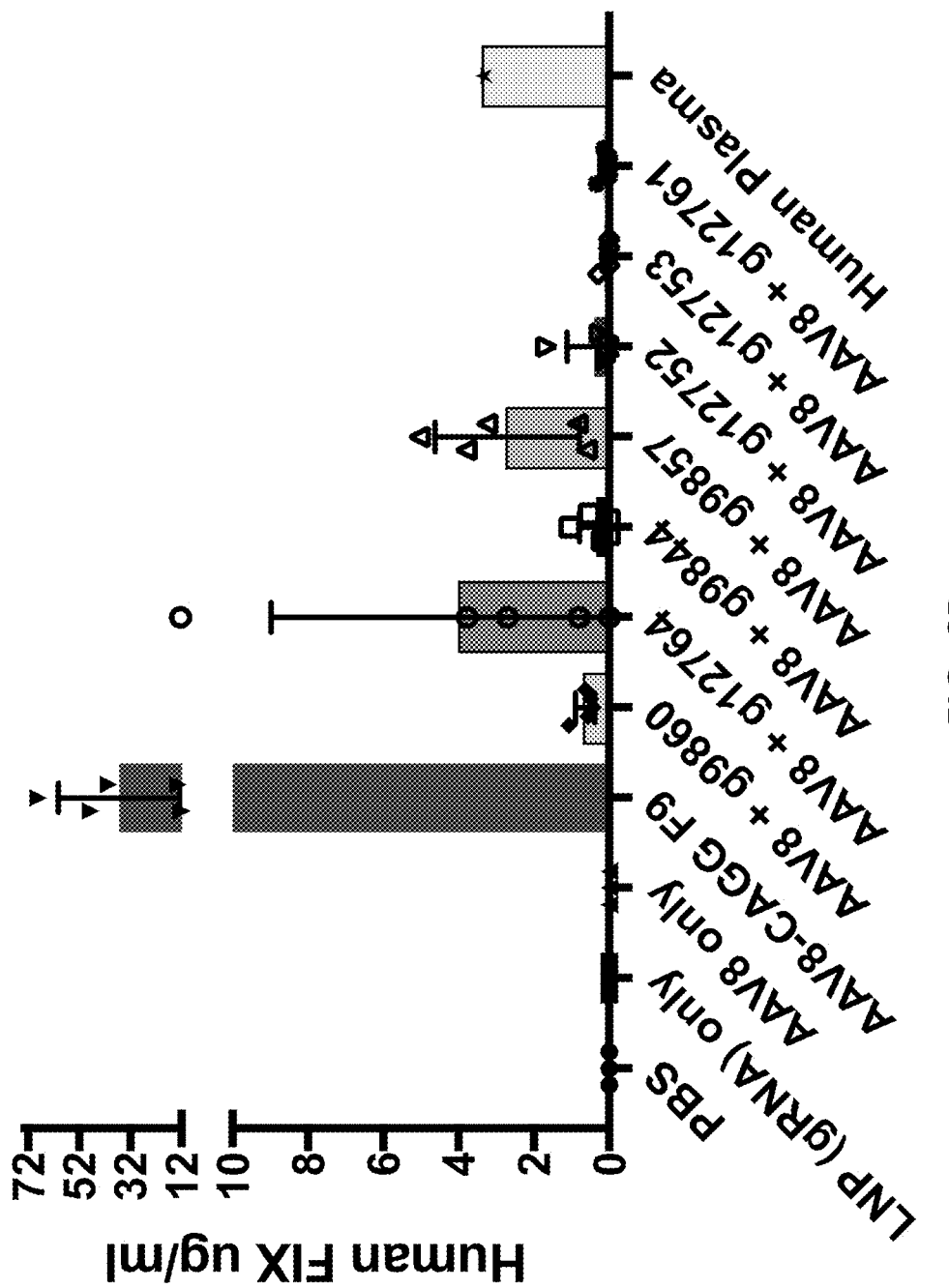

In the first experiment, the LNPs comprising Cas9 mRNAs and each of the following six guide RNAs separately were tested: G009852, G009859, G009860, G009864, G009874, and G012764. LNPs were diluted to 0.3 mg/kg (using an average weight of 30 grams) and co-injected with plasma from George King Bio-Medical as a positive assay control. Human Factor IX expression levels in the plasma samples in each group at week 6 post-injection are shown in FIGS. 6A and 6B. Consistent with the in vitro insertion data, low to no Factor IX serum levels were not detected when guide RNA G009852 was used. Consistent with the lack of an adjacent PAM sequence in human albumin, Factor IX serum levels were not detectable when guide RNA G009864 was used. The guide sequence (DNA-targeting segment) of G009864 is UACUUUGCACUUUCCUUAGU (SEQ ID NO: 61), and it targets cyno genomic coordinates (mf5) chr5:61199187-61199207. Factor IX expression in the serum was observed for several of the other guide RNAs, including G009857, G009859, G009860, G009874, and G0012764.

Spleens and a portion of the left lateral lobe of all livers were submitted for next-generation sequencing (NGS) analysis. NGS was used to assess the percentage of liver cells with insertions/deletions (indels) at the humanized albumin locus at week 7 post-injection with AAV-hF9 donor and LNP-CRISPR/Cas9. Consistent with the lack of an adjacent PAM sequence in human albumin, no editing was detectable in the liver when guide RNA G009864 was used. Editing in the liver was observed for the groups using guide RNAs G009859, G009860, G009874, and G012764 (data not shown).

Figure 7:
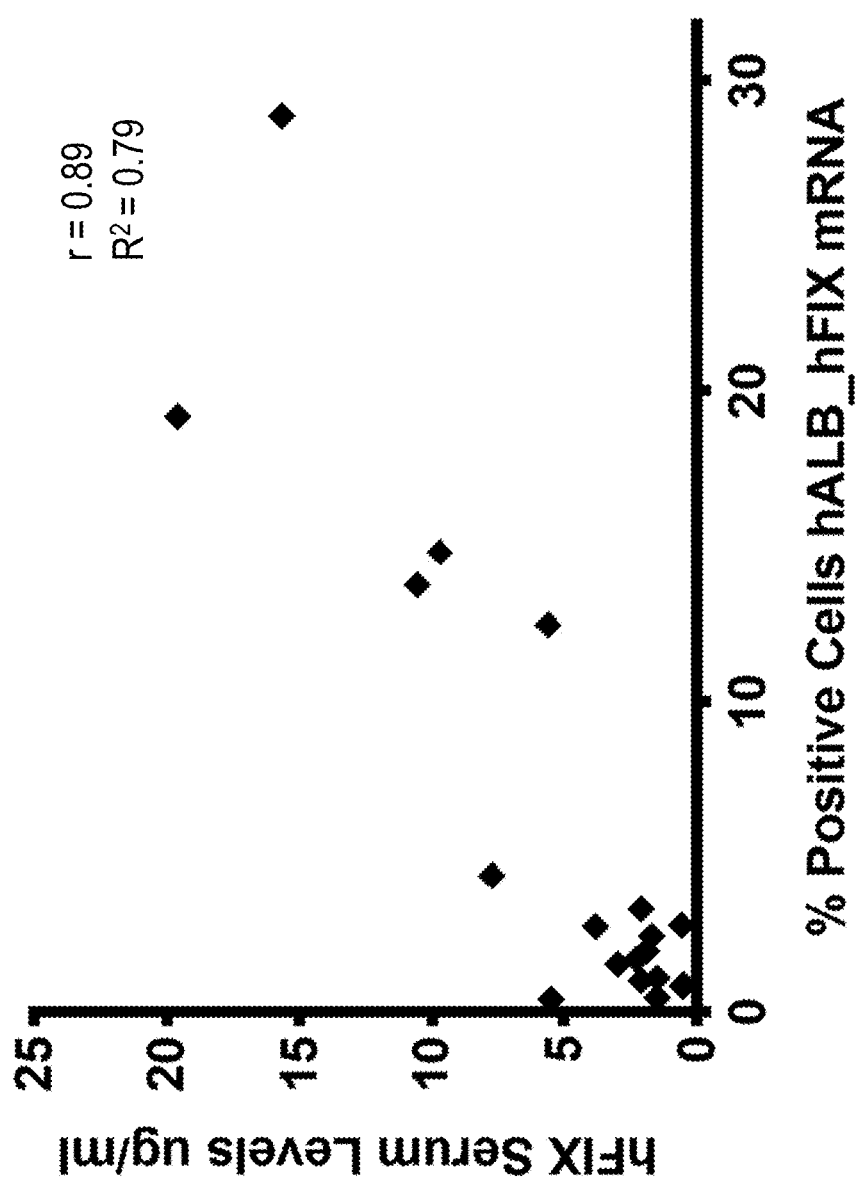
FIG. 7 shows human Factor IX plasma levels at week 7 post-injection with AAV-hF9 donor and LNP-CRISPR/Cas9 plotted against the percentage of cells positive for hALB-hFIX mRNA as determined by BASESCOPE™.

The remaining liver was fixed for 24 hours in 10% neutral buffered formalin and then transferred to 70% ethanol. Four to five samples from separate lobes were cut and shipped to HistoWisz and were processed and embedded in paraffin blocks. Five-micron sections were then cut from each paraffin block, and BASESCOPE™ was performed on the Ventana Ultra Discovery (Roche) using the universal BASESCOPE™ procedure and reagents by Advanced Cell Diagnostics and a custom designed probe that targets the unique mRNA junction formed between the human albumin signal sequence from the first intron of the ALB$^{hu/hu}$ albumin locus and the hF9 transgene when successful integration and transcription is achieved. HALO imaging software (Indica Labs) was then used to quantify the percentage of positive cells in each sample. The average of percentage positive cells across the multiple lobes for each animal was then correlated to the hFIX levels in the serum at week 7. The results are shown in FIG. 7 and Table 6. The week 7 serum levels and the % positive cells for the hALB-hFIX mRNA strongly correlated (r=0.89; R$^2$=0.79).

TABLE 6

Week 7 hFIX and BASESCOPE™ Data.

| Mouse | Guide | hFIX ug/mL (Week 7) | % mRNA Probe (4-5 Sections) | STD % mRNA Probe | Total Cells Counted |
|---|---|---|---|---|---|
| 1 | Buffer | ND | 0.09 | 0.03 | 152833 |
| 4 | AAV Only | ND | 0.53 | 0.67 | 351084 |
| 7 | LNP Only | ND | 0.48 | 0.33 | 75160 |
| 10 | CAG F9 | 211.8 | 0.20 | 0.22 | 190277 |
| 15 | G009852 | ND | 0.30 | 0.09 | 144518 |
| 20 | G009859 | 0.5 | 0.82 | 0.45 | 143817 |
| 21 | G009859 | 0.5 | 0.88 | 0.43 | 160172 |
| 22 | G009859 | 2.3 | 1.71 | 1.54 | 26015 |
| 23 | G009859 | 3.8 | 2.74 | 0.59 | 183085 |
| 24 | G009859 | 0.6 | 2.78 | 1.96 | 152424 |
| 25 | G009860 | 5.6 | 12.46 | 5.80 | 78935 |
| 26 | G009860 | 10.6 | 13.76 | 5.32 | 112252 |
| 27 | G009860 | 9.7 | 14.80 | 5.45 | 201592 |
| 28 | G009860 | 2.1 | 3.32 | 0.76 | 84710 |
| 29 | G009860 | 3.0 | 1.52 | 0.35 | 203277 |
| 30 | G009864 | ND | 1.94 | 1.78 | 145807 |
| 35 | G009874 | 1.7 | 2.42 | 1.14 | 126665 |
| 36 | G009874 | 1.5 | 1.08 | 0.53 | 195861 |
| 37 | G009874 | 2.1 | 1.02 | 1.29 | 181679 |
| 38 | G009874 | 5.5 | 0.40 | 0.43 | 175359 |
| 39 | G009874 | 1.5 | 0.44 | 0.18 | 205417 |
| 40 | G012764 | 15.7 | 28.85 | 7.11 | 167824 |
| 41 | G012764 | 19.6 | 19.17 | 8.23 | 70081 |
| 42 | G012764 | 1.9 | 1.95 | 1.79 | 154742 |
| 43 | G012764 | 7.7 | 4.38 | 0.68 | 114060 |
| 44 | G012764 | 3.0 | 1.64 | 1.04 | 238623 |
| 43 | DapB (−) | — | 0.12 | 0.07 | 144730 |

Example 4. Validation of Mice Comprising a Humanized Albumin (ALB) Locus— F9 Insertion in F9 KO Mice To further validate the humanized albumin mice, the humanized albumin mice were crossed with F9 knockout mice to create ALB$^{m/hu}$×F9$^{−/−}$ mice (heterozygous for humanization of albumin locus and homozygous F9 knockout) to be used to evaluate the use of CRISPR/Cas9 technology to integrate a F9 transgene into the albumin locus.

The humanized albumin F9 KO mice were then used to test insertion of a human F9 Padua variant (hF9-R338L) transgene into intron 1 of the humanized albumin locus. All mice were weighed and injected via tail vein at day 0 of the experiment. Blood was collected at weeks 1 and 3 via tail bleed, and plasma was separated. Mice were terminated at week 4. Blood was collected via the vena cava, and plasma was separated. Livers and spleens were dissected as well.

LNPs comprising Cas9 mRNA and the following two guide RNAs separately were tested: G009860 (targeting the first intron of the human albumin locus) and G000666 (targeting the first intron of the mouse albumin locus). The guide sequence (DNA-targeting segment) of G009860 is provided in Table 5. The guide sequence of G000666 is CACUCUUGUCUGUGGAAACA (SEQ ID NO: 62), and it targets mouse genomic coordinates (mm10) chr5:90461709-90461729. G009860 was diluted to 0.3 mg/kg, and G000666 was diluted to 1.0 mg/kg (using an average weight of 31.2 grams), and both were co-injected with AAV8 packaged with a bi-directional hF9 insertion template (SEQ ID NO: 63) at a dose of 3E11 viral genomes per mouse. Five ALB$^{ms/hu}$×F9$^{−/−}$ male mice (16 weeks old) were injected per group. Five mice from same cohort were injected with AAV8 packaged with a CAGG promoter operably linked to hF9 (SEQ ID NO: 64), which leads to episomal expression of hF9 (at 3E11 viral genomes per mouse). There were six negative control animals with one mouse per group that was injected with buffer alone or AAV8 packaged with the bi-directional hF9 insertion template alone, and two mice per group that were injected with LNP-G009860 or LNP-G000666 alone at 0.3 mg/kg and 1.0 mg/kg, respectively.

For analysis, an ELISA was performed to measure levels of hFIX circulating in the mice at each timepoint. Human Factor IX ELISA Kits (ab188393) were used for this purpose, and all plates were run with human pooled normal plasma from George King Bio-Medical as a positive assay control. Spleens and a portion of the left lateral lobe of all livers were submitted for NGS analysis.

Figure 8:
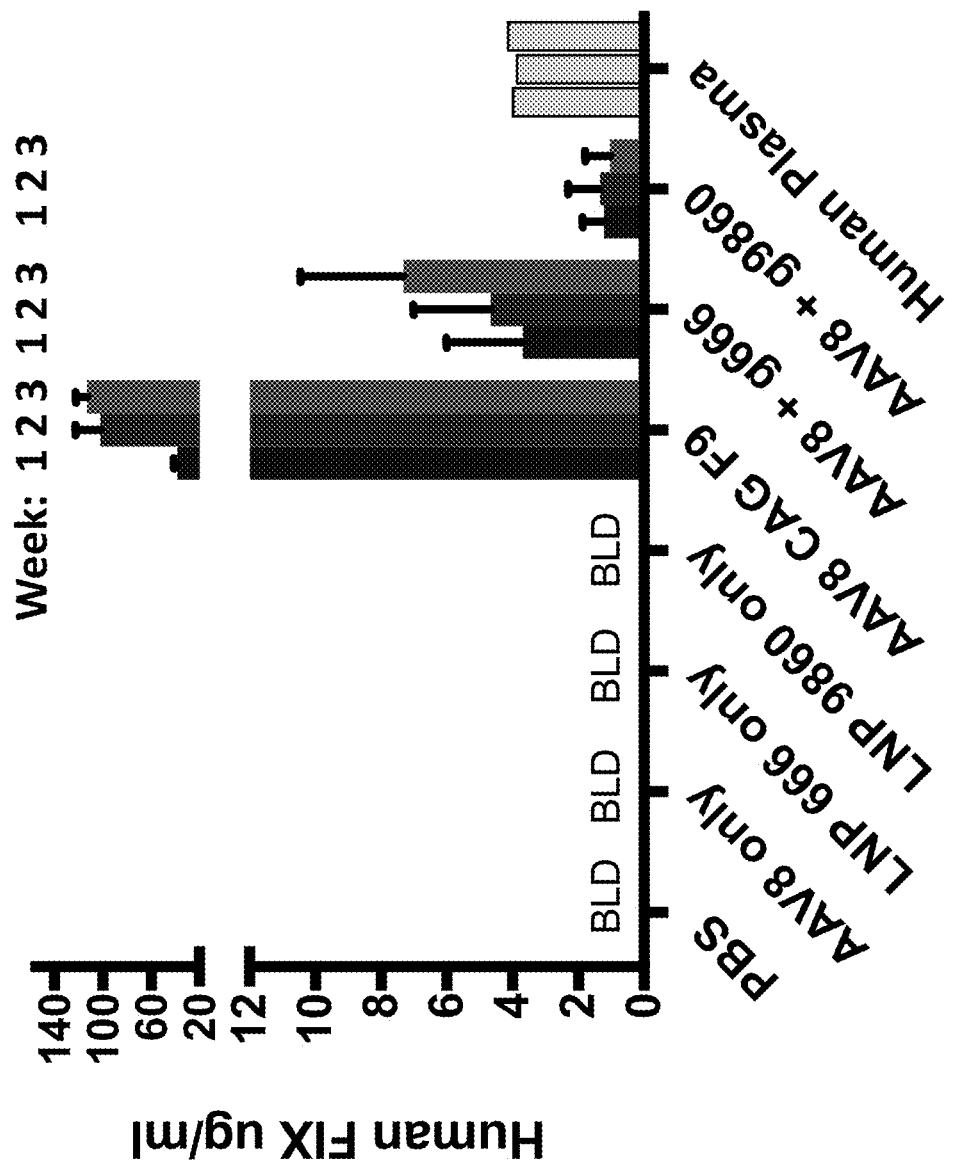
FIG. 8 shows human Factor IX plasma levels from AAV-hF9 insertion in $ALB^{m/hu} \times F9^{-/-}$ mice.

Human Factor IX expression levels in the plasma samples in each group at weeks 1, 2, and 4 post-injection are shown in FIG. 8 and in Table 7. In addition, NGS results showing insertion and deletion (indel) levels at the albumin locus in the liver and spleen are shown in Table 7. As shown in FIG.

8 and Table 7, hFIX was detected in the plasma of treated Alb$^{+/hu}$/F9$^{-/-}$ mice at 1, 3, and 4 weeks, with ELISA showing expression values of 0.5-10 µg/mL at 1, 3 and 4 weeks.

TABLE 7

Human FIX Plasma Levels and NGS Results.

| Sample | Week 1 (µg/mL) | Week 3 (µg/mL) | Week 4 (µg/mL) | INDEL Liver | INDEL Spleen |
|---|---|---|---|---|---|
| S1 PBS | BLD | BLD | BLD | ND | 0.12 |
| S18 AAV8 only | BLD | BLD | BLD | 0.73 | 0.10 |
| S2 G000666 only | BLD | BLD | BLD | 37.48 | 0.92 |
| S4 G000666 only | BLD | BLD | BLD | 30.67 | 1.17 |
| S19 G009860 only | BLD | BLD | BLD | 12.25 | 0.31 |
| S20 G009860 only | BLD | BLD | BLD | 10.73 | 0.45 |
| S10 CAG | 42.60 | 129.83 | 117.74 | 1.45 | 0.12 |
| S14 CAG | 35.55 | 82.25 | 100.95 | 0.08 | 0.11 |
| S15 CAG | 37.30 | 115.51 | 107.26 | 0.10 | 0.05 |
| S16 CAG | 36.39 | 81.27 | 116.24 | 0.05 | 0.10 |
| S17 CAG | 40.50 | 101.38 | 124.15 | 0.16 | 0.06 |
| S5 AAV8 + G000666 | 2.90 | 5.00 | 8.79 | 41.46 | 1.43 |
| S6 AAV8 + G000666 | 4.67 | 6.11 | 10.29 | 33.81 | 1.59 |
| S7 AAV8 + G000666 | 2.88 | 3.15 | 3.01 | 33.47 | 1.04 |
| S8 AAV8 + G000666 | 0.94 | 1.61 | No sample | 36.54 | 1.34 |
| S9 AAV8 + G000666 | 7.14 | 7.53 | 7.23 | 30.63 | 1.38 |
| S11 AAV8 + G009860 | 0.73 | 0.62 | 0.86 | 11.15 | 0.52 |
| S12 AAV8 + G009860 | 0.52 | 0.43 | 0.47 | 7.05 | 0.39 |
| S13 AAV8 + G009860 | 1.71 | 1.89 | 0.93 | 18.38 | 0.57 |
| S21 AAV8 + G009860 | 1.21 | 2.79 | 0.59 | 13.44 | 0.22 |
| S22 AAV8 + G009860 | 2.06 | 1.03 | 2.37 | 18.06 | 0.19 |
| Human | 4.00 | 3.91 | 4.12 | N/A | N/A |

The remaining liver was fixed for 24 hours in 10% neutral buffered formalin and then transferred to 70% ethanol. Four to five samples from separate lobes were cut and shipped to HistoWiz and were processed and embedded in paraffin blocks. Five-micron sections were then cut from each paraffin block for analysis via BASESCOPE™ on the Ventana Ultra Discovery (Roche) using the universal BASESCOPE™ procedure and reagents by Advanced Cell Diagnostics and a custom designed probe that targets the unique mRNA junction formed between either the human or the mouse albumin signal sequence from the first intron of each respective albumin locus in the ALB$^{ms/hu}$ mice and the hF9 transgene when successful integration and transcription is achieved. HALO imaging software (Indica Labs) is used to quantify the percentage of positive cells in each sample.

Next, terminal blood was used for assessment of functional coagulation activity by activated partial thromboplastin time (aPTT) and Thrombin Generation Assay (TGA). Activated partial thromboplastin time (aPTT) is a clinical measurement of intrinsic pathway clotting activity in plasma. Plasma is induced to clot by the addition of ellagic acid or kaolin, both of which activate coagulation factor XII in the intrinsic pathway (as known as the contact pathway) of coagulation, that subsequently results in the generation of fibrin from fibrinogen once thrombin is activated. The aPTT assay provides an estimation of an individual's ability to generate a clot, and this information can be used to determine risk of bleeding or thrombosis. To test aPTT, a semi-automated benchtop system (Diagnostica Stago STart 4) with an electro-mechanical clot detection method (viscosity-based detection system) was used to assess clotting in plasma. To each cuvette with a steel ball, 50 µL of citrated plasma was added and incubated at 37° C. for 5 min, and then clotting was triggered with the addition of 50 µL of ellagic acid (final concentration of 30 µM) at 37° C. for 300 seconds. Following final activation of clotting by adding 50 µL of 0.025 M calcium chloride (final concentration of 8 mM) to each cuvette, the steal ball began to oscillate back and forth between the two drive coils. The movement of the ball was detected by the receiver coil. The generation of fibrin increased plasma viscosity until the ball ceased to move, which was recorded as the clotting time. The only parameter measured was clotting time. Runs were conducted in duplicate.

Thrombin generation assay (TGA) is a non-clinical assessment of the kinetics of thrombin generation in activated plasma. Thrombin generation is an essential process of coagulation because thrombin is responsible for activation of other coagulation factors and propagation of additional thrombin (via FXI activation) for the conversion of fibrinogen to fibrin. Thrombin generation assay provides an estimation of an individual's ability to generate thrombin, and this information can be used to determine risk of bleeding or thrombosis. To perform the TGA, a calibrated automated thrombogram was used to assess thrombin generation levels in a spectrophotometer (Thrombinograph™, Thermo Scientific). For high throughput experimentation, 96-well plates (Immulon II FIB) were used. To each well, 55 µL of citrated plasma (4× diluted with saline for mouse plasma) was added and incubated at 37° C. for 30 min. Thrombin generation is triggered with the addition of 15 µL of 2 µM ellagic acid (final concentration of 0.33 µM) at 37° C. for 45 min. Thrombin generation was determined following the automated injection of 15 µL of the fluorogenic substrate with 16 mM CaCl$_2$) (FluCa; Thrombinoscope BV) into each well. The fluorogenic substrate reacted with the generated thrombin, which was measured continuously in the plasma every 33 sec for 90 min at 460 nm. The fluorescence intensity was proportional to the proteolytic activity of thrombin. The main parameters measured in the tracing were lag time, peak thrombin generation, time to peak thrombin generation, and endogenous thrombin potential (ETP). The lag time provides an estimation of time required for initial detection of thrombin in plasma. The peak is the maximum amount of thrombin generated at a given time after activation. Time to peak thrombin generation is time from initiation of the coagulation cascade to the peak generation of thrombin. ETP is the total amount of thrombin generated during the 60 minutes measured. Runs were conducted in duplicate.

Figure 9:
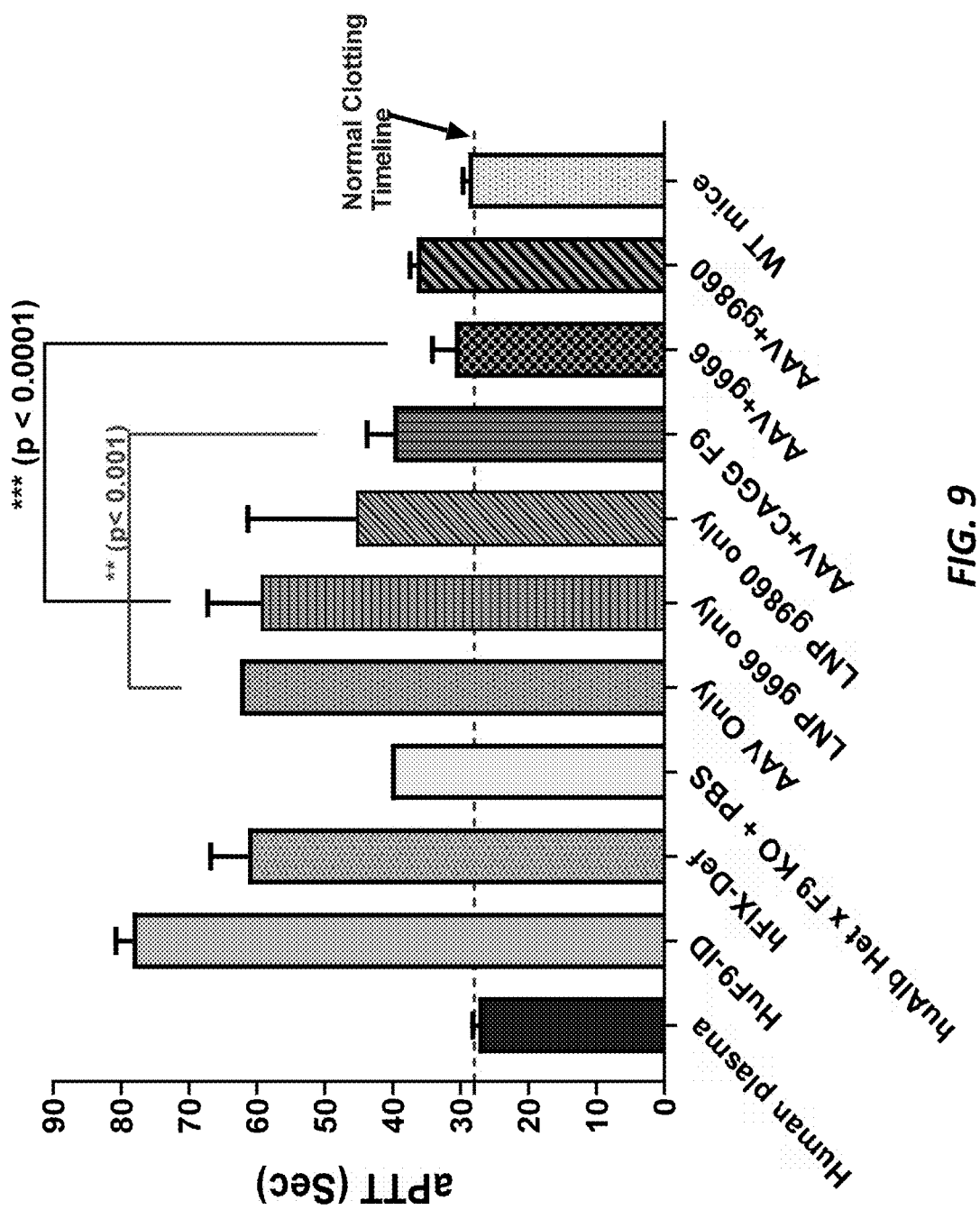
FIG. 9 shows aPTT effects in human and mouse plasma samples from AAV-hF9 insertion in $ALB^{m/hu} \times F9^{-/-}$ mice.

As shown in FIG. 9 and Table 8, insertion of the hF9 transgene using either the mouse albumin gRNA or the human albumin gRNA showed recovered clotting function in the aPTT assay. Saline, AAV only, and LNP only negative control samples showed prolonged aPTT times of 45-60 seconds. The positive control CAGG and test samples (AAV8+LNP) were closer to the normal human aPTT of 28-34 seconds.

TABLE 8 aPTT and TGA-EA.

| Sample # | I.V. Injection | Week 4 F9 µg/mL | Average aPTT (sec) | TGA-EA Peak (nM) |
|---|---|---|---|---|
| 1 | PBS | BLD | 40.2 | 11.13 |
| 18 | AAV Only | BLD | 62.5 | −1 |
| 2 | LNP G000666 only | BLD | 53.9 | −1 |
| 4 | LNP G000666 only | BLD | 65.0 | 2.45 |
| 19 | LNP G009860 only | BLD | 34.1 | 42.83 |
| 20 | LNP G009860 only | BLD | 56.7 | 18.07 |
| 10 | AAV + CAGGF9 | 117.74 | 41.1 | 42.65 |
| 14 | AAV + CAGGF9 | 100.95 | 34.1 | 49.96 |
| 15 | AAV + CAGGF9 | 107.26 | 42.2 | 49.49 |
| 16 | AAV + CAGGF9 | 116.24 | 37.9 | 44.46 |
| 17 | AAV + CAGGF9 | 124.15 | 44.1 | 38.02 |

TABLE 8-continued aPTT and TGA-EA.

| Sample # | I.V. Injection | Week 4 F9 µg/mL | Average aPTT (sec) | TGA-EA Peak (nM) |
|---|---|---|---|---|
| 5 | AAV + G000666 | 8.79 | 31.3 | 72.11 |
| 6 | AAV + G000666 | 10.29 | 32.6 | 90.14 |
| 7 | AAV + G000666 | 3.01 | 33.5 | 58.33 |
| 8 | AAV + G000666 | no sample | NA | NA |
| 9 | AAV + G000666 | 7.23 | 25.9 | 67.23 |
| 11 | AAV + G009860 | 0.86 | 36.8 | 56.92 |
| 12 | AAV + G009860 | 0.47 | 37.7 | 45.16 |
| 13 | AAV + G009860 | 0.93 | 35.3 | 60.45 |
| 21 | AAV + G009860 | 0.59 | 36.1 | 47.44 |
| 22 | AAV + G009860 | 2.37 | >300 | Clots in tube |

Figure 10A:
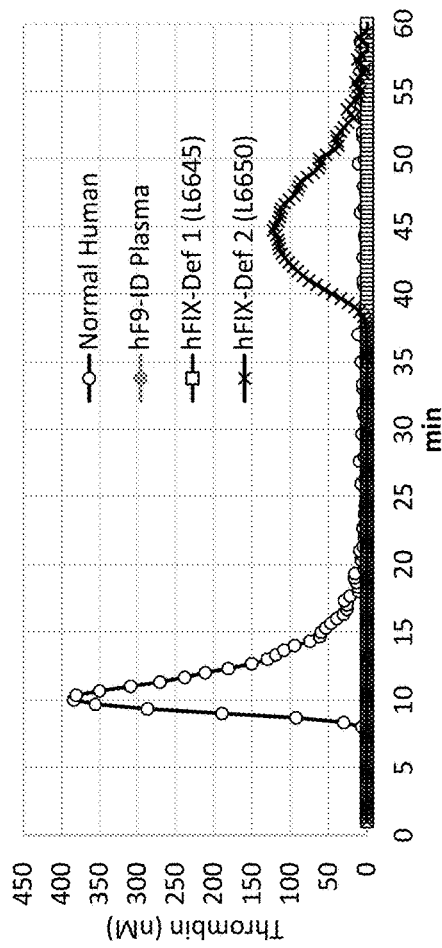
FIGS. 10A and 10B show TGA-EA profiles.
Figure 10B:
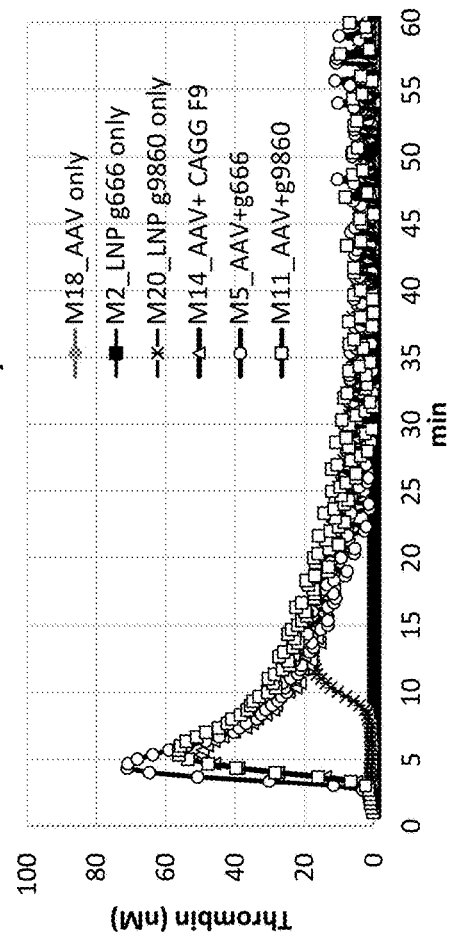
Figure 11:
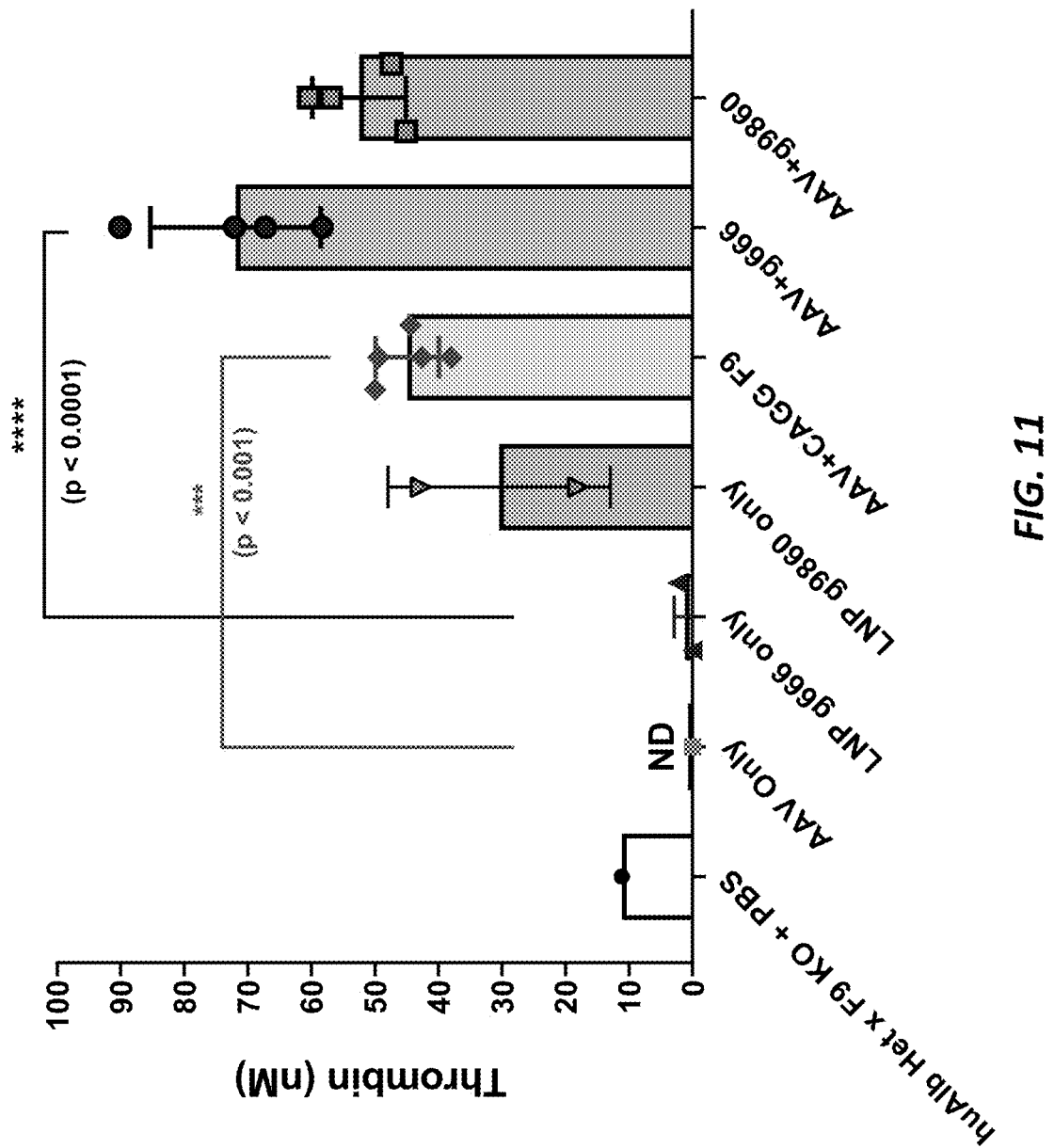
FIG. 11 shows thrombin generation in mouse plasma samples from AAV-hF9 insertion in ALB$^{m/hu}$×F9$^{-/-}$ mice.

As shown in FIGS. 10A, 10B, and 11 and in Table 8, insertion of the hF9 transgene using either the mouse albumin gRNA or the human albumin gRNA showed increased thrombin generation in TGA-EA analysis. Thrombin concentrations were higher in the positive control CAGG and AAV8+LNP as compared to the negative control samples.

In conclusion, hFIX was detected in the plasma of Alb$^{+/hu}$/F9$^{-/-}$ mice at 1, 3, and 4 weeks, and the expressed hFIX-R338L was found to be functional since thrombin was generated in a TGA assay, and aPTT clotting time was improved.

We claim:

1. A method of determining whether a genome-editing reagent modifies a humanized albumin gene in vivo, comprising:
   (a) administering the genome-editing reagent to a genetically modified mouse whose genome comprises a humanized albumin gene in which the region from the start codon to the stop codon of an endogenous albumin gene is replaced with a human nucleic acid sequence encoding human albumin and a human albumin signal peptide,
   wherein the human nucleic acid sequence is operably linked to an endogenous albumin promoter and comprises the region from the start codon to the stop codon of a human albumin gene, and
   wherein the mouse functionally expresses human albumin and has a serum level of human albumin that is at least as high as the serum level of mouse albumin in a wild type mouse; and
   (b) determining whether the genome-editing reagent modified the humanized albumin gene in the mouse.

2. The method of claim 1, wherein the humanized albumin gene comprises a human albumin 3' untranslated region.

3. The method of claim 1, wherein the humanized albumin gene comprises the nucleic acid sequence of SEQ ID NO: 17, 18, or 35 or encodes the protein of SEQ ID NO: 5.

4. The method of claim 1, wherein the humanized albumin gene further comprises a selection cassette.

5. The method of claim 1, wherein the mouse is homozygous for the humanized albumin gene.

6. The method of claim 1, wherein the mouse is heterozygous for the humanized albumin gene.

7. The method of claim 1, wherein the mouse comprises serum albumin levels of at least about 10 mg/mL.

8. The method of claim 1, wherein the mouse further comprises an inactivated factor 9 (F9) gene.

9. The method of claim 1, wherein the genome-editing reagent is administered by adeno-associated virus (AAV)-mediated delivery, lipid nanoparticle (LNP)-mediated delivery, or hydrodynamic delivery (HDD).

10. The method of claim 9, wherein the genome-editing reagent is administered by LNP-mediated delivery.

11. The method of claim 9, wherein the genome-editing reagent is administered by AAV8-mediated delivery.

12. The method of claim 1, wherein step (b) comprises isolating a liver from the genetically modified mouse and determining whether the genome-editing reagent modified the humanized albumin gene in liver tissue of the mouse.

13. The method of claim 1, wherein step (b) comprises determining whether the genome-editing reagent caused insertions or deletions within the humanized albumin gene in the mouse.

14. The method of claim 1, wherein the genome-editing reagent comprises a nuclease that targets a human albumin gene or a nucleic acid encoding the nuclease.

15. The method of claim 14, wherein the genome-editing reagent comprises a Cas protein and a guide RNA (gRNA) that targets a human albumin gene.

16. The method of claim 15, wherein the gRNA targets intron 1 of the human albumin gene.

17. The method of claim 15, wherein the Cas protein is a Cas9 protein.

18. The method of claim 1, wherein the genome-editing reagent is an exogenous nucleic acid sequence that targets a human albumin gene.

19. The method of claim 18, wherein the exogenous nucleic acid sequence:
  (I) is a single-stranded oligodeoxynucleotide;
  (II) does not comprise homology arms; or
  (III) comprises a donor sequence flanked by 5' and 3' homology arms.

20. The method of claim 19, wherein the 5' and 3' homology arms target intron 1 of a human albumin gene.

21. The method of claim 18, wherein the exogenous nucleic acid sequence encodes a protein.

22. The method of claim 21, wherein the protein encoded by a humanized albumin gene that has been targeted with the exogenous nucleic acid sequence is a heterologous protein comprising a human albumin signal peptide fused to the protein encoded by the exogenous nucleic acid sequence.

23. The method of claim 21, wherein the protein encoded by the exogenous nucleic acid sequence is a factor IX protein or a human factor IX protein.

24. The method of claim 23, wherein the assessing further comprises measuring serum levels of the factor IX protein or the human factor IX protein in the genetically modified mouse and/or comprises assessing activated partial thromboplastin time or performing a thrombin generation assay.

25. The method of claim 21, wherein the assessing further comprises measuring expression of a messenger RNA encoded by the exogenous nucleic acid sequence.

26. The method of claim 25, wherein the measuring expression of the messenger RNA encoded by the exogenous nucleic acid sequence comprises an in situ hybridization assay to quantify expression of the messenger RNA at single-cell resolution.

27. The method of claim 25, wherein the measuring expression of the messenger RNA encoded by the exogenous nucleic acid sequence comprises measuring expression of the messenger RNA in multiple lobes from the liver of the genetically modified mouse.

28. The method of claim 21, wherein the assessing further comprises measuring expression of the protein.

29. The method of claim 28, wherein the measuring expression of the protein comprises measuring:
  (a) serum levels of the protein in the genetically modified mouse; or
  (b) expression in the liver of the genetically modified mouse.

30. The method of claim 1, wherein the genome-editing reagent comprises (1) a nuclease that targets a human albumin gene or a nucleic acid encoding the nuclease and (2) an exogenous nucleic acid sequence that targets the human albumin gene,
  wherein the exogenous nucleic acid sequence encodes a protein, and
  wherein the protein encoded by a humanized albumin gene that has been targeted with the exogenous nucleic acid sequence is a heterologous protein comprising a human albumin signal peptide fused to the protein encoded by the exogenous nucleic acid sequence.

* * * * *